US011559591B2

(12) United States Patent
Bradbury et al.

(10) Patent No.: US 11,559,591 B2
(45) Date of Patent: Jan. 24, 2023

(54) ULTRASMALL NANOPARTICLES LABELED WITH ZIRCONIUM-89 AND METHODS THEREOF

(71) Applicants: Memorial Sloan Kettering Cancer Center, New York, NY (US); Cornell University, Ithaca, NY (US)

(72) Inventors: Michelle S. Bradbury, New York, NY (US); Feng Chen, New York, NY (US); Ulrich Wiesner, Ithaca, NY (US); Kai Ma, Ithaca, NY (US)

(73) Assignees: Memorial Sloan Kettering Cancer Center, New York, NY (US); Cornell University, Ithaca, NY (US)

( * ) Notice: Subject to any disclaimer, the term of this patent is extended or adjusted under 35 U.S.C. 154(b) by 5 days.

(21) Appl. No.: 16/616,368

(22) PCT Filed: May 17, 2018

(86) PCT No.: PCT/US2018/033098
§ 371 (c)(1),
(2) Date: Nov. 22, 2019

(87) PCT Pub. No.: WO2018/217528
PCT Pub. Date: Nov. 29, 2018

(65) Prior Publication Data
US 2020/0101180 A1    Apr. 2, 2020

Related U.S. Application Data

(60) Provisional application No. 62/510,859, filed on May 25, 2017.

(51) Int. Cl.
| | |
|---|---|
| *A61K 51/12* | (2006.01) |
| *A61P 35/00* | (2006.01) |
| *A61K 51/04* | (2006.01) |
| *A61K 51/08* | (2006.01) |
| *A61K 51/10* | (2006.01) |
| *A61K 49/00* | (2006.01) |
| *B82Y 5/00* | (2011.01) |
| *B82Y 15/00* | (2011.01) |

(52) U.S. Cl.
CPC ...... *A61K 51/1244* (2013.01); *A61K 49/0093* (2013.01); *A61K 51/0482* (2013.01); *A61K 51/082* (2013.01); *A61K 51/10* (2013.01); *A61P 35/00* (2018.01); *B82Y 5/00* (2013.01); *B82Y 15/00* (2013.01)

(58) Field of Classification Search
None
See application file for complete search history.

(56) References Cited

U.S. PATENT DOCUMENTS

| | | | |
|---|---|---|---|
| 3,867,519 | A | 2/1975 | Michaels |
| 3,870,791 | A | 3/1975 | Haddad et al. |
| 4,051,842 | A | 10/1977 | Hazel et al. |
| 4,136,177 | A | 1/1979 | Lin et al. |
| 4,140,122 | A | 2/1979 | Kuhl et al. |
| 4,255,415 | A | 3/1981 | Chrai et al. |
| 4,383,529 | A | 5/1983 | Webster |
| 4,688,506 | A | 8/1987 | van Breems |
| 4,713,224 | A | 12/1987 | Tamhankar et al. |
| 4,774,339 | A | 9/1988 | Haugland et al. |
| 4,788,603 | A | 11/1988 | Fujimura et al. |
| 4,810,636 | A | 3/1989 | Corey |
| 4,812,409 | A | 3/1989 | Babb et al. |
| 4,931,279 | A | 6/1990 | Bawa et al. |
| 5,187,288 | A | 2/1993 | Kang et al. |
| 5,248,782 | A | 9/1993 | Haugland et al. |
| 5,274,113 | A | 12/1993 | Kang et al. |
| 5,433,896 | A | 7/1995 | Kang et al. |
| 5,776,427 | A | 7/1998 | Thorpe et al. |
| 5,830,912 | A | 11/1998 | Gee et al. |
| 5,985,877 | A | 11/1999 | Dionne et al. |
| 6,254,852 | B1 | 7/2001 | Glajch et al. |
| 6,268,222 | B1 | 7/2001 | Chandler et al. |
| 7,601,355 | B2 | 10/2009 | Howard et al. |
| 8,084,001 | B2 | 12/2011 | Burns et al. |

(Continued)

FOREIGN PATENT DOCUMENTS

| | | |
|---|---|---|
| WO | WO-99/22026 A1 | 5/1999 |
| WO | WO-2004/074504 A2 | 9/2004 |

(Continued)

OTHER PUBLICATIONS

Omidfar et al. Single domain antibodies: a new concept for epidermal growth factor receptor and EGFRvIII targeting. 2012 DNA Cell Biol. 31: 1015-1026. (Year: 2012).*

Goel et al. VEGF121-conjugated mesoporous silica nanoparticle: a tumor targeted drug delivery system. 2014 ACS Appl. Mater. Interfaces 6: 21677-21685. (Year: 2014).*

Chen, F. et al., Target-or-Clear Zirconium-89 Labeled Silica Nanoparticles for Enhanced Cancer-Directed Uptake in Melanoma: A Comparison of Radiolabeling Strategies, Chemistry of Materials, 29(19):8269-8281, (2017).

DeTappe, A. et al., Advanced multimodal nanoparticles delay tumor progression with clinical radiation therapy, Journal of Controlled Release, 238:103-113 (2016).

(Continued)

*Primary Examiner* — Jennifer Lamberski
(74) *Attorney, Agent, or Firm* — Choate, Hall & Stewart LLP; William R. Haulbrook; Margo R. Monroe

(57) ABSTRACT

Described herein are nanoprobes comprising ultrasmall aminated and cRGDY-conjugated nanoparticles labeled with Zirconium-89 ($^{89}$Zr) and methods of their use. The provided compositions are renally clearable and possess suitable blood circulation half-time, high tumor active targeting capability, dominant renal clearance, low liver accumulation, and a high tumor-to-background ratio. The described nanoprobes exhibit great potential as "target-or-clear" tracers to human subjects for systemic targeted imaging (or treatment) of cancer.

22 Claims, 24 Drawing Sheets

(56) References Cited

U.S. PATENT DOCUMENTS

| | | | |
|---|---|---|---|
| 8,239,007 | B2 | 8/2012 | Voegele et al. |
| 8,298,677 | B2 | 10/2012 | Wiesner et al. |
| 8,389,679 | B2 | 3/2013 | Eckert et al. |
| 8,409,876 | B2 | 4/2013 | Wiesner et al. |
| 8,961,825 | B2 | 2/2015 | Wiesner et al. |
| 9,625,456 | B2 | 4/2017 | Bradbury et al. |
| 9,999,694 | B2 | 6/2018 | Bradbury et al. |
| 10,039,847 | B2 | 8/2018 | Bradbury et al. |
| 10,111,963 | B2 | 10/2018 | Yoo et al. |
| 10,485,881 | B2 | 11/2019 | Bradbury et al. |
| 10,548,997 | B2 | 2/2020 | Bradbury et al. |
| 10,548,998 | B2 | 2/2020 | Bradbury et al. |
| 2003/0219785 | A1 | 11/2003 | Hallahan et al. |
| 2004/0101822 | A1 | 5/2004 | Wiesner et al. |
| 2004/0248856 | A1 | 12/2004 | Lanza et al. |
| 2006/0106306 | A1 | 5/2006 | Essner et al. |
| 2006/0173362 | A1 | 8/2006 | Toms et al. |
| 2006/0183246 | A1 | 8/2006 | Wiesner et al. |
| 2006/0245971 | A1 | 11/2006 | Burns et al. |
| 2006/0251726 | A1 | 11/2006 | Lin et al. |
| 2008/0097225 | A1 | 4/2008 | Tearney et al. |
| 2008/0139787 | A1 | 6/2008 | De Jesus et al. |
| 2008/0213377 | A1 | 9/2008 | Bhatia et al. |
| 2008/0292556 | A1 | 11/2008 | Texier-Noques et al. |
| 2010/0261208 | A1 | 10/2010 | Schollhorn |
| 2010/0262017 | A1 | 10/2010 | Frangioni |
| 2011/0028662 | A1 | 2/2011 | Wiesner et al. |
| 2012/0107237 | A1 | 5/2012 | Miao et al. |
| 2013/0017265 | A1 | 1/2013 | Farokhzad et al. |
| 2013/0039848 | A1 | 2/2013 | Bradbury et al. |
| 2014/0028210 | A1 | 1/2014 | Maxik et al. |
| 2014/0248210 | A1 | 9/2014 | Bradbury et al. |
| 2015/0174268 | A1 | 6/2015 | Li |
| 2015/0182118 | A1 | 7/2015 | Bradbury et al. |
| 2015/0343091 | A1 | 12/2015 | Yoo et al. |
| 2015/0366995 | A1 | 12/2015 | Wiesner et al. |
| 2016/0018404 | A1 | 1/2016 | Iyer et al. |
| 2016/0202185 | A1 | 7/2016 | Zhuang et al. |
| 2017/0239378 | A1 | 8/2017 | Bradbury et al. |
| 2017/0326261 | A1 | 11/2017 | Oukhatar et al. |
| 2018/0093000 | A1 | 4/2018 | Bradbury et al. |
| 2018/0133346 | A1 | 5/2018 | Wiesner et al. |
| 2018/0169264 | A1 | 6/2018 | Bradbury et al. |
| 2018/0326103 | A1 | 11/2018 | Bradbury et al. |
| 2019/0070310 | A1 | 3/2019 | Bradbury et al. |
| 2020/0179538 | A1 | 6/2020 | Ma et al. |
| 2020/0289668 | A1 | 9/2020 | Bradbury et al. |
| 2020/0316219 | A1 | 10/2020 | Bradbury et al. |
| 2020/0376149 | A1 | 12/2020 | Bradbury et al. |
| 2020/0383943 | A1 | 12/2020 | Bradbury et al. |
| 2021/0145985 | A1 | 5/2021 | Bradbury et al. |
| 2022/0118106 | A1 | 4/2022 | Bradbury et al. |

FOREIGN PATENT DOCUMENTS

| | | | |
|---|---|---|---|
| WO | WO-2004/108902 | A2 | 12/2004 |
| WO | WO-2006/099445 | A2 | 9/2006 |
| WO | WO-2007/002540 | A2 | 1/2007 |
| WO | WO-2007/136413 | A2 | 11/2007 |
| WO | WO-2007/149062 | A2 | 12/2007 |
| WO | WO-2008/044138 | A1 | 4/2008 |
| WO | WO-2008/142571 | A2 | 11/2008 |
| WO | WO-2009/029870 | A2 | 3/2009 |
| WO | WO-2009/064964 | A2 | 5/2009 |
| WO | WO-2011/003109 | A1 | 1/2011 |
| WO | WO-2011/084620 | A2 | 7/2011 |
| WO | WO-2011/130598 | A1 | 10/2011 |
| WO | WO-2013/087734 | A2 | 6/2013 |
| WO | WO-2013/192609 | A1 | 12/2013 |
| WO | WO-2014/011973 | A2 | 1/2014 |
| WO | WO-2014/145606 | A1 | 9/2014 |
| WO | WO-2015/103420 | A1 | 7/2015 |
| WO | WO-2015/183882 | A1 | 12/2015 |
| WO | WO-2016/015044 | A1 | 1/2016 |
| WO | WO-2016/100340 | A1 | 6/2016 |
| WO | WO-2016/164578 | A1 | 10/2016 |
| WO | WO-2016/196201 | A1 | 12/2016 |
| WO | WO-2017/044701 | A1 | 3/2017 |
| WO | WO-2018/102372 | A1 | 6/2018 |
| WO | WO-2018/191316 | A1 | 10/2018 |
| WO | WO-2018/213851 | A1 | 11/2018 |
| WO | WO-2018/0217528 | A1 | 11/2018 |
| WO | WO-2018/218087 | A1 | 11/2018 |
| WO | WO-2018/237253 | A1 | 12/2018 |
| WO | WO-201 9/113004 | A1 | 6/2019 |

OTHER PUBLICATIONS

International Search Report, PCT/US2018/033098 (Ultrasmall Nanoparticles Labeled With Zirconium-89 and Methods Thereof, filed May 17, 2018), issued by ISA/European Patent Office, 5 pages, dated Aug. 27, 2018.

Ma, K. et al., Control of Ultrasmall Sub-10 nm Ligand-Functionalized Fluorescent Core?Shell Silica Nanoparticle Growth in Water, Chem. Mater., 27:4119?4133, (2015).

Ma, Kai and Wiesner, Ulrich, Modular and Orthogonal Post-PEGylation Surface Modifications by Insertion Enabling Penta-Functional Ultrasmall Organic-Silica Hybrid Nanoparticles, Chem. Mater., 29:6840?6855, (2017).

Suteewong, T. et al., Highly Animated Mesoporous Silica Nanoparticles with Cubic Pore Structure, Journal of American Chemical Society, 133(2):172-175, (2011).

Wilks, M. Q. et al., Imaging PEG-Like Nanoprobes in Tumor, Transient Ischemia, and Inflamatory Disease Models, Bioconjugate Chemistry, 26(6):1061-1069, (2015).

Written Opinion, PCT/US2018/033098 (Ultrasmall Nanoparticles Labeled With Zirconium-89 and Methods Thereof, filed May 17, 2018), issued by ISA/European Patent Office, 9 pages, dated Aug. 27, 2018.

Chen, F. et al., In Vivo Integrity and Biological Fate of Chelator-Free Zirconium-89 Labeled Mesoporous Silica Nanoparticles, ACS Nano, 8(9):7950-7959, (2015).

Schladt, T. D. et al., Multifunctional superparamagnetic $MnO@SiO_2$ core/shell nanoparticles and their application for optical and magnetic resonance imaging, Journal of Materials Chemistry, 22:9253-9262, (2012).

Bai, T. et al., Haloperidol, a sigma receptor 1 antagonist, promotes ferroptosis in hepatocellular carcinoma cells, Biochemical and Biophysical Research Communications, 491(4):919-925, (2017).

Ballou, B. et al., Sentinel Lymph Node Imaging Using Quantum Dots in Mouse Tumor Models, Bioconjugate Chem. 18:389-396 (2007).

Benezra, M. et al., Targeted multimodal silica nanoparticles with efficient urinary excretion for nanomedicine, Cancer Research, 64(7), one page (2009).

Benezra, M. et al., Ultrasmall Integrin-Targeted Silica Nanoparticles Modulate Signaling Events and Cellular Processes in a Concentration-Dependent Manner, Small, 11(14):1721-1732 (2015).

Benezra, M. et. al., Multimodal silica nanoparticles are effective cancer-targeted probes in a model of human melanoma, Journal of Clinical Investigation, 121(7):2768-2780(2011).

Bogush, G. H. et al., Preparation of Monodisperse Silica Particles: Control of Size and Mass Fraction, J. Non-Cryst. Solids, 104:95-106 (1988).

Brien, J. F. et al., A Study of the Calcium Carbimide-Ethanol Interaction in Man, Europ. J. Clin. Pharmacol. 14(2):133-41 (1978).

Brülisauer, L. et al., Disulfide-containing parenteral delivery systems and their redox-biological fate, Journal of Controlled Release, 195:147-154 (2014).

Burns, et al., Fluorescent Silica Nanoparticles with Efficient Urinary Excretion for Nanomedicine, Nano Letters 9(1):442-8 (2009).

Chakraborty, M. et al., External Beam Radiation of Tumors Alters Phenotype of Tumor Cells to Render Them Susceptible to Vaccine-Mediated T-Cell Killing, Cancer Research, 64:4328-4337 (2004).

Cho, Y. S. et al., Cetuximab-conjugated magneto-fluorescent silica nanoparticles for in vivo colon cancer targeting and imaging, Cancer Letters, 299:63-71 (2010).

(56) References Cited

OTHER PUBLICATIONS

Choi, H.S. et. al., Renal clearance of quantum dots, Nature Biotechnology, 25(10):1165-1170, (2007).
Choi, Y. J. et al., Combined inhibition of IGFR enhances the effects of getfitinib in H1650: a lung cancer cell line with EGFR mutation and primary resistance to EGFR-TK inhibitors, Cancer Cehmother Pharmacol, 66:381-388 (2010).
Crespi, M. D. et al., Mitroxantrone Affects Topoisomerase Activities In Human Breast Cancer Cells, Biochemical and Biophysical Research Communications, 136(2):521-8 (1986).
Cressman, S. et al., Binding and Uptake of RGD-Containing Ligands to Cellular $^{\alpha}v^{\beta}3$ Integrins, Int J Pept Res Ther, 15:49-59 (2009).
Cristy, M. and Eckerman, K. F., Specific absorbed fractions of energy at various ages from internal photon sources (I-VII). Oak Ridge National Laboratory Report ORNL/TM-8381N1-7. Springfield, VA: National Technical Information Service, Dept. of Commerce (1987).
Crow, R. T. and Crothers, D. M., Inhibition of Topoisomerase I by Anthracycline Antibiotics: Evidence for General Inhibition of Topoisomerase I by DNA-Binding Agents, J. Med. Chem. 37(19):3191-3194 (1994).
Database Biosis [online] Biosciences Information Service, Von Angerer, E. et al., The Effect of a Combination of Zindoxifene and Cisplatin on Dunning R3327-G Prostatic Carcinomas of the Rat, XP002788768, Database Accession No. PREV199294042193, abstract and Journal of Cancer Research and Clinical Oncology, 118(5):339-343, (1992).
Database Medline [online], US National Library of Medicine (NLM), Urakami, S. et al., Long-term control or possible cure? Treatment of stage D2 prostate cancer under chemotherapy using cisplatin and estramustine phosphate followed by maximal androgen blockade, XP002788770, Database accession No. NLM18092143 abstract & International Urology and Nephrology, 40(2):365-368, (2008).
Database Medline, [online] U.S. National Library of Medicine (NLM), Klump, R. et al., Radiotherapy and concomitant chemoradiotherapy in the NB rat prostate adenocarcinoma model, XP002788769, Database accession No. NLM2519835 abstract, & In Vivo (Athens, Greece), 3(2):109-111, (1989).
De Jong, M. et al., Comparison of $^{111}$In-Labeled Somatostatin Analogues for Tumor Scintigraphy and Radionuclide Therapy, Cancer Res., 58:437-41 (1998).
De Jong, M. et al., Internalization of radiolabelled [DTPA$^0$]octreotide and [DOTA0,Tyr$^3$]ocetreotide:peptides for somatostatin receptor-targeted scintigraphy and radionuclide therapy, Nucl. Med. Common., 19(3):283-288 (1998).
Denny, W. A. and Baguley, B. C., Dual Topoisomerase I/II Inhibitors in Cancer Therapy, Curr. Top. Med. Chem., 3(3):339-353 (2003).
Ding, Y. et al., The performance of thiol-terminated PEG-paclitaxel-conjugated gold nanoparticles, Biomaterials, 34:10217-10227 (2013).
Dixon, S. J. et al., Ferroptosis: An Iron-Dependent Form of Nonapoptotic Cell Death, Cell, 149(51):1060-1072 (2012).
Doronina, S. O. et al., Novel Peptide Linkers for Highly Potent Antibody Auristatin Conjugate, Bioconjugate Chem., 19(10):1960-1963, (2008).
Etrych, T. et al., Biodegradable start HPMA polymer-drug conjugates: Biodegradability, distribution and anti-tumor efficacy, Journal of Controlled Release, 154:241-248 (2011).
European Extended Search Report, Application No. 14763612.0, 10 pages, dated Oct. 19, 2016.
European Extended Search Report, Application No. 17165118.5, 6 pages, dated Jul. 19, 2017.
European Substantive Examination Report, European Application No. 18 752 302.2, 9 pages, dated Dec. 23, 2021.
Foglesong, P. D. et al., Doxorubicin inhibits human DNA topoisomerase I, Cancer Chemother. Pharmacol., 30(2):123-125 (1992).
Frauwirth, K. A. and Thompson, C. B., Activation and inhibition of lymphocytes by costimulation, The Journal of clinical Investigation, 109(3):295-299 (2002).

Fuller, , J. E. et al., Intracellular delivery of core-shell fluorescent silica nanoparticles, Science Direct, Biomaterials, 29:1526-1532 (2008).
Gatto, B. et al., Identification of Topoisomerase I as the Cytotoxic Target of the Protoberberine Alkaloid Coralyne, Cancer Res., 15(12):2795-2800 (1996).
Gerion, D. et al., Enhancement of T1 and T2 relaxation by paramagnetic silica-coated nanocrystals, UCRL-JRNL-224783, 14 pages, (2006).
Gladson, C. A. and Cheresh, D. A., Glioblastoma Expression of Vitronectin and Alpha v Beta 3 Integrin, Adhesion Mechanism for Transformed Glial Cells, J. Clin. Invest. 88:1924-1932(1991).
Guo, Jipeng et al., Ferroptosis: A Novel Anti-tumor Action for Cisplatin, Cancer Research Treatment, 50(2):445-460, (2018).
Herz, E. et al., Fluorescent core-shell silica nanoparticles: an alternative radiative materials platform, Proceedings of SPIE, 6096:609605-1-609605-12, 13 pages, (2006).
Herz, E. et al., Large Stokes-Shift Fluorescent Silica Nanoparticles with Enhanced Emission over Free Dye for Single Excitation Multiplexing, Macromol Rapid Commun., 30(22):1907-1910 (2009).
Hilderbrand, S. A. and Weissleder, R., Near-infrared fluorescence: application to in vivo molecular imaging, Curr. Opin. Chem. Biol., 14:71-9 (2010).
International Search Report, PCT/US2010/040994, dated Aug. 30, 2010.
International Search Report, PCT/US2015/032565, 4 pages, dated Aug. 21, 2015.
International Search Report, PCT/US2016/034351 (Methods of Treatment Using Ultrasmall Nanoparticles to Induce Cell Death of Nutrient-Deprived Cancer Cells Via Ferroptosis, filed May 26, 2016), issued by ISA/EPO, 6 pages, dated Aug. 23, 2016.
International Search Report, PCT/US2018/038973 (Method of Imaging in Vivo Tissues Using Nanoparticles Comprising a Reference Dye and a Sensor Dye, filed Jun. 22, 2018) issued by ISA/European Patent Office, 4 pages, dated Sep. 25, 2018.
International Search Report, PCT/US2018/063751 (Methods of Cancer Treatment Via Regulated Ferroptosis, filed Dec. 4, 2018), issued by ISA/European Patent Office, 13 pages, dated Feb. 20, 2019.
Ito et al., Pharmacokinetics 101, Paediatr Child Health, 16(9):535-536, (2011).
Kalbasi, A. et al., Radiation and immunotherapy: a synergistic combination, Clinical review, The Journal of Clinical Investigation, 127(7):2756-2763 (2013).
Kasukabe, T. et al., Combined treatment with cotylenin A and phenethyl isothiocyanate induces strong antitumor activity mainly through the induction of ferroptotic cell death in human pancreatic cancer cells, Oncology Reports, 36(2):968-976, (2016).
Kim, D. et al., Antitumor activity of sorafenib-incorporated nanoparticles of dextran/poly (dl-lactide-co-glycolide) block copolymer, Nanoscale Research Letters, 7(1):91 (2012).
Kim, S. E. et al., Ultrasmall nanoparticles induce ferroptosis in nutrient-deprived cancer cells and suppress tumour growth, Nature Nanotechnology, 11(11):977-985, (2016).
Kim, S. et al., Near-infrared fluorescent type II quantum dots for sentinel lymph node mapping, Nature Biotechnology 22(1):93-97 (2004).
Kim, Y. H. et al., In situ vaccination against mycosis fungoides by intratumoral injection of a TLR9 agonist combined with radiation: a phase 1/2 study, Blood, 119(2):355-363 (2012).
Klump, R. et al., Radiotherapy and Concomitant Chemoradiotherapy in the NB Rat Prostate Adenocarcinoma Model, in vivo, International Journal of In Vivo Research, 3(2):109-112, (1989).
Koole et al., Paramagnetic lipid-coated silica nanoparticles with a fluorescent quantum dot core: a new contrast agent platform for multimodality imaging, Bioconjugate Chem., 19(12):2471-2479 (2008).
Krenning, E. P. et al, Somatostatin Receptor Scintigraphy with Indium-111-DTPA-D-Phe-1-Octreolide in Man: Metabolism, Dosimetry and Comparison with Iodine-123-Tyr-3-Octreotide, J Nucl. Med. 33:652-8 (1992).

(56) References Cited

OTHER PUBLICATIONS

Lachaier, E. et al., Sorafenib Induces Ferroptosis in Human Cancer Cell Lines Originating from Different Solid Tumors, Anticancer Research, 34:6417-6422 (2014).

Larson, D. R. et al., Silica Nanoparticle Architecture Determines Radiative Properties of Encapsulated Fluorophores, Chem. Mater. 20:2677-2684 (2008).

Lee. G. Y. et al., Theranostic Nanoparticles with Controlled Release of Gemcitabine for Targeted Therapy and MRI of Pancreatic Cancer, ACS NANO, 7(3):2078-2089, (2013).

Lewis et al. Comparison of Four 64Cu-labeled Somatostatin Analogs in Vitro and in a Tumor-Bearing Rat Model: Evaluation of New Derivatives for Positron Emission Imaging and Targeted Radiotherapy. J Med Chem., 42:1341-7 (1999).

Lin et al., In Vitro Toxicity of Silica Nanoparticles in Human Lung Cancer Cells, Toxicology and Applied Pharmacology, 217:252-259, (2006).

Li, T. et al., Human Topoisomerase I Poisoning by Protoberberines: Potential Roles for Both Drug-DNA and Drug-Enzyme Interactions, Biochemistry, 39(24):7107-7116 (2000).

Li, Z. et al., $^{64}$Cu-labeled Tetrameric and Octomeric RGD Peptides for Small-Animal PET of Tumor $\alpha_v\beta_3$ Integrin Expression, J. Nucl Med. 48:1162-1171 (2007).

Loir, B. et al., Expression of the MC1 Receptor Gene in Normal and Malignant Human Melanocytes. A Semiquantitative RT-PCR Study, Cell Mol. Biol., 45(7):1083-1092 (1999).

Lu, J. et al., Biocompatibility, Biodistribution, and Drug-Delivery Efficiency of Mesoporous Silica Nanoparticles for Cancer Therapy in Animals, Small, 6(16):1794-1805, (2010).

Ma, K. et al., Control of Ultrasmall Sub-10 nm Ligand-Functionalized Fluorescent Core-Shell Silica Nanoparticle Growth in Water, Chemistry of Materials, 27:4119-4133, (2015).

Ma, S. et al., Ferroptosis and autophagy induced cell death occur independently after siramesine and lapatinib treatment in breast cancer cells, Plos One, 12(8):e0182921, 14 pages, (2017).

Ma, S. et al., Ferroptosis is induced following siramesine and lapatinib treatment in breast cancer cells, Cell Death and Disease, 7(7):e2307, 11 pages, (2016).

Makhey et al., Sbustitute Benzo[i]phenanthridines as Mammalian Topoisomerase-Targeting Agents, Bioorg. Med. Chem. 11(8):1809-1820 (2003).

Mayer, R. J. et al., Randomized Trial of TAS-102 for Refractory Metastatic Colorectal Cancer, NEJM, 372(20):1909-1919 (2015).

McKeage et al., Phase I and Pharmacokinetic Study of an Oral Platinum Complex Given Daily for 5 Days in Patients With Cancer, Journal of Clinical Oncology, 15(7):2691-2700 (1997).

Montet, X. et al., Multivalent Effects of RGD Peptides Obtained by Nanoparticle Display, J. Med. Chem. 49:6087-6093 (2006).

Mulder, W.J.M. et al., Quantum Dots with a Paramagnetic Coating as a Bimodal Molecular Imaging Probe, Nano Letters, 6(1):1-6, (2006).

Nunes, Jessica J. et al., Targeting NF-kappa B Signaling by Artesunate Restores Sensitivity of Castrate-Resistant Prostate Cancer Cells to Antiandrogens, Neoplasia, 19(4):333-345, (2017).

Núñez, N. P. et al., PPAR-γ Ligands and Amino Acid Deprivation Promote Apoptosis of Melanoma, Prostate, and Breast Cancer Cells, Cancer Letters, 236:133-141, (2006).

Ohnishi, S. et al., Organic Alternatives to Quantum Dots for Intraoperative Near-Infrared Fluorescent Sentinel Lymph Node Mapping, Molecular Imaging 4(3):172-181 (2005).

Ow, H. et al., Bright and Stable Core-Shell Fluorescent Silica Nanoparticles, Nano Letters, 5(1):113-117 (2005).

Papamicheal, D., The Use of Thymidylate Synthase Inhibitors in the Treatment of Advanced Colorectal Cancer: Current Status, The Oncologist, 4:478-487 (1999).

Patel, K. N. et al., MUC1 plays a role in tumor maintenance in aggressive thryroid carcinomas, Surgery 138(6):994-1002 (2005).

Phillips, E. et al., Clinical translation of an ultrasmall inorganic optical-PET imagine nanoparticle probe, www.ScienceTranslationMedicine.org, 6(26):26ra149:1-9, plus Editor's Summary—2 pages, (2014).

Phillips, E. et al., Clinical translation of an ultrasmall inorganic optical-PET imaging nanoparticle probe, Science Translational Medicine, 6(260):260ra149-260ra149 (2014).

Piatyszek, M.A. et al., Iodo-Gen-Mediated Radioiodination of Nucleic Acids, J. Anal. Biochem. 172(2):356-359 (1988).

Pommier, Y., Topoisomerase I inhibitors: camptothecins and beyond, Nat. Rev. Cancer, 6(10):789-802 (2006).

Prosecution File History of Chinese Application 201080039307.2 as of Oct. 5, 2016, 54 pages.

Prosecution File History of European Application No. 10 794 842.4 as of Jul. 29, 2016, 30 pages.

Ren. G. et al., PET of Malignant Melanoma Using $^{18}$F-Labeled Metallopeptides, The Journal of Nuclear Medicine, 50(11):1865-1872 (2009).

Reubi, J.C. et al., Distribution of Somatostatin Receptors in Normal and Tumor Tissue, Metabolism, 39(9)(2):78-81 (1990).

Reubi, J.C. et al., Somatostatin Receptors and Their Subtypes in Human Tumors and in Peritumoral Vessels, Metabolism, 45(8)(1):39-41 (1996).

Rianasari, I. et al., Covalent Coupling of Nanoparticles with Low-Density Functional Ligands to Surface via Click Chemistry, Int. J. Mol. Sci. 14:3705-3717 (2013).

Ruoslahti, E. and Pierschbacher, M. D., New Perspectives in Cell Adhesion: RGD and Integrins, Science 238:491 (1987).

Sadasivan, et al., Alcoholic Solvent Effect on Silica Synthesis—NMR and DLS Investigation, J. Sol-Gel Science and Technology, 12:5-14 (1998).

Safenoka, I. V. et al., Correlation between the composition of multivalent antibody conjugates with colloidal gold nanoparticles and their affinity, Journal of Immunological Methods, 357:17-25, (2010).

Sanderson, R. J. et al., In vivo Drug-Linker Stability of an Anti-CD30 Dipeptide-Linked Auristatin Immunoconjugate, Clinical cancer Research, 11:843-852 (2005).

Sato, M. et al., The ferroptosis inducer erastin irreversibly inhibits systems $x_c^-$—and synergizes with cisplatin to increase cisplatin's cytotoxicity in cancer cells, Scientific Reports, 8(1):968, 9 pages, (2018).

Seftor, R. E. B. et al., Role of the alpha v beta 3 integrin in human melanoma cell invasion, Proc. Natl. Acad. Sci., 89:1557-1561 (1992).

Sehm, T. et al., Temozolomide toxicity operated in a xCT/SLC7a11 dependent manner and is fostereed by ferroptosis, Oncotarget, 7(46):74630-74647, (2016).

Seung, S. K. et al., Phase 1 Study of Stereotactic Body Radiotherapy and Interleukin-2: Tumor and Immunological Responses, Science Trnslational Medicine 14(137):137ra74 1-7 (2012).

Seymour, L.W., Passive Tumor Targeting of Soluble Macromolecules and Drug Conjugates, Critical Reviews in Therapeutic Drug Carrier Systems, 9(2):135-187 (1992).

Sharma, P. et al. Nanoparticles of bioimaging, Advances in Colloid and Interface Science, 123-126:471-485 (2006).

Slowing, I.I. et al., Mesoporous silica nanoparticles as controlled release drug delivery and gene transfection carriers, Advanced Drug Delivery Reviews, 60:1278-1288 (2008).

Soster, M. et al., Targeted dual-color silica nanoparticles provide univocal identification of micrometastases in preclinical models of colorectal cancer, International Journal of Nanomedicine, 7:4797-4807 (2012).

Stabin, M. G. et al., OLINDA/EXM: The Second-Generation Personal Computer Software for Internal Dose Assessment in Nuclear Medicine, J Nucl Med. 46:1023-1027 (2005).

Takeshima, T. et al., Local Radiation Therapy Inhibits Tumor Growth through the Generation of Tumor-Specific CTL: Its Potentiation by Combination with Th1 Cell Therapy, Cancer Research, 70(7):2697-2706 (2010).

(56) References Cited

OTHER PUBLICATIONS

Takezawa, K. et al, Sorafenib Inhibits Non-Small Cell Lung Cancer Cell Growth by Targeting B-RAF in KRAS Wild-Type Cells and C-RAF in KRAS Mutant Cells, Cancer Res, 69(16):6515-6521 (2009).
Tanaka, E. et al, Image-Guided Oncologic Surgery Using Invisible Light: Completed Pre-Clinical Development for Sentinel Lymph Node Mapping, Annals of Surgical Oncology 13(12):1671-1681 (2006).
Tavernaro, I. et al., Bright Fluorescent silica-nanoparticle probes for high-resolution STED and confocal microscopy, Beilstein Journal of Nanotechnology, 8:1283-1296, (2017).
Thakor, A. S. and Gambhir. S. S., Nanooncology: The Future of Cancer Diagnosis and Therapy, CA Cancer J. Clin., 63(6):395-418 (2013).
Topalian, S. L. et al., Safety, Activity, and Immune Correlates of Anti-PD-1 Antibody in Cancer, The New England Journal of Medicine, 366(26):2443-2454 (2012).
Urakami, S. et al., Long-term control or possible cure? Treatment of stage D2 prostate cancer under chemotherapy using cisplatin and estramustine phosphate followed by maximal androgen blockade, Int. Urol. Nephol., 40:365-368, (2008).
Van Schooneveld, M. M. et al., Improved Biocompatibility and Pharmacokinetics of Silica Nanoparticles by Means of a Lipid Coating: A Multimodality Investigation, Nano Letters, 8(8):2517-2525 (2008).
Vejayakumaran, P. et al., Structural and thermal characterizations of silica nanoparticles grafted with pendant maleimide and epoxide grops, Journal of Colloid and Interface Science, 328:81-91 (2008).
Von Angerer, E. et al., The effect of a combination of zindoxifene and cisplatin on Dunning R3327-G prostatic carcinomas of the rat, Cancer Research Clinical Oncology, 118:339-343, (1992).
Wang, X. et al., Folate Receptor-Targeted Aggregation-Enhanced Near-IR Emitting Silica Nanoprobe for One-Photon in Vivo and Two-Photon ex Vivo FLuorescence Bioimaging, Bioconjugate Chemistry, 22:1438-1450 (2011).
Wang, Y. et al., Tumor cell targeted delivery by specific peptide-modified mesoporous silica nanoparticles, J. Mater. Chem., 22:14608-14616, (2012).
Webb, et al., Sphingomyelin-cholesterol liposomes significantly enhance the pharmacokinetic and therapeutic properties of vincristine in murine and human tumour models, British J. of Cancer 72:896-904 (1995).
Webster, A. et al., Optical calcium sensors: development of a generic method for their introduction to the cell using conjugated cell penetrating peptides, Analyst, 130:163-70 (2005).
Wersäll, P.J. et al., Regression of non-irradiated metastases after extracranial stereotactic radiotherapy in metastatic renal cell carcinoma, Acta Oncologica, 45:493-497 (2006).
Written Opinion, PCT/US2010/040994, dated Aug. 30, 2010.
Written Opinion, PCT/US2015/032565, 6 pages, dated Aug. 21, 2015.
Written Opinion, PCT/US2016/034351 (Methods of Treatment Using Ultrasmall Nanoparticles to Induce Cell Death of Nutrient-Deprived Cancer Cells Via Ferroptosis, filed May 26, 2016), issued by ISA/EPO, 9 pages, dated Aug. 23, 2016.
Written Opinion, PCT/US2018/038973 (Method of Imaging in Vivo Tissues Using Nanoparticles Comprising a Reference Dye and a Sensor Dye, filed Jun. 22, 2018) issued by ISA/European Patent Office, 7 pages, dated Sep. 25, 2018.
Written Opinion, PCT/US2018/063751 (Methods of Cancer Treatment Via Regulated Ferroptosis, filed Dec. 4, 2018), issued by ISA/European Patent Office, 11 pages, dated Feb. 20, 2019.
Wu, P. et al., Imaging Breast Cancer Cells and Tissues Using Peptide-Labeled Fluorescent Silica Nanoparticles, Journal of Nanoscience and Nanotechnology, 8(5):2483-2487 (2008).
Xia, T. et al., Polyethyleneimine Coating Enhances the Cellular Uptake of Mesoporous Silica Nanoparticles and Allows Safe Delivery of siRNA and DNA Constructs, ACS Nano, 3(10):3273-3286, (2009).
Xie, Y. et al., Ferroptosis: process and function, Cell Death and Differentiation, 23(3):369-379, (2016).
Xu, Z. et al., DNA Minor Groove Biding-Directed Poisoning of Human DNA Topoisomerase I by Terbenzimidazoles, Biochemistry 37(10):3558-3566 (1998).
Yamaguchi, Y. et al., Piperlongumine rapidly induces the death of human pancreatic cancer cells mainly through the induction of ferroptosis, International Journal of Oncology, 52:1011-1022, (2018).
Yoo, B. et al., Expanding Analytical Tools for Characterizing Ultrasmall Silica-based Nanoparticles, HHS Public Access, RSC Adv., 7(27):16861-16865, pp. 1-13, (2017).
Yu, Y. et al., The ferroptosis inducer erastin enhances sensitivity of acute myeloid leukemia cells to chemotherapeutic agents, Molecular & Cellular Oncology. 2(4):e1054549-1-e1054549-7, (2015).
Zeng, J. et al., Anti-PD-1 Blockade and Stereotactic Radiation Produce Long-Term Survival in Mice With Intracranial Gliomas, Intl. J. Radiation Oncol. Biol. Phys., 86(2):343-349 (2013).
Zhang, et al., Copper-62 labeled ReCCMSH peptide analogs for melanoma PET imaging, Curr Radiopharm, 5(4):329-335 (2012) (ABSTRACT only attached).
Zhang, X. L. et al., Ultrasmall 1-6, radioiodinated alpha MSH-C dots for melanoma imaging and therapy, Journal of Labelled Compounds and Radiopharmeceuticals, 58(1):5114 (2015).
Zhen, C. et al., Radioiodination of Rhenium Cyclized α-Melanocyte-Stimulating Hormone Resulting in Enhanced Radioactivity Localization and Retention in Melanoma, Cancer Research, 64:1411-1418, (2004).
Zhong, Y. J. et al., Cathepsin B-cleavable doxorubicin prodrugs for targeted cancer therapy (Review), International Journal of Oncology, 42:373-383, (2013).

* cited by examiner

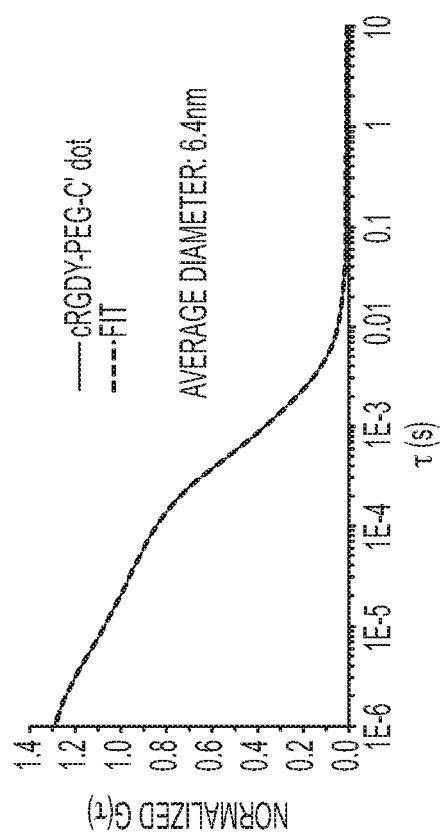
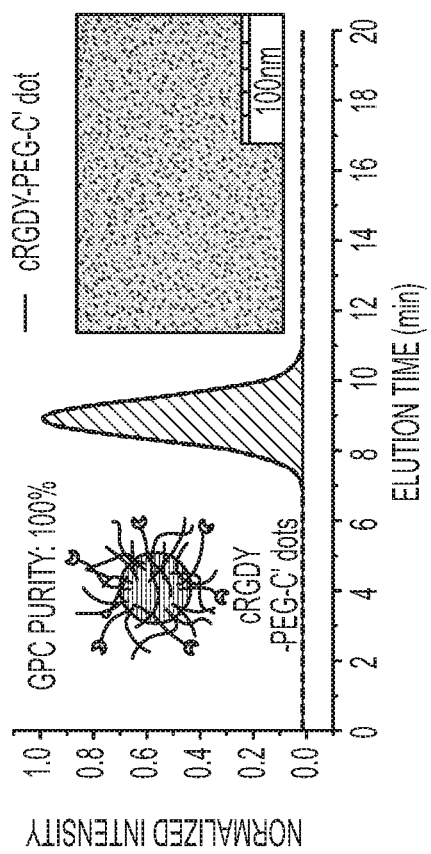
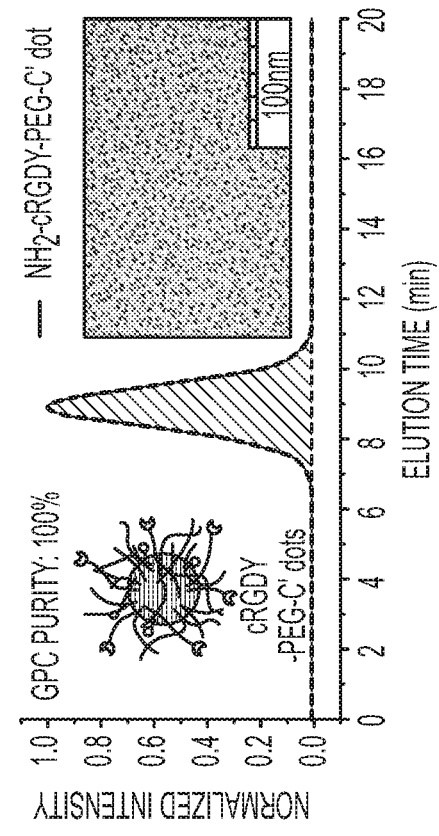
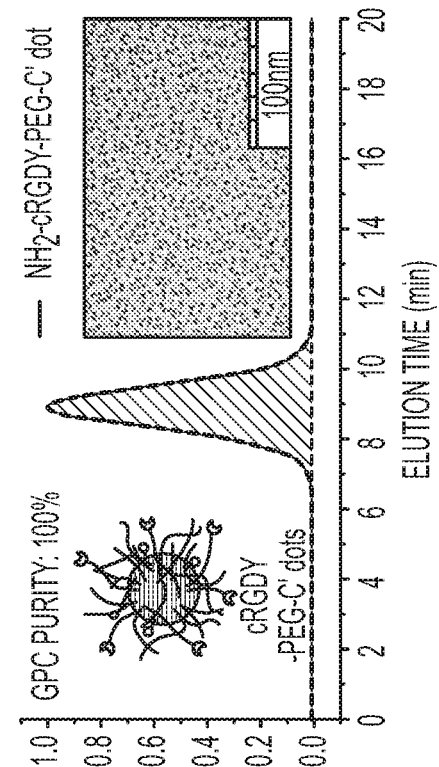
FIG. 1A
FIG. 1B
FIG. 1C
FIG. 1D

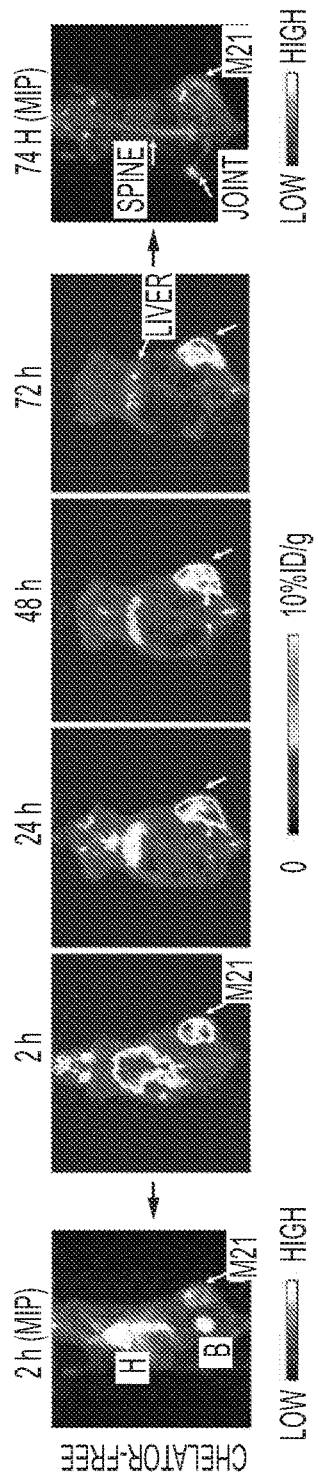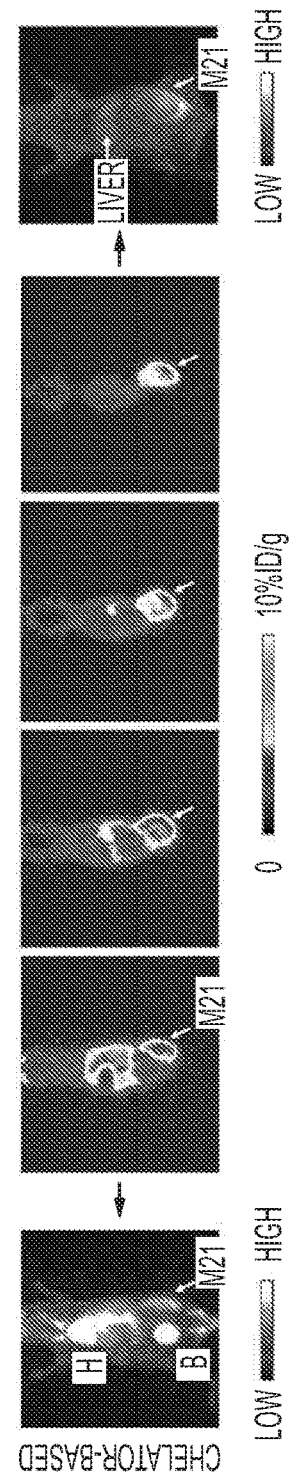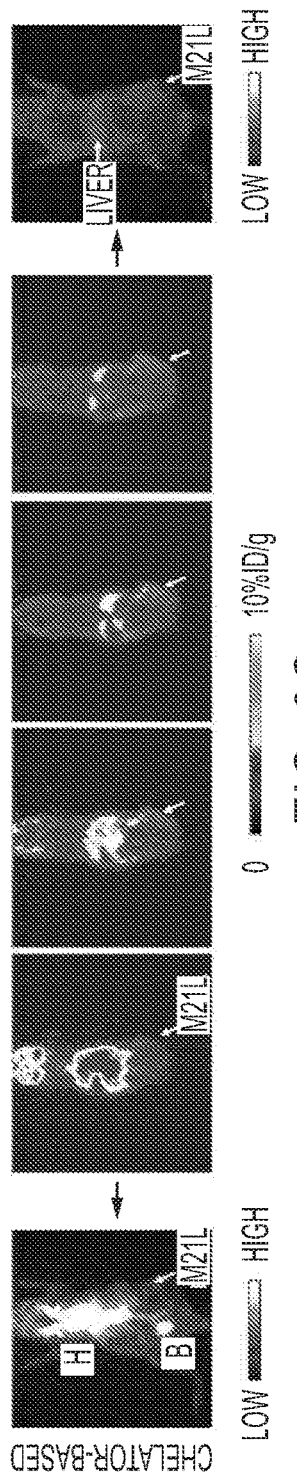

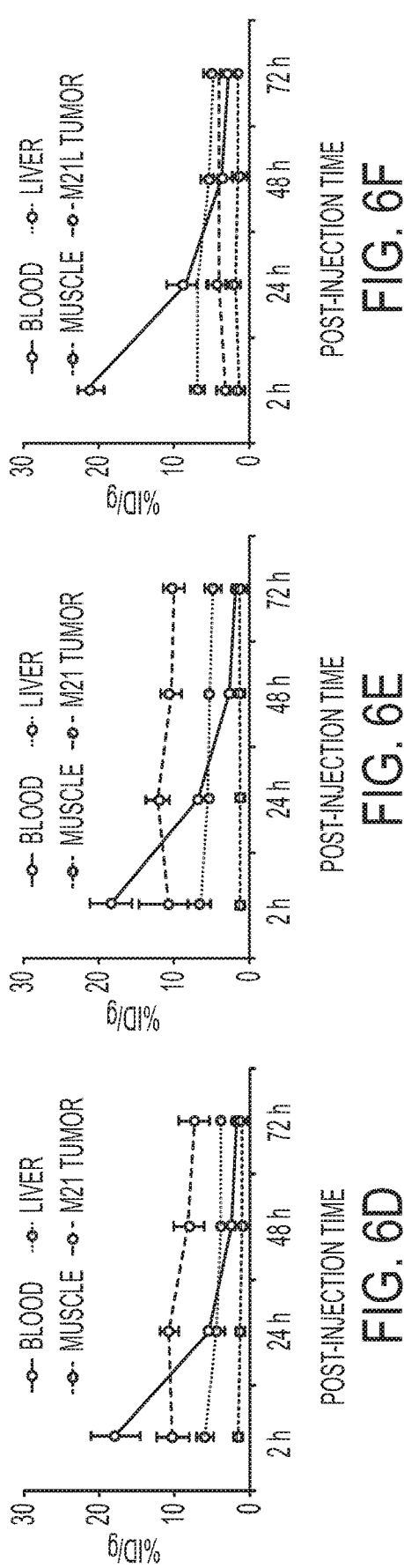
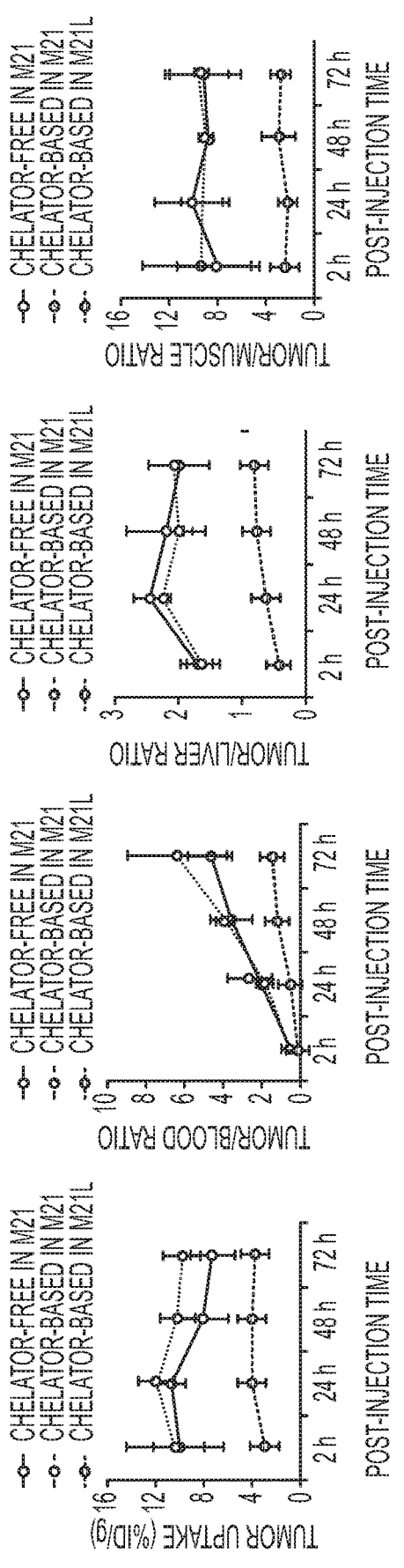

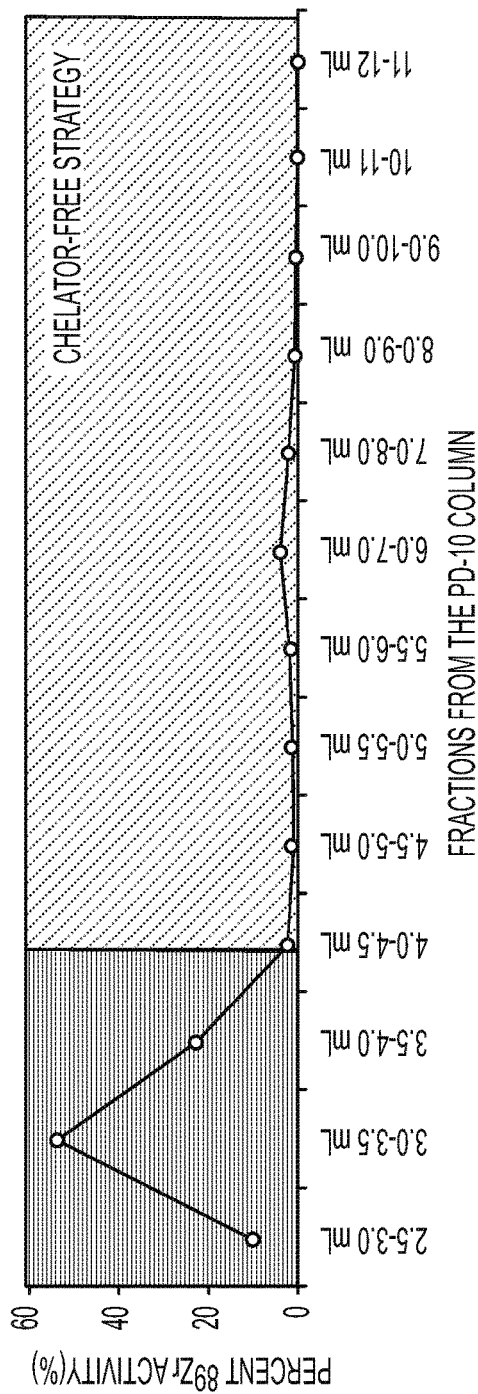
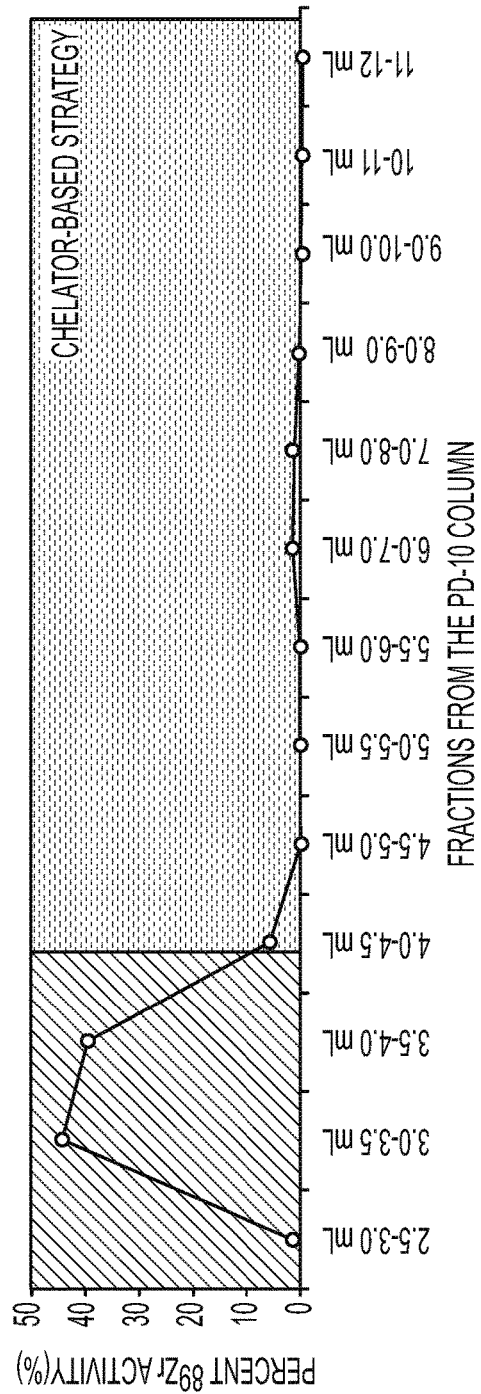
FIG. 9A
FIG. 9B

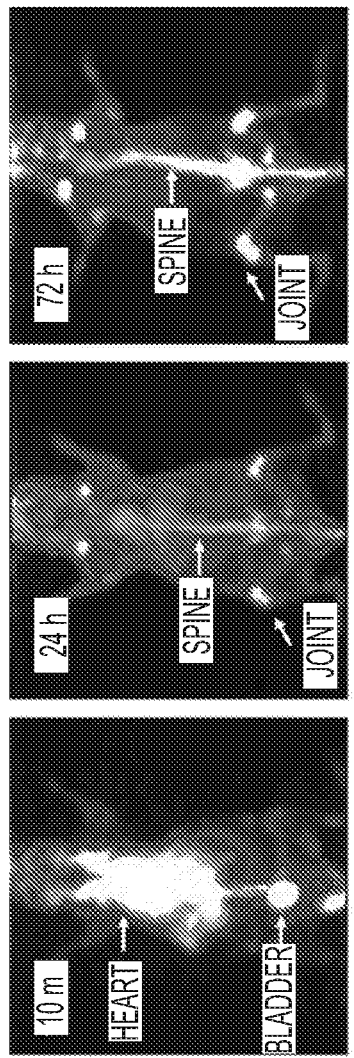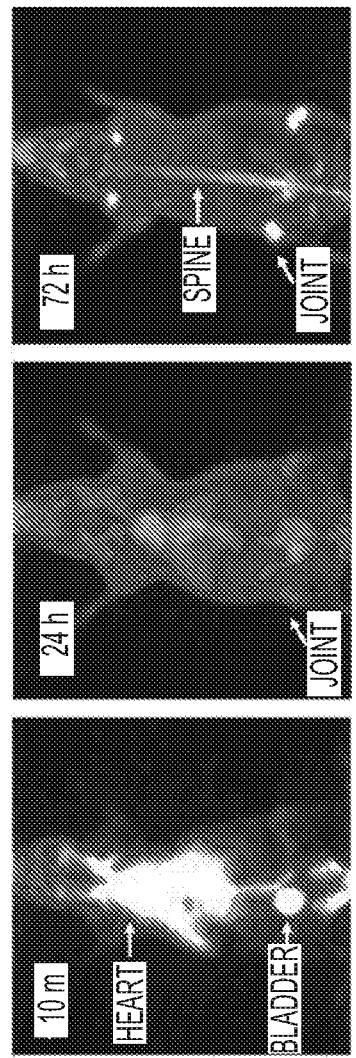
FIG. 12A
FIG. 12B

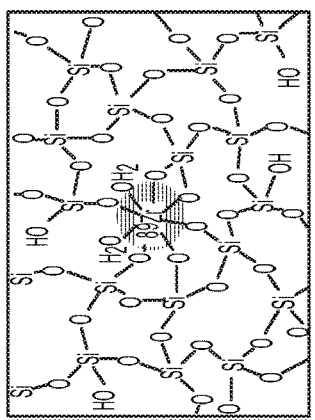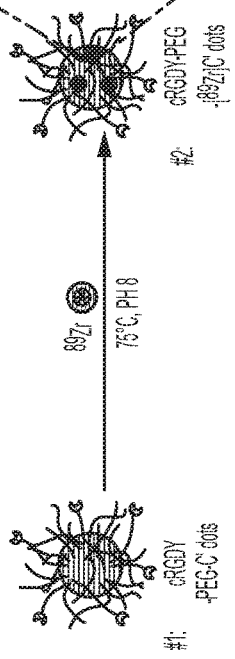
FIG. 16A
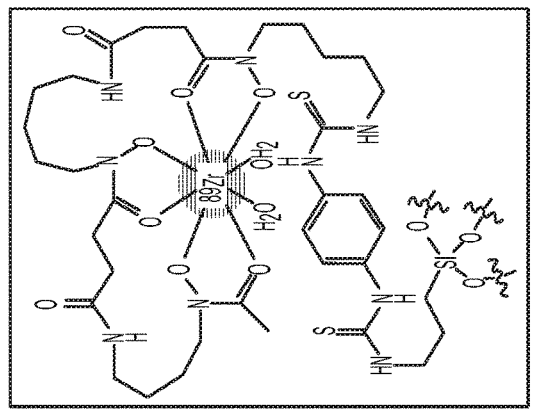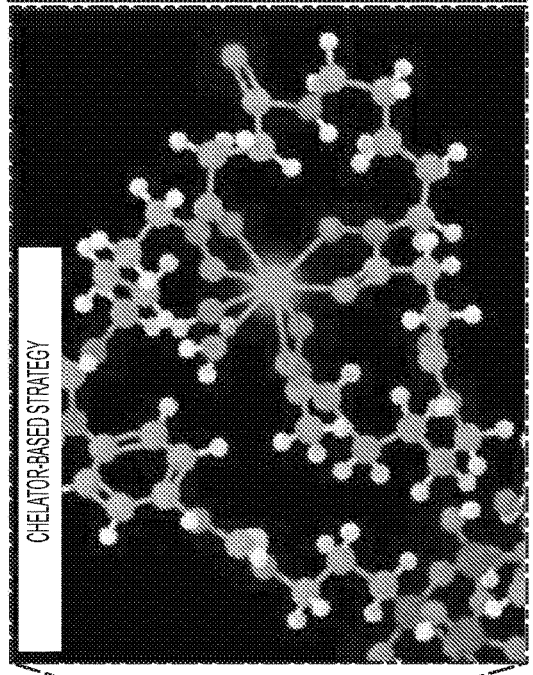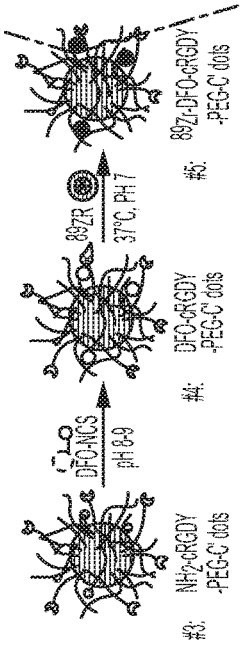
FIG. 16B

ULTRASMALL NANOPARTICLES LABELED WITH ZIRCONIUM-89 AND METHODS THEREOF

CROSS-REFERENCE TO RELATED APPLICATION

This application claims the benefit of U.S. Application Ser. No. 62/510,859 filed on May 25, 2017, the disclosure of which is hereby incorporated by reference in its entirety.

GOVERNMENT FUNDING

This invention was made with government support under grant numbers CA161280 and CA199081 awarded by the National Institutes of Health. The government has certain rights in this invention.

FIELD OF THE INVENTION

This invention relates generally to nanoprobes (e.g., under 20 nanometers in diameter) comprising a nanoparticle, radiolabel, and targeting agent (e.g., an antibody, e.g., a targeting ligand), useful, for example, for the detection, prevention, and/or treatment of cancer and other diseases.

BACKGROUND

A "target-or-clear" multi-functional nanoplatform that actively localizes to a target-of-interest after systematic administration and maintains a low non-specific accumulation in the reticuloendothelial system (RES) has long been one of the major challenges in the field nanomedicine.

Over three decades, despite preclinical research results of various types of solid (or inorganic-based) nanomaterials in small animals, only very few of these nanomaterials have progressed to first-in-human clinical trials. Challenges in nanoparticle manufacturing, regulatory obstacles, rapidly rising clinical trial costs, increasing complexity of trial designs, limited in vivo active targeting efficacy, and high liver accumulation rates (i.e., 30-99% of administered particles from the bloodstream) are examples of major hurdles that most of the existing nanomaterials need to address. For nanomaterials with a hydrodynamic (HD) size larger than 10 nm, even with the protection of stealth polymers (e.g., polyethylene glycol [PEG]) and functionalized with tumor homing ligands (e.g., peptides or antibodies), it is still quite common to see predominant reticuloendothelial system (RES) (i.e., liver and spleen) uptake, tumor-to-liver activity concentration ratios less than 1, and relatively low tumor-to-background (e.g., blood or muscle) ratios. High RES uptake also raises the long-term in vivo toxicity concerns due to extremely slow and generally unpredictable hepatobiliary clearance rates from the liver, with resulting delays in obtaining Investigational New Drug (IND) approval from the US Food and Drug Administration (FDA).

Examples of properties needed for nanomedicines include 1) easy manufacturing process with a low cost, 2) high active targeting efficacy to the disease (e.g., cancer) site with low off-targeting rate (e.g., low non-specific uptake in RES or other healthy organs), 3) suitable (and tunable) blood circulation half-life to ensure the sufficient accumulation of nanomedicine in cancer for diagnosis or treatment purpose, 4) dominant renal clearance to grantee a favorable safety profile, 5) whole body non-invasive tracking via clinical-relevant imaging technique(s) (e.g., positron emission tomography [PET], single-photon emission computed tomography [SPECT], magnetic resonance imaging (MRI), computed tomography [CT] and optical imaging), and 6) specific delivery of sufficient therapeutic agents (e.g., small molecular drugs, singlet oxygen, inhibitors, radiation, heat) to the cancer cells for treatment.

Although greater than 10 nm sized solid nanomaterials hold the advantage of significantly enhanced drug-loading capacity relative to their sub-10 nm sized counterparts, clinical translation of such materials can still be hindered by low tumor targeting efficacy and high off-targets (e.g., liver accumulations associated with dose-limited toxicity).

Fast renal clearance, relatively short blood circulation half-times (ranging from several minutes to several hours) and low RES uptake (on the order of 5% ID/g or less) represent defining biological features for ultrasmall (sub-10 nm) renally clearable nanoparticles. Although suitable PEGylation techniques have been developed to improve blood circulation half-times (up to >10 h) of such platforms, the ability to precisely control physiochemical properties, including surface ligand number, in a manner that facilitates bulk renal clearance while preservating active tumor targeting capabilities has long posed a significant challenge to the field.

There remains a need for a platform that can be used for the detection, prevention, and/or treatment of cancer and other diseases.

SUMMARY

Described herein are nanoprobes created from ultrasmall aminated nanoparticles by attaching a targeting ligand and a radiolabel [e.g., Zirconium-89 ($^{89}$Zr)], as well as methods of their use. The provided compositions are renally clearable and possess suitable blood circulation half-life, high tumor active targeting capability, dominant renal clearance, low liver accumulation, and a high tumor-to-background ratio. The described nanoprobes exhibit great potential as "target-or-clear" tracers to human subjects for systemic targeted imaging (or treatment) of cancer.

In particular, the present disclosure describes how the biological properties of the nanoparticles are influenced by the conjugation of radiometals, such as zirconium-89 ($^{89}$Zr, $t_{1/2}$=78.4 h), using various radiolabeling strategies. For example, attachment of $^{89}$Zr to surface-aminated, integrin-targeting ultrasmall nanoparticles (e.g., C' dots) led to favorable PK and clearance profiles, as well as significant improvements in targeted tumor uptake and target-to-background ratios in melanoma models relative to biological controls while maintaining particle sizes below the effective renal glomerular filtration size cutoff (<10 nm). Nanoprobes developed using the radiolabeling strategies were characterized in terms of their radiostability and plasma residence half-times. The described nanoprobes offer radiobiological properties suitable for enhanced molecularly-targeted cancer imaging in humans.

It is found that even with the reduced silanol density of such a small silica-based nanoparticle with its concomitant radius of curvature, and with a reduced number of available functional groups on the surface, it is possible to attach radiolabels and targeting ligands to produce the observed properties, such that the nanoparticle can be used for diagnostic and/or therapeutic applications. It is found that chelator-free labeling can be achieved, even with such small nanoparticles.

In one aspect, the invention is directed to a nanoprobe (e.g., radioconjugate, e.g., nanoconjugate) created from an aminated nanoparticle, the nanoprobe comprising: a nanoparticle (e.g., an ultrasmall nanoparticle, e.g., a silica-based nanoparticle, e.g., a C' dot (e.g., $NH_2$-cRGDY-PEG-C' dot)); a targeting agent (e.g., an antibody fragment, e.g., a targeting peptide (e.g., cRGD or an analog thereof), e.g., a small protein (e.g., $VEGF_{121}$)) conjugated to the nanoparticle (e.g., directly or indirectly); and a radiolabel, wherein the nanoparticle is amine-functionalized prior to conjugation or association with the targeting agent and/or the radiolabel, and wherein the nanoparticle has a diameter (e.g., average diameter) no greater than 20 nanometers (e.g., as measured by dynamic light scattering (DLS) in aqueous solution, e.g., saline solution) (e.g., wherein the average nanoparticle diameter is from 1 to 20 nm, e.g., from 1 to 15 nm, e.g., from 1 to 10 nm, e.g., from 1 to 8 nm, e.g., from 4 to 10 nm, e.g., from 4 to 8 nm) (e.g., wherein the nanoprobe has an average diameter no greater than 50 nm, e.g., no greater than 40 nm, e.g., no greater than 30 nm, e.g., no greater than 20 nm, e.g., no greater than 15 nm, e.g., no greater than 10 nm).

In certain embodiments, the nanoparticle comprises an ultrasmall nanoparticle.

In certain embodiments, the radiolabel comprises $^{89}$Zr. In certain embodiments, the radiolabel is associated with the nanoparticle (e.g., covalently or non-covalently bonded to the nanoparticle via a linker or covalently or non-covalently bonded directly to the nanoparticle, or associated with the nanoparticle or a composition surrounding the nanoparticle, e.g., via van der Waals forces) (e.g., without a chelator (e.g., wherein the nanoprobe is chelator-free)) (e.g., with a chelator)).

In certain embodiments, the targeting agent is covalently or non-covalently bonded to the nanoparticle via a linker or covalently or non-covalently bonded directly to the nanoparticle, or associated with the nanoparticle or a composition surrounding the nanoparticle, e.g., via van der Waals forces.

In certain embodiments, the nanoparticle is coated with an organic polymer. In certain embodiments, the organic polymer comprises polyethylene glycol (PEG).

In certain embodiments, the targeting agent comprises a targeting peptide (e.g., RGD, e.g., cRGD, e.g., an analog of RGD, e.g., alphaMSH, e.g., any peptide known to be immunomodulatory and anti-inflammatory in nature). In certain embodiments, the targeting peptide comprises a member selected from the group consisting of arginylglycylaspartic acid (RGD), cyclic arginylglycylaspartic acid (cRGD), an analog of RGD, alpha-Melanocyte-stimulating hormone (alphaMSH), and any peptide known to be immunomodulatory and anti-inflammatory in nature. In certain embodiments, the targeting agent comprises an antibody fragment, and wherein the antibody fragment is in a range from about 5 kDa to about 25 kDa (e.g., from about 10 kDa to about 20 kDa, e.g., about 15 kDa) (e.g., wherein the antibody fragment comprises a functional single domain antibody fragment). In certain embodiments, the targeting agent comprises an antibody fragment, and wherein the antibody fragment is from about 20 kDa to about 45 kDa (e.g., from about 25 kDa to about 30 kDa) (e.g., wherein the antibody fragment comprises a functional single chain antibody fragment). In certain embodiments, the targeting agent comprises an antibody fragment, and wherein the antibody fragment is from about 40 kDa to about 80 kDa (e.g., from about 50 kDa to about 70 kDa, e.g., about 60 kDa) (e.g., wherein the antibody fragment comprises a functional fab fragment).

In certain embodiments, the nanoparticle comprises silica. In certain embodiments, the nanoparticle comprises a silica-based core and a silica shell surrounding at least a portion of the core. In certain embodiments, the nanoparticle comprises a fluorescent compound within the core (e.g., Cy5).

In certain embodiments, the targeting agent comprises a small protein, and wherein the small protein comprises $VEGF_{121}$.

In certain embodiments, the targeting agent comprises an antibody fragment, and wherein the antibody fragment is a member selected from the set consisting of a recombinant antibody fragment (fAbs), a single chain variable fragment (scFv), and a single domain antibody (sdAb) fragment. In certain embodiments, the targeting agent comprises an antibody fragment, and wherein the antibody fragment is a single chain variable fragment (scFv). In certain embodiments, the targeting agent comprises an antibody fragment, and wherein the antibody fragment is a single domain (sdAb) fragment.

In certain embodiments, the nanoparticle (a single nanoparticle) has from one to ten targeting agents (e.g., wherein a group of nanoparticles of a particular species has an average number of targeting agents per nanoparticle within a range from 1 to 8, e.g., from 1 to 7, e.g., from 1 to 5, e.g., from 1 to 4, e.g., from 1 to 3, e.g., from 1 to 2) attached thereto (e.g., wherein the number of targeting agents per nanoparticle is selected depending on the size of the antibody fragment, e.g., so that the nanoprobe can be renally cleared, e.g., wherein the nanoprobe is a diagnostic, e.g., and/or wherein the number of targeting agents per nanoparticle is selected depending on the number of antibody fragments capable of being attached to the nanoparticle and/or so that the nanoprobe is not renally cleared (or so that renal clearance is inhibited), e.g., wherein the nanoprobe is a theranostic or therapeutic).

In certain embodiments, the targeting agent is conjugated to the nanoparticle via a PEG moiety.

In certain embodiments, the nanoparticle has a diameter (e.g., average diameter) no greater than 15 nanometers (e.g., no greater than 13 nanometers, e.g., no greater than 10 nanometers). In certain embodiments, the nanoparticle has a diameter (e.g., average diameter) in a range from 1 nm to 20 nm (e.g., from 2 nm to 15 nm, e.g., from 5 nm to 15 nm, e.g., from 1 nm to 10 nm, e.g., from 2 nm to 10 nm, e.g., from 5 nm to 10 nm).

In certain embodiments, the targeting agent comprises a member selected from the set consisting of anti-CEA scFv, anti-GPIIb/IIIa, anti-VEGF-A, anti-VEGF-R, and anti-TNF-α (e.g., PEGylated).

In certain embodiments, the nanoprobe comprises one or more imaging agents (e.g., within the nanoparticle, attached to the nanoparticle, and/or attached to the targeting agent). In certain embodiments, the one or more imaging agents comprise a PET or SPECT tracer. In certain embodiments, the PET or SPECT tracer comprises a member selected from the group consisting of $^{89}$Zr, $^{64}$Cu, [$^{18}$F] fluorodeoxyglucose, $^{177}$Lu, $^{225}$At, and $^{90}$Y. In certain embodiments, the one or more imaging agents comprise a fluorophore (e.g., a cyanine).

In certain embodiments, the nanoprobe comprises a therapeutic agent (e.g., wherein the therapeutic agent is attached to the nanoparticle, or to the targeting agent, or to both the nanoparticle and the targeting agent, e.g., wherein the attachment is covalent or non-covalent). In certain embodiments, the therapeutic agent comprises a chemotherapy drug. In certain embodiments, the chemotherapy drug comprises a member selected from the group consisting of sorafenib, paclitaxel, docetaxel, MEK162, etoposide, lapatinib, nilotinib, crizotinib, fulvestrant, vemurafenib, bexorotene, and/or camptotecin. In certain embodiments, the therapeutic agent comprises a checkpoint inhibitor (e.g., wherein the class and/or species of checkpoint inhibitor is selected based on changes in the microenvironment, e.g., wherein the changes are caused by administration of a first therapeutic) (e.g., for combination therapy, e.g., for radiotherapy) (e.g., wherein such changes are determined via mapping immune cell profiles).

In certain embodiments, the chelator comprises desferoxamine (DFO). In certain embodiments, the chelator comprises a member selected from the group consisting of 1,4,8,1 1-tetraazabicyclo[6.6.2]hexadecane-4, 1 1-diyl)diacetic acid (CB-TE2A); desferoxamine (DFO); diethylenetriaminepentaacetic acid (DTPA); 1,4,7,10-tetraazacyclotetradecane-1,4,7,10-tetraacetic acid (DOTA); thylenediaminetetraacetic acid (EDTA); ethylene glycolbis (2-aminoethyl)-N,N,N',N'-tetraacetic acid (EGTA); 1,4,8,1 1-tetraazacyclotetradecane-1,4,8,1 1-tetraacetic acid (TETA); ethylenebis-(2-4 hydroxy-phenylglycine) (EHPG); 5-Cl-EHPG; 5Br-EHPG; 5-Me-EHPG; 5t-Bu-EHPG; 5-sec-Bu-EHPG; benzodiethylenetriamine pentaacetic acid (benzo-DTPA); dibenzo-DTPA; phenyl-DTPA, diphenyl-DTPA; benzyl-DTPA; dibenzyl DTPA; bis-2 (hydroxybenzyl)-ethylene-diaminediacetic acid (HBED) and derivatives thereof; Ac-DOTA; benzo-DOTA; dibenzo-DOTA; 1,4,7-triazacyclononane N,N',N''-triacetic acid (NOTA); benzo-NOTA; benzo-TETA, benzo-DOTMA, where DOTMA is 1,4,7,10-tetraazacyclotetradecane-1,4,7,10-tetra(methyl tetraacetic acid), benzo-TETMA, where TETMA is 1,4,8,1 1-tetraazacyclotetradecane-1,4,8,1 1-(methyl tetraacetic acid); derivatives of 1,3-propylenediaminetetraacetic acid (PDTA); triethylenetetraaminehexaacetic acid (TTHA); derivatives of 1,5,10-N,N',N''-tris(2,3-dihydroxybenzoyl)-tricatecholate (LICAM); and 1,3,5-N,N',N''-tris(2,3-dihydroxybenzoyl) aminomethylbenzene (MECAM), and other metal chelators.

In certain embodiments, the nanoprobe comprises cRGDY-PEG-C' dots. In certain embodiments, the nanoprobe comprises cRGDY-PEG-[$^{89}$Zr]C' dots. In certain embodiments, the nanoprobe comprises $NH_2$-cRGDY-PEG-C' dots. In certain embodiments, the nanoprobe comprises DFO-cRGDY-PEG-C' dots. In certain embodiments, the nanoprobe comprises $^{89}$Zr-DFO-cRGDY-PEG-C' dots.

In another aspect, the invention is directed to a method for chelator-free radiolabeling (e.g., $^{89}$Zr labeling) of the nanoprobes created from an aminated nanoparticle, comprising: contacting the nanoparticles with the radiolabel (e.g., $^{89}$Zr-oxalate in HEPES buffer (pH 8) at 75° C.) to produce a first solution; contacting the first solution with a mobile phase solvent (e.g., EDTA, e.g., PBS), thereby producing a chelator-free radiolabeled nanoparticle.

In certain embodiments, free radiolabel forms a complex with the mobile phase solvent.

In certain embodiments, the method comprises aminating the nanoparticle prior to the contacting steps.

In another aspect, the invention is directed to a method for chelator-based radiolabeling (e.g., $^{89}$Zr labeling) of the nanoprobes created from an aminated nanoparticle of any one of claims 1 to 39, the method comprising: contacting the nanoparticles with a chelator (e.g., DFO-NCS) (e.g., at a pH from about 8 to about 9) to produce an intermediate composition (e.g., at a molar ratio of 1 nanoparticles:20 chelators) (e.g., at room temperature, e.g., at a pH from about 8 to about 9); contacting the intermediate composition with a mobile phase solution (e.g., PBS); and contacting the intermediate composition with a radiolabel (e.g., $^{89}$Zr) (e.g., at room temperature, e.g., at about pH 7).

In certain embodiments, the method comprises removing non-specifically bound radiolabel (e.g., $^{89}$Zr). In certain embodiments, the method comprises aminating the nanoparticle prior to the contacting steps.

In another aspect, the invention is directed to a method of treating a disease or condition, the method comprising administering to a subject a composition (e.g., a pharmaceutical composition) comprising: the nanoprobes created from an aminated nanoparticle, wherein the radiolabel is a therapeutic radiolabel conjugated to the nanoparticle (e.g., covalently or non-covalently bonded to the nanoparticle via a linker or covalently or non-covalently bonded directly to the nanoparticle, or associated with the nanoparticle or a composition surrounding the nanoparticle, e.g., via van der Waals forces).

In certain embodiments, the method comprises administering immunotherapy. In certain embodiments, the immunotherapy comprises administering to a subject a pharmaceutical composition comprising the nanoprobes.

In another aspect, the invention is directed to a nanoprobe (e.g., radioconjugate, e.g., nanoconjugate) created from an aminated nanoparticle, the nanoprobe comprising: a nanoparticle (e.g., an ultrasmall nanoparticle, e.g., a silica-based nanoparticle, e.g., a C' dot (e.g., $NH_2$-cRGDY-PEG-C' dot)); a targeting agent (e.g., an antibody fragment, e.g., a targeting peptide (e.g., cRGD or an analog thereof)) conjugated to the nanoparticle (e.g., directly or indirectly); and a radiolabel (e.g., $^{89}$Zr) (e.g., wherein the radiolabel is associated with the nanoparticle (e.g., covalently or non-covalently bonded to the nanoparticle via a linker or covalently or non-covalently bonded directly to the nanoparticle, or associated with the nanoparticle or a composition surrounding the nanoparticle, e.g., via van der Waals forces) (e.g., without a chelator (e.g., wherein the nanoprobe is chelator-free)) (e.g., with a chelator)), wherein the nanoparticle is amine-functionalized prior to conjugation or association with the targeting agent and/or the radiolabel, and wherein the nanoparticle has a diameter (e.g., average diameter) no greater than 20 nanometers (e.g., as measured by dynamic light scattering (DLS) in aqueous solution, e.g., saline solution) (e.g., wherein the average nanoparticle diameter is from 1 to 20 nm, e.g., from 1 to 15 nm, e.g., from 1 to 10 nm, e.g., from 1 to 8 nm, e.g., from 4 to 10 nm, e.g., from 4 to 8 nm) (e.g., wherein the nanoprobe has an average diameter no greater than 50 nm, e.g., no greater than 40 nm, e.g., no greater than 30 nm, e.g., no greater than 20 nm, e.g., no greater than 15 nm, e.g., no greater than 10 nm), for use in a method of treating a disease and/or condition in a subject, wherein the treating comprises delivering the composition to the subject.

In another aspect, the invention is directed to a nanoprobe (e.g., radioconjugate, e.g., nanoconjugate) created from an aminated nanoparticle, the nanoprobe comprising: a nanoparticle (e.g., an ultrasmall nanoparticle, e.g., a silica-based nanoparticle, e.g., a C' dot (e.g., $NH_2$-cRGDY-PEG-C' dot)); a targeting agent (e.g., an antibody fragment, e.g., a targeting peptide (e.g., cRGD or an analog thereof)) conjugated to the nanoparticle (e.g., directly or indirectly); and a radiolabel (e.g., $^{89}$Zr) (e.g., wherein the radiolabel is associated with the nanoparticle (e.g., covalently or non-covalently bonded to the nanoparticle via a linker or covalently or non-covalently bonded directly to the nanoparticle, or associated with the nanoparticle or a composition surrounding the nanoparticle, e.g., via van der Waals forces) (e.g., without a chelator (e.g., wherein the nanoprobe is chelator-free)) (e.g., with a chelator)), wherein the nanoparticle is amine-functionalized prior to conjugation or association with the targeting agent and/or the radiolabel, and wherein the nanoparticle has a diameter (e.g., average diameter) no greater than 20 nanometers (e.g., as measured by dynamic light scattering (DLS)

in aqueous solution, e.g., saline solution) (e.g., wherein the average nanoparticle diameter is from 1 to 20 nm, e.g., from 1 to 15 nm, e.g., from 1 to 10 nm, e.g., from 1 to 8 nm, e.g., from 4 to 10 nm, e.g., from 4 to 8 nm) (e.g., wherein the nanoprobe has an average diameter no greater than 50 nm, e.g., no greater than 40 nm, e.g., no greater than 30 nm, e.g., no greater than 20 nm, e.g., no greater than 15 nm, e.g., no greater than 10 nm), for use in a method of monitoring of a disease and/or condition in a subject, wherein the monitoring comprises delivering the composition to the subject.

In another aspect, the invention is directed to a nanoprobe (e.g., radioconjugate, e.g., nanoconjugate) created from an aminated nanoparticle, the nanoprobe comprising: a nanoparticle (e.g., an ultrasmall nanoparticle, e.g., a silica-based nanoparticle, e.g., a C' dot (e.g., $NH_2$-cRGDY-PEG-C' dot)); a targeting agent (e.g., an antibody fragment, e.g., a targeting peptide (e.g., cRGD or an analog thereof)) conjugated to the nanoparticle (e.g., directly or indirectly); and a radiolabel (e.g., $^{89}Zr$) (e.g., wherein the radiolabel is associated with the nanoparticle (e.g., covalently or non-covalently bonded to the nanoparticle via a linker or covalently or non-covalently bonded directly to the nanoparticle, or associated with the nanoparticle or a composition surrounding the nanoparticle, e.g., via van der Waals forces) (e.g., without a chelator (e.g., wherein the nanoprobe is chelator-free)) (e.g., with a chelator)), wherein the nanoparticle is amine-functionalized prior to conjugation or association with the targeting agent and/or the radiolabel, and wherein the nanoparticle has a diameter (e.g., average diameter) no greater than 20 nanometers (e.g., as measured by dynamic light scattering (DLS) in aqueous solution, e.g., saline solution) (e.g., wherein the average nanoparticle diameter is from 1 to 20 nm, e.g., from 1 to 15 nm, e.g., from 1 to 10 nm, e.g., from 1 to 8 nm, e.g., from 4 to 10 nm, e.g., from 4 to 8 nm) (e.g., wherein the nanoprobe has an average diameter no greater than 50 nm, e.g., no greater than 40 nm, e.g., no greater than 30 nm, e.g., no greater than 20 nm, e.g., no greater than 15 nm, e.g., no greater than 10 nm), for use in (a) a method of treating a disease and/or condition in a subject or (b) in a method of monitoring of a disease and/or condition in a subject, wherein the monitoring comprises delivering the composition to the subject.

In another aspect the invention is directed to a nanoprobe (e.g., radioconjugate, e.g., nanoconjugate) created from an aminated nanoparticle, the nanoprobe comprising: a nanoparticle (e.g., an ultrasmall nanoparticle, e.g., a silica-based nanoparticle, e.g., a C' dot (e.g., $NH_2$-cRGDY-PEG-C' dot)); a targeting agent (e.g., an antibody fragment, e.g., a targeting peptide (e.g., cRGD or an analog thereof)) conjugated to the nanoparticle (e.g., directly or indirectly); and a radiolabel (e.g., $^{89}Zr$) (e.g., wherein the radiolabel is associated with the nanoparticle (e.g., covalently or non-covalently bonded to the nanoparticle via a linker or covalently or non-covalently bonded directly to the nanoparticle, or associated with the nanoparticle or a composition surrounding the nanoparticle, e.g., via van der Waals forces) (e.g., without a chelator (e.g., wherein the nanoprobe is chelator-free)) (e.g., with a chelator)), wherein the nanoparticle is amine-functionalized prior to conjugation or association with the targeting agent and/or the radiolabel, and wherein the nanoparticle has a diameter (e.g., average diameter) no greater than 20 nanometers (e.g., as measured by dynamic light scattering (DLS) in aqueous solution, e.g., saline solution) (e.g., wherein the average nanoparticle diameter is from 1 to 20 nm, e.g., from 1 to 15 nm, e.g., from 1 to 10 nm, e.g., from 1 to 8 nm, e.g., from 4 to 10 nm, e.g., from 4 to 8 nm) (e.g., wherein the nanoprobe has an average diameter no greater than 50 nm, e.g., no greater than 40 nm, e.g., no greater than 30 nm, e.g., no greater than 20 nm, e.g., no greater than 15 nm, e.g., no greater than 10 nm), for use in therapy.

In another aspect, the invention is directed to a nanoprobe (e.g., radioconjugate, e.g., nanoconjugate) created from an aminated nanoparticle, the nanoprobe comprising: a nanoparticle (e.g., an ultrasmall nanoparticle, e.g., a silica-based nanoparticle, e.g., a C' dot (e.g., $NH_2$-cRGDY-PEG-C' dot)); a targeting agent (e.g., an antibody fragment, e.g., a targeting peptide (e.g., cRGD or an analog thereof)) conjugated to the nanoparticle (e.g., directly or indirectly); and a radiolabel (e.g., $^{89}Zr$) (e.g., wherein the radiolabel is associated with the nanoparticle (e.g., covalently or non-covalently bonded to the nanoparticle via a linker or covalently or non-covalently bonded directly to the nanoparticle, or associated with the nanoparticle or a composition surrounding the nanoparticle, e.g., via van der Waals forces) (e.g., without a chelator (e.g., wherein the nanoprobe is chelator-free)) (e.g., with a chelator)), wherein the nanoparticle is amine-functionalized prior to conjugation or association with the targeting agent and/or the radiolabel, and wherein the nanoparticle has a diameter (e.g., average diameter) no greater than 20 nanometers (e.g., as measured by dynamic light scattering (DLS) in aqueous solution, e.g., saline solution) (e.g., wherein the average nanoparticle diameter is from 1 to 20 nm, e.g., from 1 to 15 nm, e.g., from 1 to 10 nm, e.g., from 1 to 8 nm, e.g., from 4 to 10 nm, e.g., from 4 to 8 nm) (e.g., wherein the nanoprobe has an average diameter no greater than 50 nm, e.g., no greater than 40 nm, e.g., no greater than 30 nm, e.g., no greater than 20 nm, e.g., no greater than 15 nm, e.g., no greater than 10 nm), for use in monitoring a disease or condition.

Elements of embodiments involving one aspect of the invention (e.g., methods) can be applied in embodiments involving other aspects of the invention (e.g., systems), and vice versa.

DEFINITIONS

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration": The term "administration" refers to introducing a substance into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In certain embodiments, administration is oral. Additionally or alternatively, in certain embodiments, administration is parenteral. In certain embodiments, administration is intravenous.

"Antibody": As used herein, the term "antibody" refers to a polypeptide that includes canonical immunoglobulin sequence elements sufficient to confer specific binding to a particular target antigen. Intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: $CH_1$, $CH_2$, and the carboxy-terminal $CH_3$ (located at the base of the Y's stem). A short region, known as the "switch", connects the heavy chain variable and constant regions. The "hinge" connects $CH_2$ and $CH_3$ domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the $CH_2$ domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. Affinity and/or other binding attributes of Fc regions for Fc receptors can be modulated through glycosylation or other modification. In certain embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In certain embodiments, an antibody is polyclonal; in certain embodiments, an antibody is monoclonal. In certain embodiments, an antibody has constant region sequences that are characteristic of mouse, rabbit, primate, or human antibodies. In certain embodiments, antibody sequence elements are humanized, primatized, chimeric, etc, as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgG, IgE and IgM, bi- or multi-specific antibodies (e.g., Zybodies®, etc), single chain Fvs, polypeptide-Fc fusions, Fabs, cameloid antibodies, masked antibodies (e.g., Probodies®), Small Modular ImmunoPharmaceuticals ("SMIPs™"), single chain or Tandem diabodies (TandAb®), VHHs, Anticalins®, Nanobodies®, minibodies, BiTE®s, ankyrin repeat proteins or DARPINs®, Avimers®, a DART, a TCR-like antibody, Adnectins®, Affilins®, Trans-bodies®, Affibodies®, a TrimerX®, MicroProteins, Fynomers®, Centyrins®, and a KALBITOR®. In certain embodiments, an antibody may lack a covalent modification (e.g., attachment of a glycan) that it would have if produced naturally. In certain embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.]).

"Antibody fragment": As used herein, an "antibody fragment" includes a portion of an intact antibody, such as, for example, the antigen-binding or variable region of an antibody. Examples of antibody fragments include Fab, Fab', F(ab')2, and Fv fragments; triabodies; tetrabodies; linear antibodies; single-chain antibody molecules; and multi specific antibodies formed from antibody fragments. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. In many embodiments, an antibody fragment contains sufficient sequence of the parent antibody of which it is a fragment that it binds to the same antigen as does the parent antibody; in certain embodiments, a fragment binds to the antigen with a comparable affinity to that of the parent antibody and/or competes with the parent antibody for binding to the antigen. Examples of antigen binding fragments of an antibody include, but are not limited to, Fab fragment, Fab' fragment, F(ab')2 fragment, scFv fragment, Fv fragment, dsFv diabody, dAb fragment, Fd' fragment, Fd fragment, and an isolated complementarity determining region (CDR) region. An antigen binding fragment of an antibody may be produced by any means. For example, an antigen binding fragment of an antibody may be enzymatically or chemically produced by fragmentation of an intact antibody and/or it may be recombinantly produced from a gene encoding the partial antibody sequence. Alternatively or additionally, antigen binding fragment of an antibody may be wholly or partially synthetically produced. An antigen binding fragment of an antibody may optionally comprise a single chain antibody fragment. Alternatively or additionally, an antigen binding fragment of an antibody may comprise multiple chains which are linked together, for example, by disulfide linkages. An antigen binding fragment of an antibody may optionally comprise a multimolecular complex. A functional single domain antibody fragment is in a range from about 5 kDa to about 25 kDa, e.g., from about 10 kDa to about 20 kDa, e.g., about 15 kDa; a functional single-chain fragment is from about 10 kDa to about 50 kDa, e.g., from about 20 kDa to about 45 kDa, e.g., from about 25 kDa to about 30 kDa; and a functional fab fragment is from about 40 kDa to about 80 kDa, e.g., from about 50 kDa to about 70 kDa, e.g., about 60 kDa.

"Associated": As used herein, the term "associated" typically refers to two or more entities in physical proximity with one another, either directly or indirectly (e.g., via one or more additional entities that serve as a linking agent), to form a structure that is sufficiently stable so that the entities remain in physical proximity under relevant conditions, e.g., physiological conditions. In certain embodiments, associated moieties are covalently linked to one another. In certain embodiments, associated entities are non-covalently linked. In certain embodiments, associated entities are linked to one another by specific non-covalent interactions (e.g., by interactions between interacting ligands that discriminate between their interaction partner and other entities present in the context of use, such as, for example streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, electrostatic interactions, hydrogen bonding, affinity, metal coordination, physical adsorption, host-guest interactions, hydrophobic interactions, pi stacking interactions, van der Waals interactions, magnetic interactions, electrostatic interactions, dipole-dipole interactions, etc.

"Biocompatible": The term "biocompatible", as used herein is intended to describe materials that do not elicit a substantial detrimental response in vivo. In certain embodiments, the materials are "biocompatible" if they are not toxic to cells. In certain embodiments, materials are "biocompatible" if their addition to cells in vitro results in less than or equal to 20% cell death, and/or their administration in vivo does not induce inflammation or other such adverse effects. In certain embodiments, materials are biodegradable.

"Biodegradable": As used herein, "biodegradable" materials are those that, when introduced into cells, are broken down by cellular machinery (e.g., enzymatic degradation) or by hydrolysis into components that cells can either reuse or dispose of without significant toxic effects on the cells. In certain embodiments, components generated by breakdown of a biodegradable material do not induce inflammation and/or other adverse effects in vivo. In certain embodiments, biodegradable materials are enzymatically broken down. Alternatively or additionally, in certain embodiments, biodegradable materials are broken down by hydrolysis. In certain embodiments, biodegradable polymeric materials break down into their component polymers. In certain embodiments, breakdown of biodegradable materials (including, for example, biodegradable polymeric materials) includes hydrolysis of ester bonds. In certain embodiments, breakdown of materials (including, for example, biodegradable polymeric materials) includes cleavage of urethane linkages.

"Cancer": As used herein, the term "cancer" refers to a disease, disorder, or condition in which cells exhibit relatively abnormal, uncontrolled, and/or autonomous growth, so that they display an abnormally elevated proliferation rate and/or aberrant growth phenotype characterized by a significant loss of control of cell proliferation. In certain embodiments, a cancer may be characterized by one or more tumors. Those skilled in the art are aware of a variety of types of cancer including, for example, adrenocortical carcinoma, astrocytoma, basal cell carcinoma, carcinoid, cardiac, cholangiocarcinoma, chordoma, chronic myeloproliferative neoplasms, craniopharyngioma, ductal carcinoma in situ, ependymoma, intraocular melanoma, gastrointestinal carcinoid tumor, gastrointestinal stromal tumor (GIST), gestational trophoblastic disease, glioma, histiocytosis, leukemia (e.g., acute lymphoblastic leukemia (ALL), acute myeloid leukemia (AML), chronic lymphocytic leukemia (CLL), chronic myelogenous leukemia (CML), hairy cell leukemia, myelogenous leukemia, myeloid leukemia), lymphoma (e.g., Burkitt lymphoma [non-Hodgkin lymphoma], cutaneous T-cell lymphoma, Hodgkin lymphoma, mycosis fungoides, Sezary syndrome, AIDS-related lymphoma, follicular lymphoma, diffuse large B-cell lymphoma), melanoma, merkel cell carcinoma, mesothelioma, myeloma (e.g., multiple myeloma), myelodysplastic syndrome, papillomatosis, paraganglioma, pheochromacytoma, pleuropulmonary blastoma, retinoblastoma, sarcoma (e.g., Ewing sarcoma, Kaposi sarcoma, osteosarcoma, rhabdomyosarcoma, uterine sarcoma, vascular sarcoma), Wilms' tumor, and/or cancer of the adrenal cortex, anus, appendix, bile duct, bladder, bone, brain, breast, bronchus, central nervous system, cervix, colon, endometrium, esophagus, eye, fallopian tube, gall bladder, gastrointestinal tract, germ cell, head and neck, heart, intestine, kidney (e.g., Wilms' tumor), larynx, liver, lung (e.g., non-small cell lung cancer, small cell lung cancer), mouth, nasal cavity, oral cavity, ovary, pancreas, rectum, skin, stomach, testes, throat, thyroid, penis, pharynx, peritoneum, pituitary, prostate, rectum, salivary gland, ureter, urethra, uterus, vagina, or vulva.

"Carrier": As used herein, "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

"Imaging agent": As used herein, "imaging agent" refers to any element, molecule, functional group, compound, fragments thereof or moiety that facilitates detection of an agent (e.g., a polysaccharide nanoparticle) to which it is joined. Examples of imaging agents include, but are not limited to: various ligands, radionuclides (e.g., $^3$H, $^{14}$C, $^{18}$F, $^{19}$F, $^{32}$P, $^{35}$S, $^{135}$I, $^{125}$I, $^{123}$I, $^{131}$I, $^{64}$CU, $^{67}$Ga, $^{68}$Ga, $^{187}$Re, $^{111}$In, $^{90}$Y, $^{99m}$Tc, $^{177}$Lu, $^{89}$Zr etc.), fluorescent dyes (for specific exemplary fluorescent dyes, see below), chemiluminescent agents (such as, for example, acridinum esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold, and the like), biotin, dioxigenin, haptens, and proteins for which antisera or monoclonal antibodies are available. The radionuclides may be attached via click chemistry, for example. In certain embodiments, the antibody fragment is modified to include an azide. In certain embodiments, the surface of the polymer-coated nanoparticle is modified to include Dibenzocyclooctyne (DBCO). In certain embodiments, a DBCO-functionalized nanoparticle is pre-synthesized by reacting an aminated nanoparticle with a DBCO-NHS ester, followed by conjugation to the click-chemistry functionalized (e.g., azide-functionalized) antibody fragment.

"Protein": As used herein, the term "protein" refers to a polypeptide (i.e., a string of at least 3-5 amino acids linked to one another by peptide bonds). Proteins may include moieties other than amino acids (e.g., may be glycoproteins, proteoglycans, etc.) and/or may be otherwise processed or modified. In certain embodiments "protein" can be a complete polypeptide as produced by and/or active in a cell (with or without a signal sequence); in certain embodiments, a "protein" is or comprises a characteristic portion such as a polypeptide as produced by and/or active in a cell. In certain embodiments, a protein includes more than one polypeptide chain. For example, polypeptide chains may be linked by one or more disulfide bonds or associated by other means. In certain embodiments, proteins or polypeptides as described herein may contain L-amino acids, D-amino acids, or both, and/or may contain any of a variety of amino acid modifications or analogs known in the art. Useful modifications include, e.g., terminal acetylation, amidation, methylation, etc. In certain embodiments, proteins or polypeptides may comprise natural amino acids, non-natural amino acids, synthetic amino acids, and/or combinations thereof. In certain embodiments, proteins are or comprise antibodies, antibody polypeptides, antibody fragments, biologically active portions thereof, and/or characteristic portions thereof. In certain embodiments, the protein is a small protein (e.g., wherein the small protein is less than 20 kDa, e.g., wherein the small protein is preferably less than 15 kDa, e.g., wherein the small protein is preferably 12 kDa or less).

"Pharmaceutical composition": As used herein, the term "pharmaceutical composition" refers to an active agent, formulated together with one or more pharmaceutically acceptable carriers. In certain embodiments, active agent is present in unit dose amount appropriate for administration in a therapeutic regimen that shows a statistically significant probability of achieving a predetermined therapeutic effect when administered to a relevant population. In certain embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

"Substantially": As used herein, the term "substantially", and grammatic equivalents, refer to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

"Subject": As used herein, the term "subject" includes humans and mammals (e.g., mice, rats, pigs, cats, dogs, and horses). In many embodiments, subjects are mammals, particularly primates, especially humans. In certain embodiments, subjects are livestock such as cattle, sheep, goats, cows, swine, and the like; poultry such as chickens, ducks, geese, turkeys, and the like; and domesticated animals particularly pets such as dogs and cats. In certain embodiments (e.g., particularly in research contexts) subject are, for example, rodents (e.g., mice, rats, hamsters), rabbits, primates, or swine such as inbred pigs and the like.

"Therapeutic agent": As used herein, the phrase "therapeutic agent" refers to any agent that has a therapeutic effect and/or elicits a desired biological and/or pharmacological effect, when administered to a subject.

"Therapeutically effective amount": as used herein, is meant an amount that produces the desired effect for which it is administered. In certain embodiments, the term refers to an amount that is sufficient, when administered to a population suffering from or susceptible to a disease, disorder, and/or condition in accordance with a therapeutic dosing regimen, to treat the disease, disorder, and/or condition. In certain embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In certain embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in certain embodiments, a therapeutically effective amount of a particular agent or therapy may be formulated and/or administered in a single dose. In certain embodiments, a therapeutically effective agent may be formulated and/or administered in a plurality of doses, for example, as part of a dosing regimen.

"Treatment": As used herein, the term "treatment" (also "treat" or "treating") refers to any administration of a substance that partially or completely alleviates, ameliorates, relives, inhibits, delays onset of, reduces severity of, and/or reduces incidence of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In certain embodiments, treatment may be of a subject who has been diagnosed as suffering from the relevant disease, disorder, and/or condition. In certain embodiments, treatment may be of a subject known to have one or more susceptibility factors that are statistically correlated with increased risk of development of the relevant disease, disorder, and/or condition.

Drawings are presented herein for illustration purposes, not for limitation.

BRIEF DESCRIPTION OF DRAWINGS

The foregoing and other objects, aspects, features, and advantages of the present disclosure will become more apparent and better understood by referring to the following description taken in conduction with the accompanying drawings, in which:

FIGS. 1A-1F show plots depicting characterization of cRGDY-PEG-C' dots and NH$_2$-cRGDY-PEG-C' dots. GPC elugram (FIG. 1A), FCS correlation curve with fit (FIG. 1B), and UV-vis absorbance spectra (FIG. 1C) of cRGDY-PEG-C' dots as compared to PEG-C' dots. GPC elugram (FIG. 1D), FCS correlation curve with fit (FIG. 1E), and UV-vis absorbance spectra (FIG. 1F) of amine-functionalized NH$_2$-cRGDY-PEG-C' dots as compared to PEG-C' dots.

FIG. 2A is a graph showing concentration-dependent chelator-free $^{89}$Zr labeling of cRGDY-PEG-C' dots. Labeling temperature was set to 75° C.; Labeling pH was set to 8; C' dots (nmol) to $^{89}$Zr (mCi) ratio was in the range of zero to 7.5 nmol/mCi.

FIG. 2B is a graph showing pH-dependent chelator-free $^{89}$Zr labeling. Labeling temperature: 75° C.; C' dots to $^{89}$Zr ratio: 7.5 nmol/mCi; Labeling pH range: 2-9.

FIG. 2C is a graph showing temperature-dependent chelator-free $^{89}$Zr labeling. Labeling pH: 8; C' dot to $^{89}$Zr ratio: 7.5 nmol/mCi; Labeling temperature range: 25° C. to 75° C.

FIG. 2D is a graph showing chelator-free $^{89}$Zr labeling comparison between C' dots with regular PEGylation procedures and particles modified with additional small silane molecules (e.g., diethoxy dimethyl silane). Labeling temperature: 75° C.; Labeling pH: 8; C' dots to $^{89}$Zr ratio: 7.5 nmol/mCi.

FIG. 2E is a graph showing concentration-dependent chelator-based $^{89}$Zr labeling of DFO-cRGDY-PEG-C' dots. Labeling temperature: 37° C.; Labeling pH: 7.5; C' dots to $^{89}$Zr ratio range: zero to 0.75 nmol/mCi.

FIG. 2F is a graph showing Microwave Plasma-Atomic Emission Spectrometer (MP-AES) testing of the number of $^{nat}$Zr per DFO-cRGDY-PEG-C' dots particles synthesized with varied particle to DFO-NCS ratios.

(FIG. 3A) In vitro and (FIG. 3B) in vivo radiostability, as well as (FIG. 3C) blood circulation half-times for chelator-free $^{89}$Zr-labeled cRGDY-PEG-C' dots and (FIG. 3D) chelator-based $^{89}$Zr-labeled cRGDY-PEG-C' dots. (**p<0.005).

(FIG. 4A) Chelator-free $^{89}$Zr-labeled cRGDY-PEG-C' dots and (FIG. 4B) chelator-based $^{89}$Zr-labeled cRGDY-PEG-C' dots. The first 60 min time-activity curves for major organs (i.e., heart, bladder, liver, muscle, and kidney) in mice i.v.-injected with (FIG. 4C) chelator-free $^{89}$Zr-labeled cRGDY-PEG-[$^{89}$Zr]C' dots and (FIG. 4D) chelator-based $^{89}$Zr-labeled $^{89}$Zr-DFO-cRGDY-PEG-C' dots. All images in (FIG. 4A) and (FIG. 4B) are coronal Maximum Intensity Projection (MIP) Positron Emission Tomography (PET) images.

(FIG. 5A) Chelator-free $^{89}$Zr-labeled cRGDY-PEG-[$^{89}$Zr]C' dots and (FIG. 5B) chelator-based $^{89}$Zr-labeled $^{89}$Zr-DFO-cRGDY-PEG-C' dots in healthy mice (n=3). (FIG. 5C) Comparison of time-dependent bone uptake in mice injected with the $^{89}$Zr-labeled cRGDY-PEG-C' dots. (**p<0.005)

FIGS. 6A-6J are images and graphs depicting in vivo tumor-targeted coronal PET images of mice and their analysis. Mice injected with (FIG. 6A) cRGDY-PEG-[$^{89}$Zr]C' dots, chelator-free labeling, in M21 tumor-bearing mice (n=3), (FIG. 6B)$^{89}$Zr-DFO-cRGDY-PEG-C' dots, chelator-based labeling, in M21 tumor-bearing mice (n=3), and (FIG. 6C) 89Zr-DFO-cRGDY-PEG-C' dots, chelator-based labeling, in M21 L tumor-bearing mice (n=3). MIP images at 2 h and 72 h are presented to reveal the extended blood half-time of the particles, renal clearance of particles into the bladder at 2 h post-injection, as well as the bone and joint uptake at 72 h post-injection. Time activity curves showing (FIG. 6D) chelator-free $^{89}$Zr-labeled cRGDY-PEG-[$^{89}$Zr]C' dots in M21 xenografts, (FIG. 6E) chelator-based 89Zr-labeled $^{89}$Zr-DFO-cRGDY-PEG-C' dots in M21 xenografts, and (FIG. 6F) chelator-based $^{89}$Zr-labeled $^{89}$Zr-DFO-cRGDY-PEG-C' dots in M21-L xenografts. Comparisons of (FIG. 6G) tumor uptake, (FIG. 6H) tumor-to-blood ratios, (FIG. 6I) tumor-to-liver ratios, and (FIG. 6J) tumor-to-muscle ratios among three groups. N=3 for each group.

FIGS. 9A and 9B are plots depicting representative PD-10 elution profiles of (FIG. 9A) chelator-free $^{89}$Zr-labeled cRGDY-PEG-C' dots, (FIG. 9B) chelator-based $^{89}$Zr-labeled cRGDY-PEG-C' dots.

FIGS. 12A-12B are images depicting a PET screening study showing differences in bone uptake in mice injected with cRGDY-PEG-[$^{89}$Zr]C' dots (FIG. 12A) without EDTA challenge and (FIG. 12B) with overnight EDTA challenge.

FIGS. 16A and 16B are schematics that show $^{89}$Zr-radiolabeling strategies of cRGDY-PEG-C' dots, according to an illustrative embodiments of the invention.

FIG. 16A is a schematic that shows a chelator-free strategy, according to an illustrative embodiment of the invention: the surface and/or internal deprotonated silanol groups (—Si—O—) from the (1) cRGDY-PEG-C' dots are functioning as the inherent oxygen donors (or hard Lewis bases)

for the successful labeling of $^{89}$Zr (a hard Lewis acid) at 75° C., pH 8, forming (2) cRGDY-PEG-[$^{89}$Zr]C' dots.

FIG. 16B is a schematic that shows a chelator-based strategy, according to an illustrative embodiment of the invention: DFO chelators are conjugated to the surface of amine-functionalized NH$_2$-cRGDY-PEG-C' dots by reacting DFO-NCS with the amine groups on the silica surface of the C' dots; as synthesized (4) DFO-cRGDY-PEG-C' dots are then labeled with 89Zr at 37° C., pH 7, forming (5)$^{89}$Zr-DFO-cRGDY-PEG-C' dots. The molecular structures of the chelated radiometal for both strategies are rendered in 3D and 2D on the right. The atoms of silicon, oxygen, carbon, nitrogen, sulfur, hydrogen and zirconium in the 3D renderings are colored in purple, red, gray, blue, yellow, white and light green, respectively.

Figure 17:
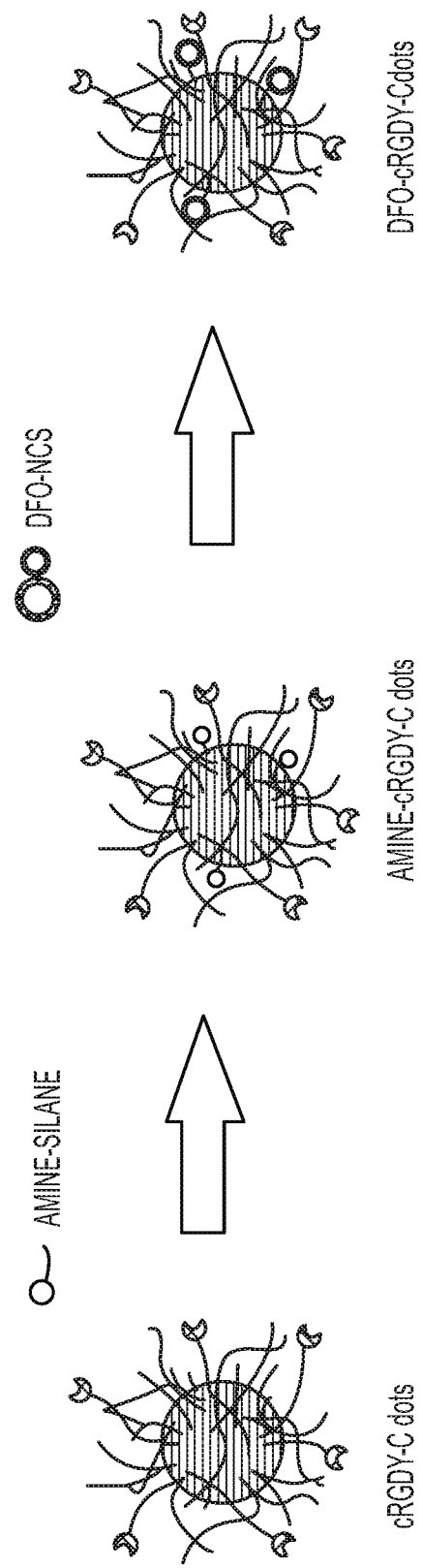

FIG. 17 is a schematic showing synthesis of cRGDY-PEG-C' dots and/or NH$_2$-cRGDY-PEG-C' dots that are made using a one-pot synthesis technique, according to an illustrative embodiment of the invention. cRGDY-C' dots are contacted with amine-silane to create amine-cRDGY-C' dots. amine-cRDGY-C' dots are then contacted, in the same "pot" with DFO-NCS to generate DFO-cRDGY-C' dots.

DETAILED DESCRIPTION

Throughout the description, where compositions are described as having, including, or comprising specific components, or where methods are described as having, including, or comprising specific steps, it is contemplated that, additionally, there are compositions of the present invention that consist essentially of, or consist of, the recited components, and that there are methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Described herein are a variety of surface radiolabeling strategies of radio-nanoprobes for (i) favorable pre-clinical and clinical pharmacokinetic profiles derived after fine-tuning surface chemical properties. The present disclosure describes how the biological properties of these nanoprobes (e.g., radioconjugates) are influenced by the conjugation of radiometals, such as zirconium-89 ($^{89}$Zr, $t_{1/2}$=78.4 h), using different radiolabeling strategies. The attachment of $^{89}$Zr to surface-aminated, integrin-targeting ultrasmall nanoparticles (e.g., C' dots) via various radiolabelling strategies led to favorable PK and clearance profiles. Moreover, the radiolabeling strategies led to significant improvements in targeted tumor uptake and target-to-background ratios in melanoma models relative to biological controls while maintaining particle sizes below the effective renal glomerular filtration size cutoff of less than 10 nm. Nanoprobes were also characterized in terms their radiostability and plasma residence half-times. The described $^{89}$Zr-labeled ultrasmall hybrid organic-inorganic particle tracers offer radiobiological properties suitable for enhanced molecularly-targeted cancer imaging in humans.

In certain embodiments, the nanoprobes are described by Bradbury et al., "NANOPARTICLE IMMUNOCONJUGATES," International Patent Application No. PCT/US16/26434, the contents of which is hereby incorporated by reference in its entirety. In certain embodiments, the nanoprobes are described by Bradbury et al., "NANOPARTICLE DRUG CONJUGATES" in U.S. Publication No. US 2015/0343091A1, the contents of which are hereby incorporated by reference in its entirety. In certain embodiments, the nanoprobes and radiolabeling methods are described by Chen, F. et al. "Target-or-Clear Zirconium-89 Labeled Silica Nanoparticles for Enhanced Cancer-Directed Uptake in Melanoma: A Comparison of Radiolabeling Strategies." Chem Mater 29, 8269-8281 (2017), Ma, K. et al. "Control of Ultrasmall Sub-10 nm Ligand-Functionalized Fluorescent Core-Shell Silica Nanoparticle Growth in Water." Chem Mater 27, 4119-4133 (2015), and Ma, K. & Wiesner, U. "Modular and Orthogonal Post-PEGylation Surface Modifications by Insertion Enabling Penta-Functional Ultrasmall Organic-Silica Hybrid Nanoparticles." Chem Mater 29, 6840-6855 (2017), the contents of which are hereby incorporated by reference in their entireties.

Fast renal clearance, relatively short blood circulation half-times (ranging from several minutes to several hours) and low RES uptake (on the order of 5% ID/g or less) represent defining biological features for ultrasmall (sub-10 nm) renally clearable nanoparticles (Table 1). Table 1 shows a summary of in vivo tumor (active/passive) targeting of sub-10 nm renally excreted nanoparticles. For example, Iodine-124 ($^{124}$I, $t_{1/2}$=100.2 h) labeled cRGDY-C dot-PEG PET/optical dual-modality probes are currently in Phase 2A clinical trial studies (NCT01266096, NCT02106598).

TABLE 1

| Ultrasmall nanoparticles | HD size | Blood circulaiton half-time ($t_{1/2}$) | Liver uptake (% ID/g) | Kidney Uptake (% ID/g) | Tumor uptake (% ID/g) | Active or passive targetin | Tumor-to-liver ratio | Clinical trials |
|---|---|---|---|---|---|---|---|---|
| $^{99m}$Tc-QDs-GPI [a] | 4-5 | 126 min | 6-7 | ~30 | — | Active | — | — |
| $^{99m}$Tc-QDs-cRGD [b] | 4-5 | 113 min | 6-7 | ~40 | — | Active | — | — |
| [$^{198}$Au]Au-GSH [c] | 2-3 | 12.7 h | ~5 | ~10 | — | — | — | — |
| Au-PEG$_{1k}$ [d] | 5-6 | 9.2 ± 3.9 h | ~5 | ~10 | 4-8 (MCF-7) | Passive | ~1 | — |
| $^{124}$I-cRGDY-PEG-C dot [e] | 6-7 | 5.6 ± 0.2 h | 4-5 | 2-4 | 1-2 (M21) | Active | <1 | Phase 2A |
| [$^{64}$Cu]CuS-PVP [f] | 5.6 | 11.7 ± 3.5 h | ~5 | 2.5 | 0.2-3.6 (4T1) | Passive | <1 | — |
| $^{64}$Cu-NOTA-Au [g] | 2-3 | <10 min | <0.5 | <2 | — | — | — | — |
| cRGDY-PEG-[$^{89}$Zr]C' dots | 6-7 | 13.7 h | ~5 | 2-4 | 8-10 (M21) | Active | ~2 | — |

TABLE 1-continued

| Ultrasmall nanoparticles | HD size | Blood circulaiton half-time ($t_{1/2}$) | Liver uptake (% ID/g) | Kidney Uptake (% ID/g) | Tumor uptake (% ID/g) | Active or passive targetin | Tumor-to-liver ratio | Clinical trials |
|---|---|---|---|---|---|---|---|---|
| $^{89}$Zr-DFO-cRGDY-PEG-C' dots | 6-7 | 15.3 h | ~5 | 2-4 | 10-12 (M21) | Active | >2 | — |

[a] Core-shell type QDs or CdSe/ZnS-Cys-based nanoparticles were conjugated with GPI, a small molecular ligand that targets prostate-specific membrane antigen-positive prostate cancer cells. Nanoparticles were radiolabeled with $^{99m}$Tc for ex vivo biodistribution studies. Uptake in liver and kidney are presented as % ID/g. For 6-8 week old nude mice having a body weight of ~25 g, the weights of livers and kidneys are on the order of 1.5 and 0.17 g, respectively. No PEGylation was utilized for surface protection. Liver and kidney uptake was measured at 4 h post-injection; tumor uptake data was not available.
[b] QDs are core-shell structured CdSe/ZnS-Cys nanoparticles that are conjugated with cRGD peptides and radiolabeled with $^{99m}$Tc. Liver and kidney uptake are presented as % ID/g. For 6-8 week old nude mice having a body weight of ~25 g, the weights of livers and kidneys are on the order of 1.5 and 0.17 g, respectively. No PEGylation was utilized for surface protection. Liver and kidney uptake was measured at 4 h post-injection; tumor uptake data was not available.
[c] [$^{198}$Au]Au-GSH ($^{198}$Au: $T_{1/2}$ ~2.7 d) is an intrinsically radiolabeled nanoparticle used for SPECT-CT imaging, and which emits near-infrared light (~800 nm). In vivo tumor targeting data is not shown.
[d] Au-PEG$_{1k}$ is synthesized by thermally reducing HAuCl$_4$ in the presence of thiolated polyethylene glycol (PEG) with a molecular weight of 1 kDa. Maximal tumor uptake was estimated on the basis of inductively coupled plasma mass spectrometry to be about 8% ID/g at 12 h post-injection, which decreased by 50% 48 h post-injection.
[e] $^{124}$I-cRGDY-PEG-C dot is radiolabeled and conjugated with targeting ligands (cRGDY) for in vivo dual-modality tumor-targeted imaging.$^8$ It is also a first-of-its-kind inorganic particle receiving FDA Investigational New Drug (IND) approval for first-in-human clinical trials.
[f] [$^{64}$Cu]CuS-PVP is an intrinsically $^{64}$Cu-labeled and polyvinylpyrrolidone (PVP)-capped CuS nanoparticle. The nanoparticle can be used for PET imaging and photothermal therapy. Tumor uptake peaked at 3.6% ID/g 2 h post-injection in 4T1 tumor-bearing mice. However, ~95% of the tumor accumulation was eliminated by 24 h post-injection, resulting in ~0.2% ID/g tumor uptake.
[g] $^{64}$Cu-NOTA-Au is synthesized by conjugating NOTA chelator to Au-GSH nanoparticles, followed by labeling with $^{64}$Cu for dynamic PET imaging. Surprisingly, blood circulation half-time was estimated to be less than 10 min, significantly shorter than Au-GSH nanoparticles (>10 h).

Having a physical half-life comparable to that of $^{124}$I, zirconium-89 ($^{89}$Zr, $t_{1/2}$=78.4 h) is now a widely used positron emitting radioisotope (Table 2) in pre-clinical and clinical trials. Table 2 shows a summary of decay properties of the commonly used PET isotopes.

TABLE 2

| Radioisotope | Decay half-life (h) | Mean $\beta^+$ energy (keV) | Branching ratio |
|---|---|---|---|
| Gallium-68 ($^{68}$Ga) | 1.1 | 829.5 | 88.9% |
| Fluorine-18 ($^{18}$F) | 1.8 | 249.8 | 96.7% |
| Copper-64 ($^{64}$Cu) | 12.7 | 278 | 17.6% |
| Zirconium-89 ($^{89}$Zr) | 78.4 | 396 | 22.7% |
| Iodine-124 ($^{124}$I) | 100.2 | 820 | 22.7% |

Moreover, $^{89}$Zr has a much lower mean f energy (396 keV vs 820 keV) which may improve PET spatial resolution. In contrast to $^{124}$I, which is known to typically undergo dehalogenation after uptake into cells, $^{89}$Zr has been reported to residualize stably within cells after internalization, underscoring its potential to enhance targeted particle accumulations and target-to-background ratios, in addition to more accurate estimation of actual nanoprobe uptake in the tumor.

As described herein, expanding the radionuclide from $^{124}$I to $^{89}$Zr required investigation and comparisons of chelator-based and chelator-free radiolabeling strategies for attaching surface radiometals (e.g., $^{89}$Zr) to ultrasmall nanoparticles (C' dots) via radiolabeling strategies described herein. It was determined whether (1) chelator-free radiolabeling procedures, previously applied to larger size (porous and non-porous) silica particles, could be successfully extended to particle sizes below 10 nm and (2) resulting $^{89}$Zr-labeled peptide- and PEG-functionalized C' dots (or cRGDY-PEG-C' dots) yielded high targeted uptake and target-to-background ratios in well-established integrin-expressing melanoma models while maintaining sub-10 nm sizes facilitating renal excretion.

For example, to date, silica-based $^{89}$Zr chelator-free radiolabeling has focused exclusively on nanoparticles with a diameter larger than 100 nm to provide sufficient silanol group density (>105/particle). It is described herein that, for a significantly reduced surface and internal silanol group density, $^{89}$Zr chelator-free labeling of ultrasmall (6-7 nm) PEGylated silica nanoparticles is able to be utilized.

Without wishing to be bound to any theory, results of these findings can inform development of a targeted radiotherapeutic platform by substitution of the diagnostic for a therapeutic radiolabel, such as lutetium-177. For example, as described herein, by taking advantage of surface functionalization strategies adapted to a small particle size (markedly reduced radius of curvature) while maintaining particle size to preserve clearance properties of the as-developed C' dot platform, substitution of a diagnostic isotope for a therapeutic one, such as Lu-177 or Y-90, is possible. The provided aminated C' dot platform also facilitates conjugation of other suitable chelators (e.g., NOTA, DOTA, DTPA) beyond DFO for radio-labeling.

The chelator-free strategy was achieved by $^{89}$Zr labeling of the intrinsic deprotonated silanol groups (e.g., —Si—O$^-$) on the surface and within each particle at elevated temperature (75° C., pH 8, FIG. 16A). A chelator-based $^{89}$Zr labeling technique (37° C., pH 7.5) was also developed by carefully controlling the surface density of the selected chelator (e.g., DFO-NCS) to maximize specific activity and radiochemical yields while maintaining the renal clearance property (FIG. 16B). Nanoprobes were extensively characterized in term of their radiostability, pharmacokinetics, radiation dosimetry properties, active tumor targeting and target-to-background ratios by PET imaging. To the best of knowledge of the inventors, this is the first-of-its-kind $^{89}$Zr-labeled and renally clearable targeted organic-inorganic hybrid particle for dual-modality imaging. On the basis of its favorable biological properties, including extended blood circulation half-times (~15 h), high tumor targeting uptake (>10% ID/g), renal clearance (>60% ID within 1-2 days), low liver accumulation (~5% ID/g), and high tumor-to-background ratios (tumor:muscle >9; tumor:liver >2), this platform serves as a diagnostic imaging tool for cancer-specific detection and localization in patients with cancer (e.g., melanoma) and a targeted radiotherapeutic probe for treating disease.

In certain embodiments, the nanoparticle comprises silica, polymer (e.g., poly(lactic-co-glycolic acid) (PLGA)), biologics (e.g., protein carriers), and/or metal (e.g., gold, iron). In certain embodiments, the nanoparticle is a "C dot" as described in U.S. Publication No. 2013/0039848 A1 by Bradbury et al., which is hereby incorporated by reference.

In certain embodiments, the nanoparticle is spherical. In certain embodiments, the nanoparticle is non-spherical. In certain embodiments, the nanoparticle is or comprises a material selected from the group consisting of metal/semi-metal/non-metals, metal/semi-metal/non-metal-oxides,-sulfides,-carbides, -nitrides, liposomes, semiconductors, and/or combinations thereof. In certain embodiments, the metal is selected from the group consisting of gold, silver, copper, and/or combinations thereof.

The nanoparticle may comprise metal/semi-metal/non-metal oxides including silica ($SiO_2$), titania ($TiO_2$), alumina ($Al_2O_3$), zirconia ($Z_rO_2$), germania ($GeO_2$), tantalum pentoxide ($Ta_2O_5$), $NbO_2$, etc., and/or non-oxides including metal/semi-metal/non-metal borides, carbides, sulfide and nitrides, such as titanium and its combinations (Ti, $TiB_2$, TiC, TiN, etc.).

The nanoparticle may comprise one or more polymers, e.g., one or more polymers that have been approved for use in humans by the U.S. Food and Drug Administration (FDA) under 21 C.F.R. § 177.2600, including, but not limited to, polyesters (e.g., polylactic acid, poly(lactic-co-glycolic acid), polycaprolactone, polyvalerolactone, poly(1,3-dioxan-2-one)); polyanhydrides (e.g., poly(sebacic anhydride)); polyethers (e.g., polyethylene glycol); polyurethanes; polymethacrylates; polyacrylates; polycyanoacrylates; copolymers of PEG and poly(ethylene oxide) (PEO).

The nanoparticle may comprise one or more degradable polymers, for example, certain polyesters, polyanhydrides, polyorthoesters, polyphosphazenes, polyphosphoesters, certain polyhydroxyacids, polypropylfumerates, polycaprolactones, polyamides, poly(amino acids), polyacetals, polyethers, biodegradable polycyanoacrylates, biodegradable polyurethanes and polysaccharides. For example, specific biodegradable polymers that may be used include but are not limited to polylysine, poly(lactic acid) (PLA), poly (glycolic acid) (PGA), poly(caprolactone) (PCL), poly(lactide-co-glycolide) (PLG), poly(lactide-co-caprolactone) (PLC), and poly(glycolide-co-caprolactone) (PGC). Another exemplary degradable polymer is poly(beta-amino esters), which may be suitable for use in accordance with the present application.

In certain embodiments, a nanoparticle can have or be modified to have one or more functional groups. Such functional groups (within or on the surface of a nanoparticle) can be used for association with any agents (e.g., detectable entities, targeting entities, therapeutic entities, or PEG). In addition to changing the surface charge by introducing or modifying surface functionality, the introduction of different functional groups allows the conjugation of linkers (e.g., (cleavable or (bio-)degradable) polymers such as, but not limited to, polyethylene glycol, polypropylene glycol, PLGA, etc.), targeting/homing agents, and/or combinations thereof.

In certain embodiments, the nanoparticle comprises one or more targeting ligands (e.g., attached thereto), such as, but not limited to, small molecules (e.g., folates, dyes, etc.), aptamers (e.g., A10, AS1411), polysaccharides, small biomolecules (e.g., folic acid, galactose, bisphosphonate, biotin), oligonucleotides, and/or proteins (e.g., (poly)peptides (e.g., αMSH, RGD, octreotide, AP peptide, epidermal growth factor, chlorotoxin, transferrin, etc.), antibodies, antibody fragments, proteins, etc.). In certain embodiments, the nanoparticle comprises one or more contrast/imaging agents (e.g., fluorescent dyes, (chelated) radioisotopes (SPECT, PET), MR-active agents, CT-agents), and/or therapeutic agents (e.g., small molecule drugs (e.g., checkpoint inhibitors), therapeutic (poly)peptides, therapeutic antibodies, (chelated) radioisotopes, etc.).

In certain embodiments, selection of class and/or species of checkpoint inhibitors for attachment to the nanoparticle depends on a selection of an initial therapeutic administered to a subject e.g., as in combination therapy, where a first drug and/or a first therapy (e.g., radiation) is administered prior to administration of the nanoprobe comprising the nanoparticle and attached checkpoint inhibitor. The selection of class and/or species of checkpoint inhibitor may also or alternatively be selected based on how that the initial therapeutic alters the tissue microenvironment. Changes in the microenvironment can be determined, for example, by mapping immune cell profiles. Moreover, a categorical approach can be used to group inhibitors based on observed changes in the microenvironment observed for a particular therapeutic.

In certain embodiments, PET (Positron Emission Tomography) tracers are used as imaging agents. In certain embodiments, PET tracers comprise $^{89}Zr$, $^{64}Cu$, $[^{18}F]$fluorodeoxyglucose. In certain embodiments, the nanoparticle includes these and/or other radiolabels.

In certain embodiments, the nanoparticle comprises one or more fluorophores. Fluorophores comprise fluorochromes, fluorochrome quencher molecules, any organic or inorganic dyes, metal chelates, or any fluorescent enzyme substrates, including protease activatable enzyme substrates. In certain embodiments, fluorophores comprise long chain carbophilic cyanines. In other embodiments, fluorophores comprise DiI, DiR, DiD, and the like. Fluorochromes comprise far red, and near infrared fluorochromes (NIRF). Fluorochromes include but are not limited to a carbocyanine and indocyanine fluorochromes. In certain embodiments, imaging agents comprise commercially available fluorochromes including, but not limited to Cy5.5, Cy5 and Cy7 (GE Healthcare); AlexaFlour660, AlexaFlour680, AlexaFluor750, and AlexaFluor790 (Invitrogen); VivoTag680, VivoTag-S680, and VivoTag-S750 (VisEn Medical); Dy677, Dy682, Dy752 and Dy780 (Dyomics); DyLight547, DyLight647 (Pierce); HiLyte Fluor 647, HiLyte Fluor 680, and HiLyte Fluor 750 (AnaSpec); IRDye 800CW, IRDye 800RS, and IRDye 700DX (Li-Cor); and ADS780WS, ADS830WS, and ADS832WS (American Dye Source) and Kodak X-SIGHT 650, Kodak X-SIGHT 691, Kodak X-SIGHT 751 (Carestream Health).

In certain embodiments, the nanoparticle comprises (e.g., has attached) one or more targeting ligands, e.g., for targeting cancer tissue/cells of interest.

In certain embodiments, the nanoparticles comprise from 1 to 20 discrete targeting moieties (e.g., of the same type or different types), wherein the targeting moieties bind to receptors on tumor cells (e.g., wherein the nanoparticles have an average diameter no greater than 15 nm, e.g., no greater than 10 nm, e.g., from about 5 nm to about 7 nm, e.g., about 6 nm). In certain embodiments, the 1 to 20 targeting moieties comprises alpha-melanocyte-stimulating hormone (αMSH). In certain embodiments, the nanoparticles comprise a targeting moiety (e.g., αMSH). In certain embodiments, diagnostic nanoparticles are optimized in terms of their physical and/or chemical properties (e.g., surface chemistry, surface charge, diameter, shape, number of ligands) so that they are able to be renally cleared. In certain embodiments, theranostic nanoparticles are optimized in terms of their physical and/or chemical properties (e.g., surface chemistry, surface charge, diameter, shape, number of ligands) so that they are able to be renally cleared (e.g., for imaging or other diagnostic applications) or so that they are not renally cleared (e.g., for therapeutic and/or theranostic applications).

Cancers that may be treated include, for example, prostate cancer, breast cancer, testicular cancer, cervical cancer, lung cancer, colon cancer, bone cancer, glioma, glioblastoma, multiple myeloma, sarcoma, small cell carcinoma, melanoma, renal cancer, liver cancer, head and neck cancer, esophageal cancer, thyroid cancer, lymphoma, pancreatic (e.g., BxPC3), lung (e.g., H1650), and/or leukemia. Moreover, the described compositions can be used to treat pathological angiogenesis, including tumor neovascularization. Growth of human tumors and development of metastases depend on the de novo formation of blood vessels. The formation of new blood vessels is tightly regulated by VEGF and VEGF-R, for example.

In certain embodiments, the nanoparticle comprises a therapeutic agent, e.g., a drug moiety (e.g., a chemotherapy drug) and/or a therapeutic radioisotope. As used herein, "therapeutic agent" refers to any agent that has a therapeutic effect and/or elicits a desired biological and/or pharmacological effect, when administered to a subject.

The surface chemistry, uniformity of coating (where there is a coating), surface charge, composition, concentration, frequency of administration, shape, and/or size of the nanoparticle can be adjusted to produce a desired therapeutic effect.

In certain embodiments, the nanoprobes comprises a chelator, for example, 1,4,8,11-tetraazabicyclo[6.6.2]hexadecane-4,11-diyl)diacetic acid (CB-TE2A); desferoxamine (DFO); diethylenetriaminepentaacetic acid (DTPA); 1,4,7,10-tetraazacyclotetradecane-1,4,7,10-tetraacetic acid (DOTA); thylenediaminetetraacetic acid (EDTA); ethylene glycolbis(2-aminoethyl)-N,N,N',N'-tetraacetic acid (EGTA); 1,4,8,11-tetraazacyclotetradecane-1, 4,8,11-tetraacetic acid (TETA); ethylenebis-(2-4 hydroxy-phenylglycine) (EHPG); 5-Cl-EHPG; 5Br-EHPG; 5-Me-EHPG; 5t-Bu-EHPG; 5-sec-Bu-EHPG; benzodiethylenetriamine pentaacetic acid (benzo-DTPA); dibenzo-DTPA; phenyl-DTPA, diphenyl-DTPA; benzyl-DTPA; dibenzyl DTPA; bis-2 (hydroxybenzyl)-ethylene-diaminediacetic acid (HBED) and derivatives thereof; Ac-DOTA; benzo-DOTA; dibenzo-DOTA; 1,4,7-triazacyclononane N,N',N''-triacetic acid (NOTA); benzo-NOTA; benzo-TETA, benzo-DOTMA, where DOTMA is 1,4,7,10-tetraazacyclotetradecane-1,4,7,10-tetra(methyl tetraacetic acid), benzo-TETMA, where TETMA is 1,4,8,11 1-tetraazacyclotetradecane-1,4,8,11 1-(methyl tetraacetic acid); derivatives of 1,3-propylenediaminetetraacetic acid (PDTA); triethylenetetraaminehexaacetic acid (TTHA); derivatives of 1,5,10-N,N',N''-tris (2,3-dihydroxybenzoyl)-tricatecholate (LICAM); and 1,3,5-N,N',N''-tris(2,3-dihydroxybenzoyl)aminomethylbenzene (MECAM), or other metal chelators.

In certain embodiments, the nanoconjugate comprises more than one chelator.

In certain embodiments the radioisotope-chelator pair is $^{89}$Zr-DFO. In certain embodiments the radioisotope-chelator pair is $^{177}$Lu-DOTA. In certain embodiments, the radioisotope-chelator pair is $^{225}$Ac-DOTA.

EXPERIMENTAL EXAMPLES

Chelator-Free Zirconium-89 Radiolabeling of cRGDY-PEG-C' Dots.

Nanoparticle-based chelator-free radiolabeling has emerged as an intrinsic radiolabeling technique in the last several years, especially for radioisotopes (e.g., arsenic-72 [$^{72}$As, $t_{1/2}$=26 h], germanium-69 [$^{69}$Ge, $t_{1/2}$=39.1 h]) and titanium-45 [$^{45}$Ti, $t_{1/2}$=3.8 h]$^{36}$) for which suitable chelators are not currently available.

Developing a chelator-free radiolabeling technique for ultrasmall renal clearable nanoparticles is of particular interest since the introduction of additional surface modification steps may increase the particle's hydrodynamic radius and, in turn, reduce or eliminate renal clearance while promoting high liver uptake. Due to the presence of the intrinsic silanol groups (—Si—OH) on the surface (or inside) of each nanoparticle, silica is known to be one of the most versatile nanoplatforms for successful chelator-free labeling using a variety of radiometals, including $^{89}$Zr.

Without wishing to be bound to any theory, the mechanism of labeling is thought to be due to strong interactions between a hard Lewis acid (i.e., radiometal of $^{89}$Zr$^{4+}$) and a hard Lewis base (e.g., deprotonated silanol groups, —Si—O$^-$, from the silica surface). Although a large part of the surface silanol groups have been quenched after the surface PEGylation step using silane-PEG, it was hypothesized that internal silanol groups from each microporous C' dots are still accessible for the chelator-free $^{89}$Zr labeling.

Figure 1E:
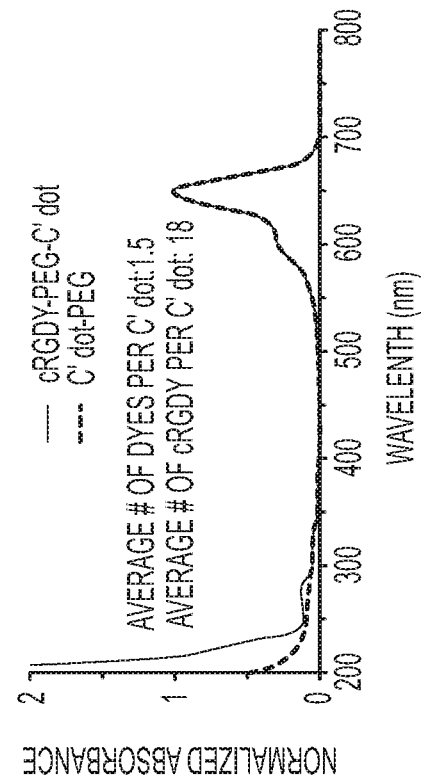
Figure 1F:
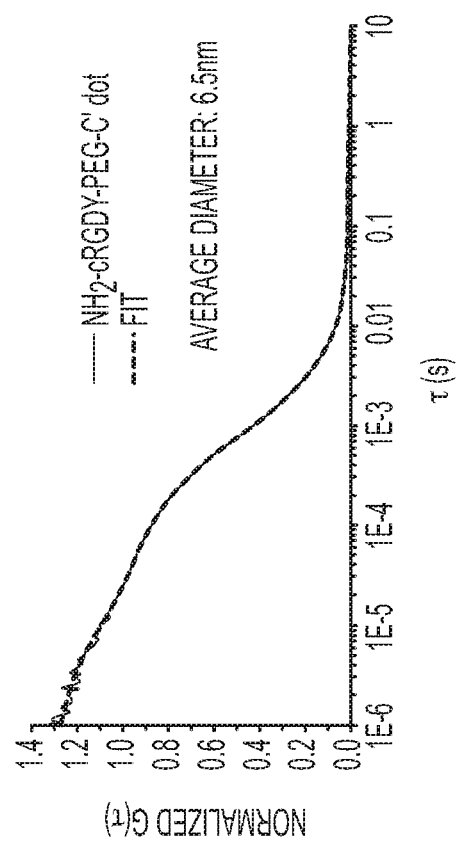

To that end, cRGDY-PEG-C' dots were radiolabeled using $^{89}$Zr$^{4+}$ via a chelator-free strategy. C' dots were synthesized. Near-infrared fluorescent Cy5 dyes were covalently encapsulated into the silica matrix of C' dots, endowing C' dots with fluorescent properties; cancer targeting cRGDY peptides were then covalently attached to the outer surface of the C' dots during PEGylation, allowing for active tumor targeting. The resulting cRGDY-PEG-C' dots were purified and subjected to quality analysis (FIGS. 1A-1F). The GPC elugram of the purified cRGDY-PEG-C' dots showed a single peak at around 9 min, corresponding to C' dots nanoparticles (FIG. 1A). The peak was well fit by a single Gaussian distribution, suggesting 100% purity and narrow particle size distribution (FIG. 1A). The average hydrodynamic diameter of the purified cRGDY-PEG-C' dots was around 6.4 nm (FIG. 1B) as measured by FCS, consistent with TEM observations (FIG. 1A). In addition to particle size, FCS also provides the particle concentration, which was used to estimate the number of functional groups per particle including dyes, targeting peptides and $^{89}$Zr radioisotopes. The UV-vis spectra of the purified cRGDY-PEG-C' dots exhibited strong absorption at wavelength around 650 nm, corresponding to the absorption maximum of Cy5 fluorescent dye (FIG. 1C). As compared to C' dots without cRGDY surface modification (PEG-C' dots) an additional absorption peak was identified at a wavelength around 275 nm attributed to the tyrosine residues on the cRGDY peptides (FIG. 1C). By dividing the concentrations of Cy5 and cRGDY calculated from the UV-vis spectra by the concentration of C' dots measured by FCS, the numbers of Cy5 and cRGDY per C' dots were estimated to be around 1.6 and 20, respectively.

Figure 2C:
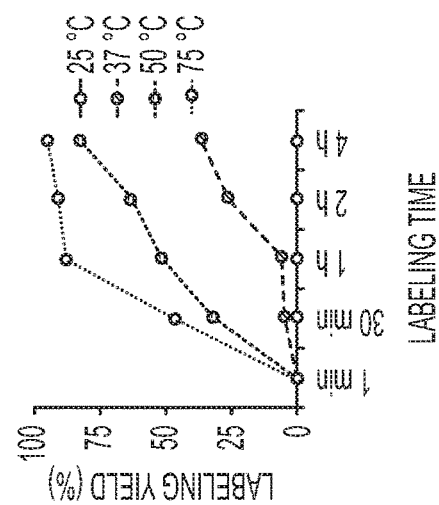
FIGS. 2A-2F are graphs depicting chelator-free and chelator-based $^{89}$Zr radiolabeling studies.
Figure 2B:
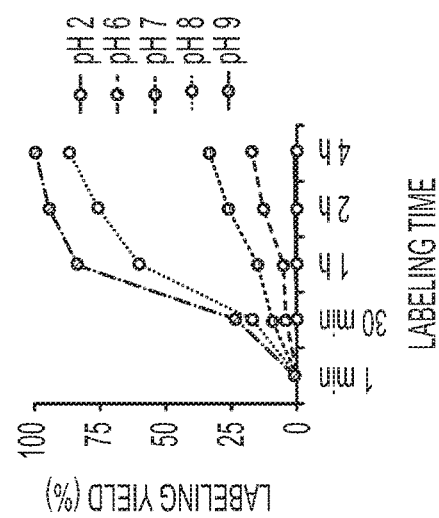
Figure 2A:
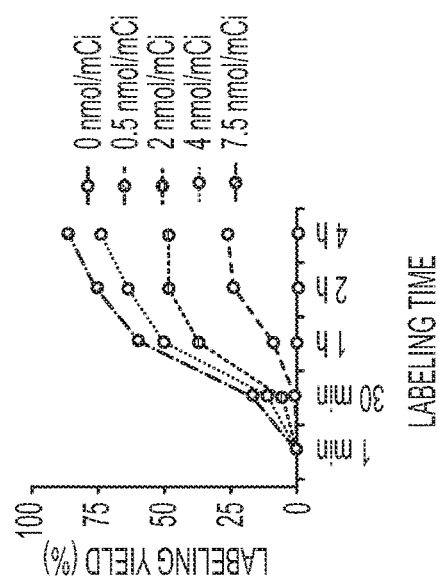

For radiolabeling procedures, 4 nmols of purified cRGDY-PEG-C' dots were mixed with 1 mCi of $^{89}$Zr-oxalate in HEPES buffer (pH 8) at 75° C. Radiochemical yields were monitored by radio-TLC. Results showed that, within the first 1 hour, over 50% $^{89}$Zr labeling yield was achieved. A total of ~75% $^{89}$Zr was successfully attached to the particle over a 4 hour radiolabeling period (FIG. 2A). The labeling process was dependent on the particle concentration: the higher the particle-to-$^{89}$Zr (nmol-to-mCi) ratio, the higher the $^{89}$Zr labeling yield (FIG. 2A). The specific activity of chelator-free $^{89}$Zr-labeled cRGDY-PEG-C' dots (denoted as cRGDY-PEG-[89Zr]C' dots) was found to be in the range of 100-500 Ci/mmol.

Deprotonated silanol groups play a vital role in the chelator-free $^{89}$Zr labeling of silica nanoparticles. When the pH is below the isoelectric point of silica (pH-2-3), the surface silanol groups of C' dots will become protonated, making them unsuitable for chelating with positively charged $^{89}$Zr. This was evidenced by the fact that less than 1% labeling yield was observed at pH 2 and 75° C. (FIG. 2B). Chelator-free $^{89}$Zr labeling was also demonstrated to be temperature-dependent, with higher labeling temperatures leading to faster $^{89}$Zr labeling (FIG. 2C). Labeling pH and temperature ranges were recommended to be pH 8-9 and 50-75° C., respectively.

Figure 2F:
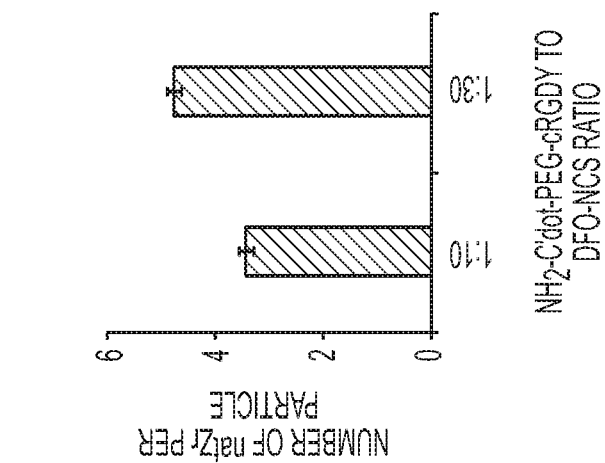
Figure 2E:
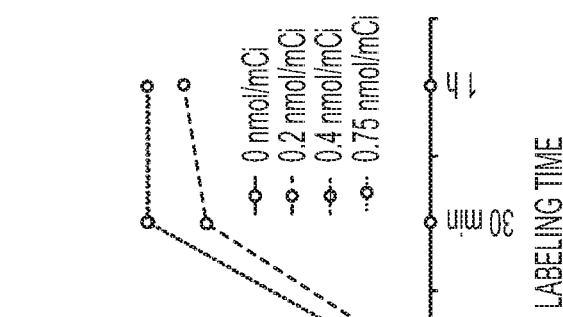
Figure 2D:
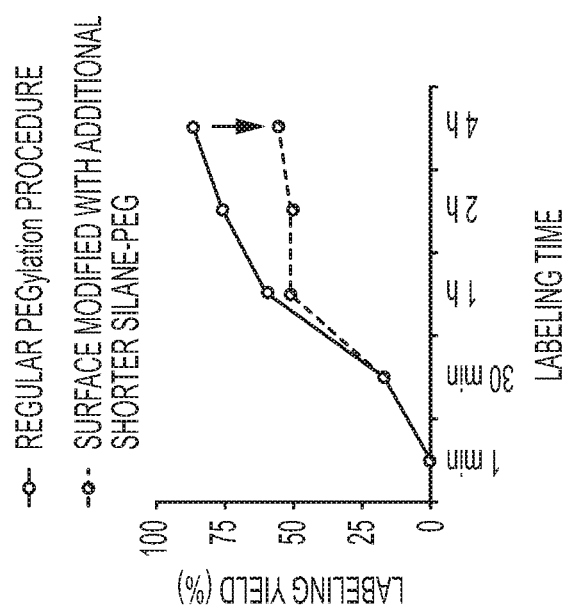
Figure 8A:
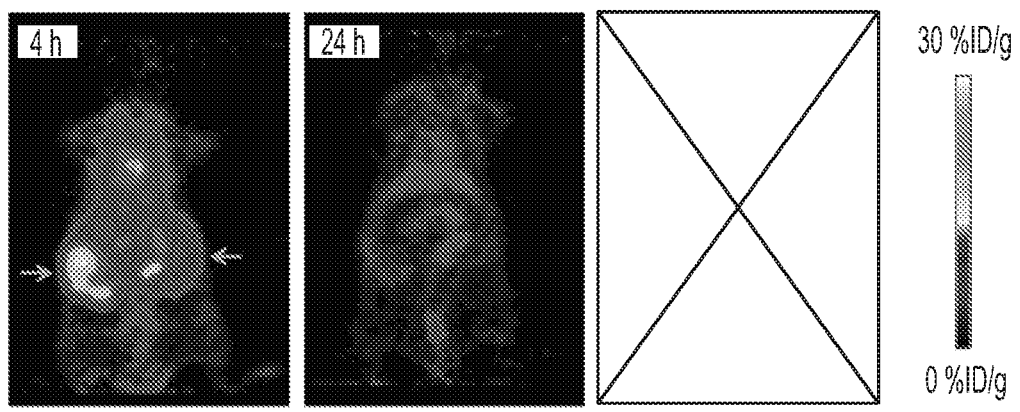
FIG. 8A are images depicting PET imaging of $^{89}$Zr-DFO-cRGDY-PEG-C' dots (using a GSH linker) at 4 and 24 h post-injection time points. Intestinal uptake is marked by red arrows. GSH:glutathione.
Figure 8B:
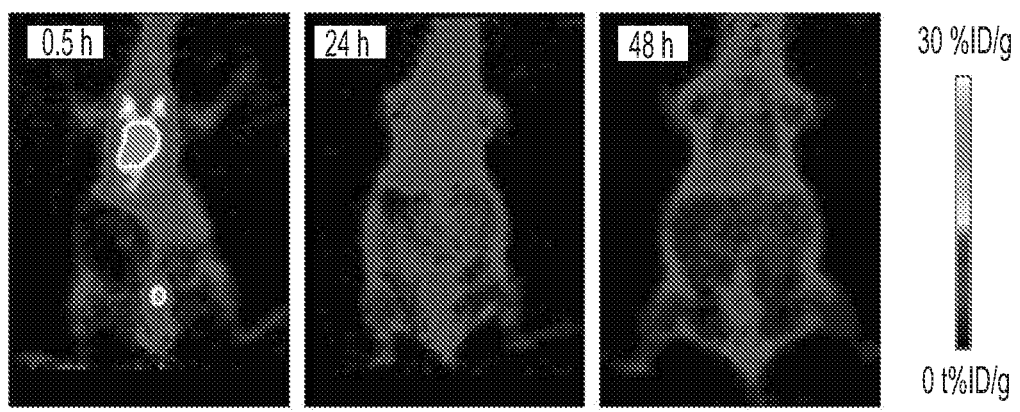
FIG. 8B are images depicting PET imaging of $^{89}$Zr-DFO-cRGDY-PEG-C' dots (using APTES as the linker) at 0.5, 24 and 48 h post-injection time points. APTES: (3-Aminopropyl)triethoxysilane.

To further demonstrate the specific $^{89}$Zr labeling of deprotonated silanol groups, remaining silanol groups on the C' dots surface after PEGylation were quenched via the addition of diethoxy dimethyl silane. The resulting modified cRGDY-PEG-C' dots exhibited a lower surface density of reactive silanol groups, thereby reducing the efficiency of chelator-free radiolabeling. Indeed, an approximate 25% reduction of $^{89}$Zr labeling yield was observed in this case (FIG. 2D). Considering that the average specific activity of $^{89}$Zr-oxalate is about 833 Ci/mmol of zirconium with a greater than 99.9% radiochemical purity, about 0.14-0.63 $^{89}$Zr per cRGDY-PEG-C' dots were estimated for cRGDY-PEG-[$^{89}$Zr]C' dots (Table 3). The number of Zr atoms per particle can be further increased by labeling with cold Zr (or $^{nat}$Zr) at varied ratios. As shown in FIGS. 8A and 8B, the $^{nat}$Zr density of 2.27±0.08 could be achieved by labeling cRGDY-PEG-C' dots with $^{nat}$Zr at a molar ratio of 1 to 10. To date, silica-based $^{89}$Zr chelator-free radiolabeling has been focused exclusively on nanoparticles with a diameter larger than 100 nm to provide sufficient silanol group density (greater than $10^5$/particle). This data shows the first example of successful $^{89}$Zr chelator-free labeling of ultrasmall (e.g., 6-7 nm) PEGylated silica nanoparticles with a significantly reduced surface and internal silanol group density.

Table 3 shows estimation of number of $^{89}$Zr per C' dots for the chelator-free radiolabeling method.

TABLE 3

Chelator-free method

| | C' dots to $^{89}$Zr ratio (nmol/mCi) | | | |
|---|---|---|---|---|
| | 0.5 | 2 | 4 | 7.5 |
| Specific activity of cRGDY-PEG-[$^{89}$Zr]C' dot- (Ci/mmol) | 524 | 244 | 183.8 | 114.9 |
| Average specific activity of $^{89}$Zr-osalate (Ci/mmol) | | 832.5 | | |
| Number of $^{89}$Zr per C' dot | 0.63 | 0.29 | 0.22 | 0.14 |

Chelator-Based Zirconium-89 Radiolabeling of cRGDY-PEG-C' Dots

To achieve chelator-based $^{89}$Zr labeling, p-SCN-Bn-Deferoxamine (DFO-NCS, providing six oxygen donors) was used. In initial attempts, DFO chelator was attached to maleimide functionalized C' dots (mal-cRGDY-PEG-C' dots) by introducing glutathione (GSH) as a linker, converting the maleimide groups on C' dots surface to primary amine groups for DFO-NCS conjugation. The resulting GSH-modified dots were first purified using a PD-10 column, and then conjugated with DFO-NCS chelator via the GHS amine groups, resulting in DFO-cRGDY C' dots for $^{89}$Zr labeling. Although a high labeling yield (greater than 80%) was achieved, every high intestinal uptake of $^{89}$Zr-DFO-cRGDY-PEG-C' dots was observed in a screening PET study (FIG. 8A). Without wishing to be bound to any theory, this uptake can be due to the detachment of $^{89}$Zr-DFO-GSH from the particles. No visible bone uptake was observed at 24 h post-injection, indicating no detachment of free $^{89}$Zr from the radio-conjugates (FIG. 8A).

To solve this problem, primary amine groups were attached directly to the C' dots surface using a recently developed post-PEGylation surface modification by insertion (PPSMI) method. To that end, after C' dots PEGylation, additional amino-silane molecules were added to the reaction and inserted into the PEG layer attaching to the silica surface underneath. The resulting NH$_2$-cRGDY-PEG-C' dots contained reactive amine groups on the silica surface under the PEG layer, allowing for further conjugation with e.g., NCS functionalized DFO chelators. After purification, the NH$_2$-cRGDY-PEG-C' dots exhibited good product quality, similar to cRGDY-PEG-C' dots without amine functionalization (FIGS. 1D-1E). The average diameter of the purified NH$_2$-cRGDY-PEG-C' dots was around 6.5 nm. The number of Cy5 and cRGDY peptides per C' dots were estimated to be around 1.5 and 18, respectively (FIGS. 1D-1E). The purified NH$_2$-cRGDY-PEG-C' dots were then conjugated with DFO-NCS using a reaction molar ratio of 1:20 between the particle and DFO-NCS, followed by purification using a PD-10 column to remove unreacted DFO-NCS. Labeling of $^{89}$Zr-oxalate to the resulting DFO-cRGDY-PEG-C' dots were performed at 37° C. for 60 min. A nearly 100% labeling yield was achieved by using a particle-to-$^{89}$Zr ratio of 0.4 nmol/1mCi (FIG. 2E). The specific activity was estimated to be in the range of 1300-4300 Ci/mmol, significantly higher than that of the sample synthesized by using a chelator-free method. About 1.59-5.14 $^{89}$Zr per C' dots were estimated in the final $^{89}$Zr-DFO-cRGDY-PEG-C' dots product (Table 4). To estimate the number of the accessible DFO per particle, synthesized DFO-cRGDY-PEG-C' dots were first labeled with $^{nat}$Zr and then subjected to $^{nat}$Zr amount quantification by using Microwave Plasma-Atomic Emission Spectroscopy (MP-AES). Results revealed an average of 3.42±0.13 $^{nat}$Zr per C' dots for DFO-cRGDY-PEG-C' dots particle synthesized with a particle to DFO ratio of 1:10 ratio, and 4.76±0.13 for 1:30 ratio (FIG. 2F). Without wishing to be bound to any theory, since excess $^{nat}$Zr was used during the labeling and unreacted $^{nat}$Zr was removed by chelating with EDTA, the number of $^{nat}$Zr per C' dots (about 3-5) should equal to the number of accessible DFO per DFO-cRGDY-PEG-C' dots. A sub-sequent pilot PET imaging study showed a significantly reduced intestinal uptake by using as-developed $^{89}$Zr-DFO-cRGDY-PEG-C' dots (FIG. 8B).

Table 4 shows Estimation of number of $^{89}$Zr per C' dots for the chelator-based radiolabeling method.

TABLE 4

Chelator-based method

| | C' dots to $^{89}$Zr ratio (nmol/mCi) | | |
|---|---|---|---|
| | 0.2 | 0.4 | 07.75 |
| Specific activity of cRGDY-PEG-[$^{89}$Zr]C' dot- (Ci/mmol) | 4280 | 2483 | 1321 |
| Average specific activity of $^{89}$Zr-osalate (Ci/mmol) | | 832.5 | |
| Number of $^{89}$Zr per C' dot | 5.14 | 2.98 | 1.59 |

Radiostability and Blood Circulation Half-Times of $^{89}$Zr-Labeled cRGDY-PEG-C' Dots Next, in vitro stability, in vivo radio-stability, and blood circulation half-life of the two $^{89}$Zr-labeled cRGDY-PEG-C' dots were investigated. Developing radiolabeled nanoparticles with high radio-stability is vital since PET only detects the radioisotopes but not the nanoparticles. Both $^{89}$Zr-labeled cRGDY-PEG-C' dots were synthesized and purified using PD-10 columns. FIGS. 9A and 9B show the representative elution profiles of both $^{89}$Zr-labeled cRGDY-PEG-C' dots in PD-10 columns. The fraction from 2.5 mL to 4.0 mL was collected for the subsequent studies.

Figure 3B:
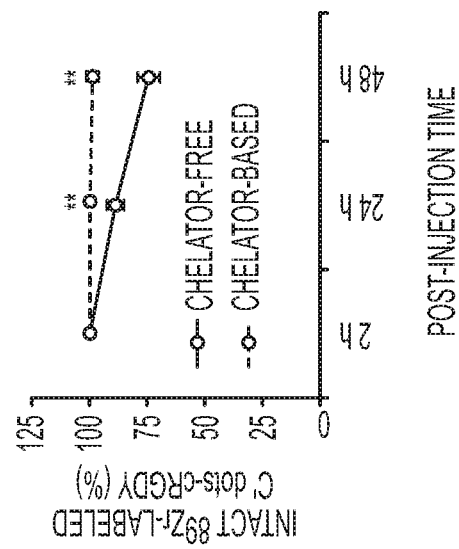
FIGS. 3A-3D are graphs depicting a comparison of chelator-free and chelator-based $^{89}$Zr-labeled C' dots properties.
Figure 3D:
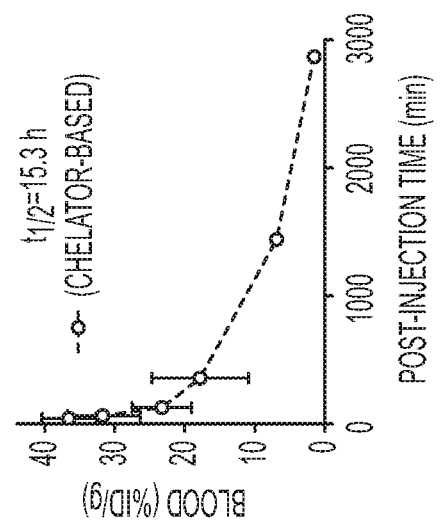
Figure 3A:
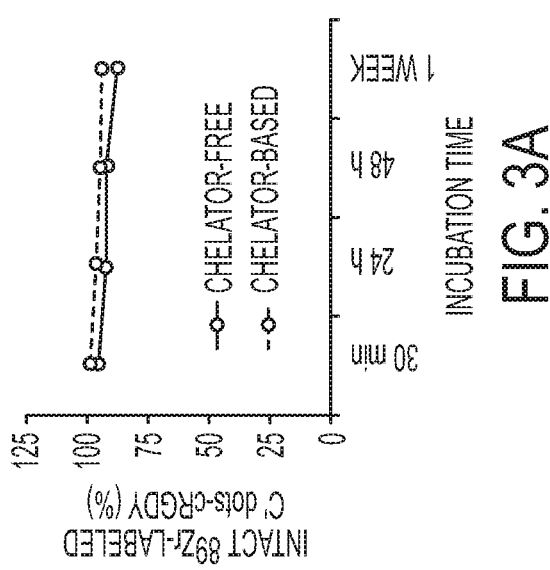

Results showed a comparable stability of both $^{89}$Zr-labeled cRGDY-PEG-C' dots in phosphate-buffered saline (PBS) at room temperature over one week. $^{89}$Zr-DFO-cRGDY-PEG-C' dots showed a slightly better stability with over 95% purity even after one week, while the purity was less than 90% for cRGDY-PEG-[$^{89}$Zr]C' dots (FIG. 3A). A significant difference in radiostability was observed in vivo after measuring the percentage of intact $^{89}$Zr-labeled cRGDY-PEG-C' dots in mouse plasma. As shown in FIG. 3B, and on the basis of radio-TLC, greater than 98% of intact $^{89}$Zr-DFO-cRGDY-PEG-C' dots were estimated at 48 h post-injection in mouse plasma, while it was less than 75% for mice injected with cRGDY-PEG-[$^{89}$Zr]C' dots, indicating the detachment of free $^{89}$Zr during the circulating of cRGDY-PEG-[$^{89}$Zr]C' dots in vivo. More discussions about the differences in the in vivo biodistribution and bone uptake are presented in the following sections.

Figure 3C:
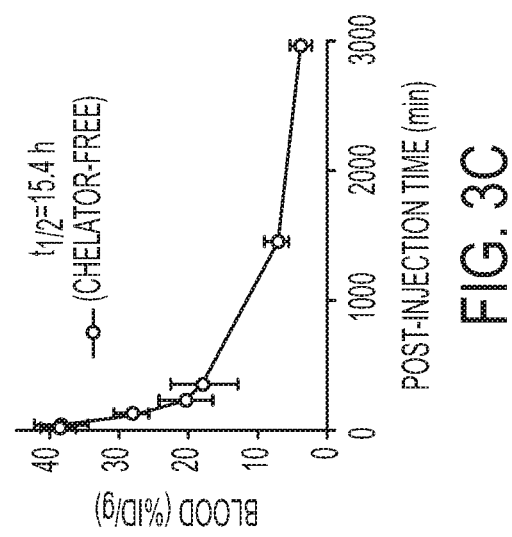

To evaluate the blood circulation half-time, blood from mice intravenously (i.v.) injected with $^{89}$Zr-labeled cRGDY-PEG-C' dots were sampled at various post-injection time points, and assayed by gamma counting (n=3). Blood uptake values were converted to a percentage of the injected dose per gram (% ID/g), and fit with a two-compartment model. As shown in FIGS. 3C and 3D, results suggested a fairly equivalent in vivo blood circulation half-time of about 15 h, greater than those previously published for earlier generation radioiodinated particles (Table 1).

Dynamic PET imaging using 89Zr-labeled cRGDY-PEG-C' dots

Figure 4A:
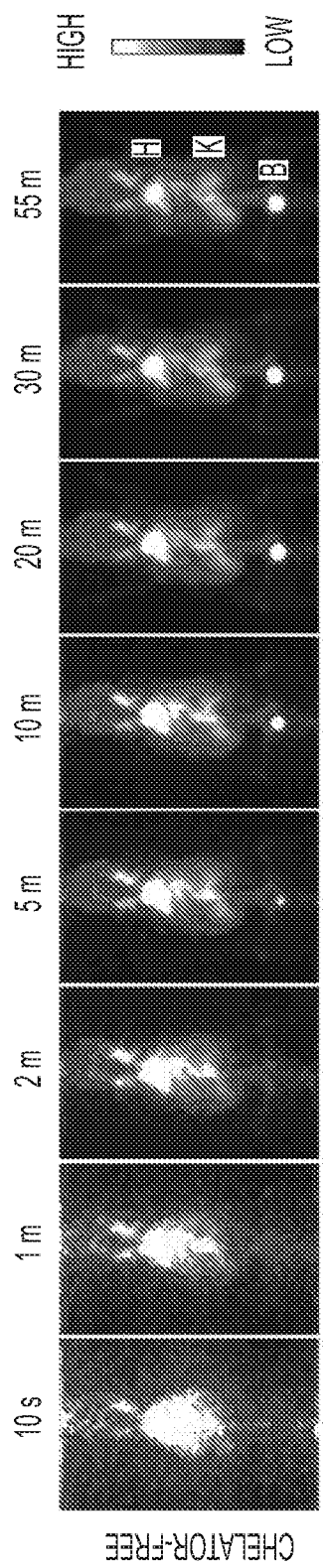
FIGS. 4A-4D show images and graphs depicting a comparison of dynamic PET imaging results in mice for chelator-free and chelator-based $^{89}$Zr-labeled C' dots.
Figure 4B:
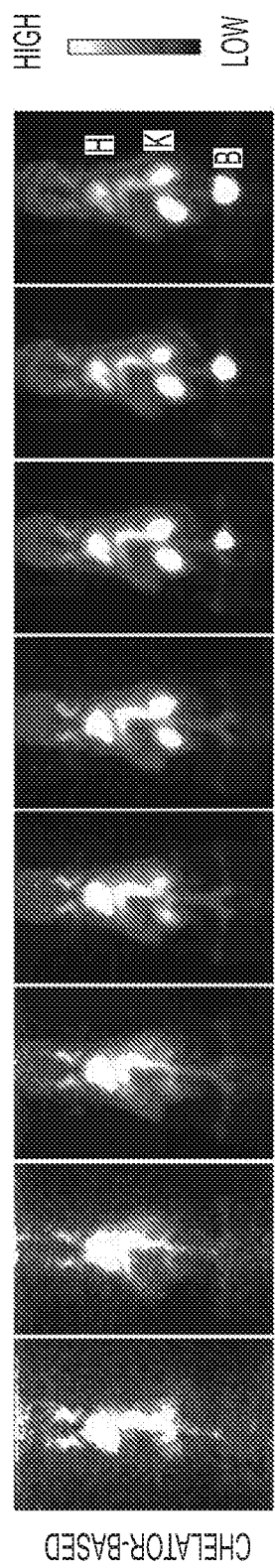
Figure 4C:
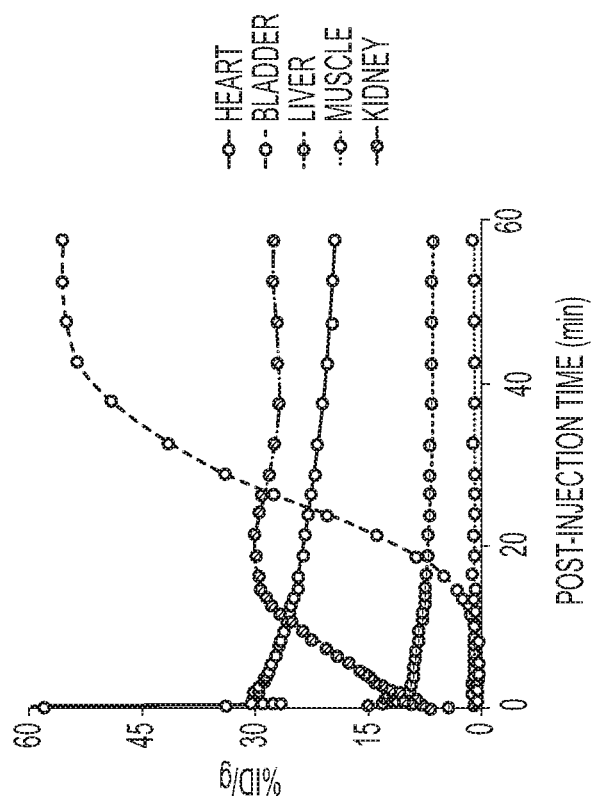
Figure 4D:
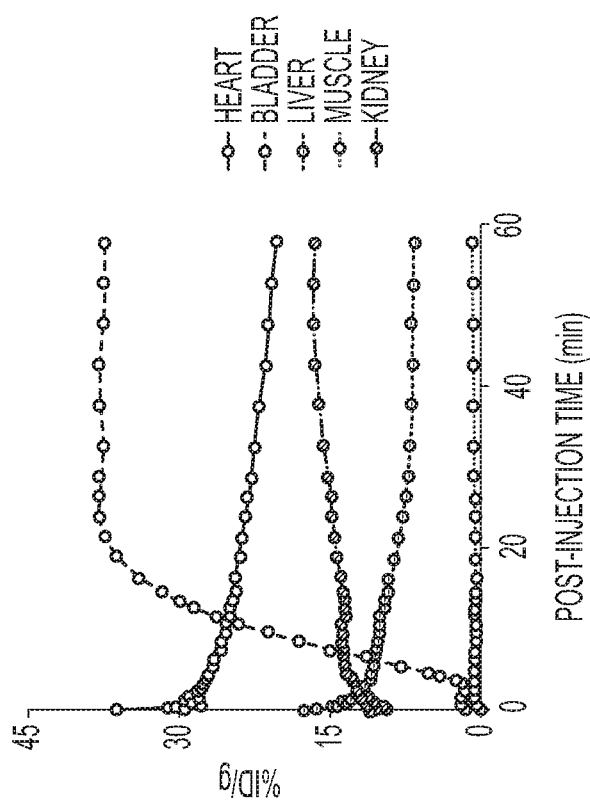

PET is a suitable molecular imaging modality for non-invasively and quantitatively tracking the pharmacokinetics (PK) of various types of radiolabeled probes in vivo with high sensitively. Limited by the tissue penetration depth, it is well-known that optical imaging is generally not suitable for in vivo whole body screening, and quantification of particle distributions within tissues. To track the distribution and fast renal clearance of systemically injected C' dots, particularly in the early post-injection time period, a 60 min-dynamic PET imaging study was performed in representative mice, each animal injected with one of the two of $^{89}$Zr-labeled cRGDY-PEG-C' dots probes. As shown in FIGS. 4A and 4B, maximum intensity projection (MIP) images show marked activity of $^{89}$Zr-labeled cRGDY-PEG-C' dots in the mouse heart immediately after i.v. injection. Gradually reduced heart activity was observed in both cases, with overall activity concentration estimated to be 20.5% ID/g at 60 min post-injection for mice injected with cRGDY-PEG-[$^{89}$Zr]C' dots (FIG. 4C), and 19.3% ID/g for mice injected with $^{89}$Zr-DFO-cRGDY-PEG-C' dots (FIG. 4D). A similar trend was observed for hepatic uptake with 60-min post-injection uptake values of both probes estimated to be ~6.5% ID/g. Significant kidney and bladder uptake was observed as early as 5 min post-injection, observed in both the MIP images and time-activity curves, clearly highlighting renal clearance capabilities of both $^{89}$Zr-labeled cRGDY-PEG-C' dots probes.

In Vivo Pharmacokinetics and Radiation Dosimetry Studies.

Figure 5A:
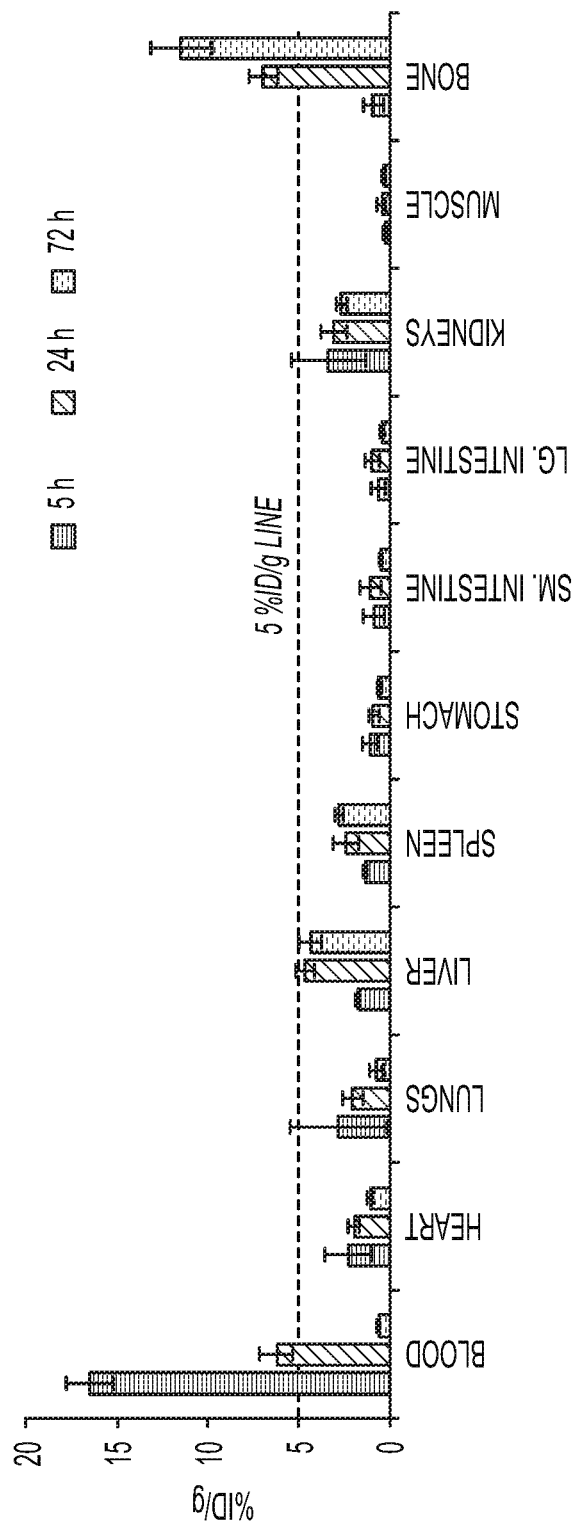
FIGS. 5A-5C are graphs depicting biodistribution studies in mice for chelator-free and chelator-based $^{89}$Zr-labeled C' dots.
Figure 5B:
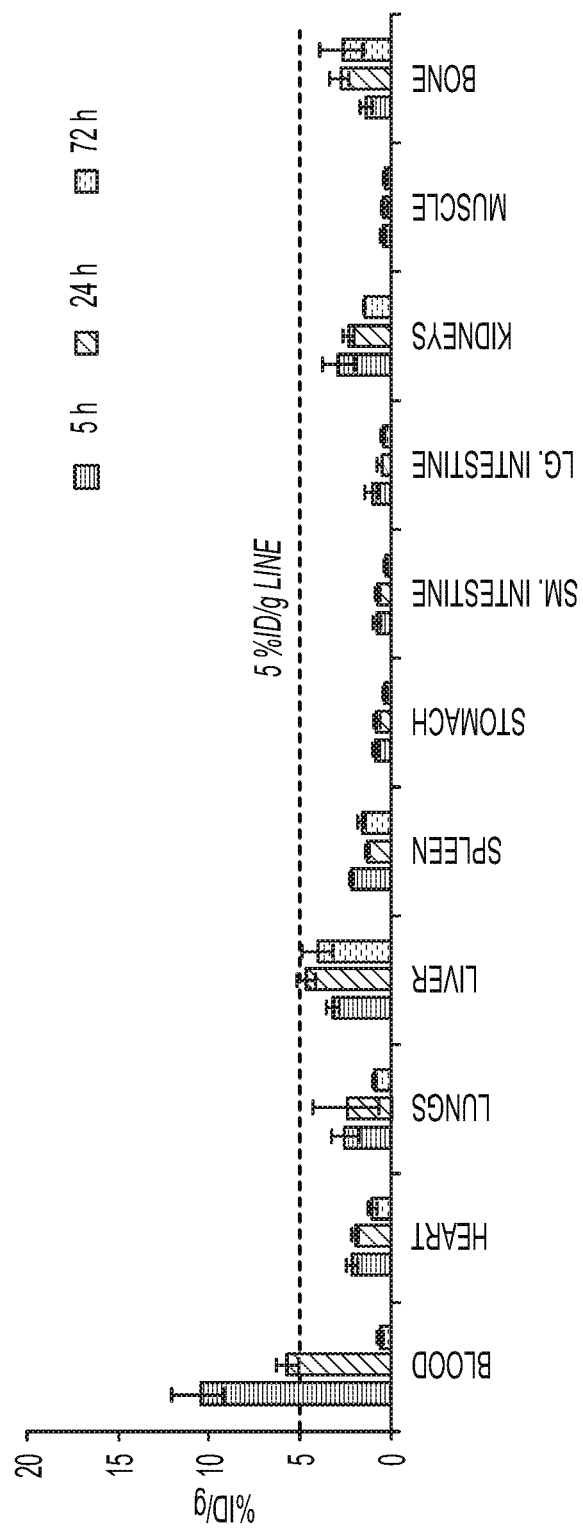
Figure 5C:
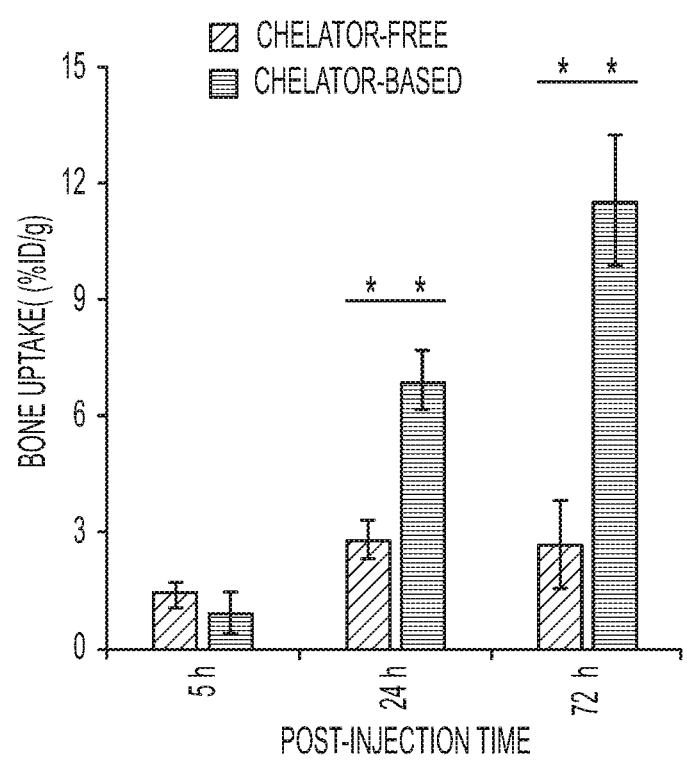
Figure 7:
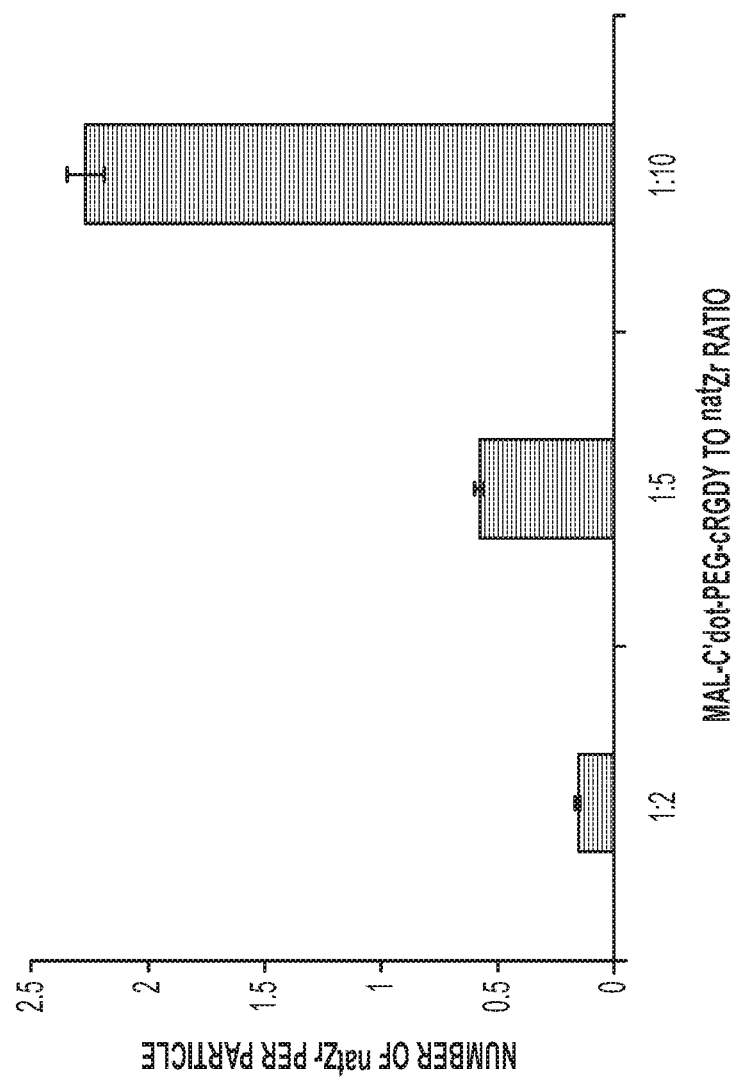
FIG. 7 is a graph depicting an estimation of the number of $^{nat}$Zr per Mal-cRGDY-PEG-C' dots by using MP-AES.

Detailed biodistribution studies were performed to investigate the uptake of both $^{89}$Zr-labeled cRGDY-PEG-C' dots in major organs by sacrificing mice at various post-injection time points and harvesting, weighing, and assaying the organs of interest (i.e., 5, 24 and 72 h, Tables 5 and 6, FIGS. 5A-5C).

Table 5 shows organ uptake of mice injected with cRGDY-PEG-[$^{89}$Zr]C' dots at varied post-injection time points.

TABLE 5

| Chelator-free (n = 3, % ID g ± SD) | | | |
|---|---|---|---|
| Organ | 5 h | 24 h | 72 h |
| Blood | 16.5 ± 1.3 | 6.3 ± 0.9 | 0.7 ± 0.1 |
| Heart | 2.3 ± 1.3 | 2.0 ± 0.3 | 1.1 ± 0.1 |
| Lungs | 2.8 ± 2.1 | 2.1 ± 0.6 | 0.8 ± 0.4 |
| Liver | 1.8 ± 0.1 | 4.7 ± 0.5 | 4.4 ± 0.6 |
| Spleen | 1.4 ± 0.1 | 2.4 ± 0.7 | 2.8 ± 0.2 |
| Stomach | 1.1 ± 0.4 | 0.9 ± 0.3 | 0.6 ± 0.1 |
| Sm. Int. | 0.9 ± 0.6 | 1.1 ± 0.6 | 0.5 ± 0.1 |
| Lg. Int. | 0.6 ± 0.4 | 1.0 ± 0.4 | 0.4 ± 0.0 |
| Kidneys | 3.4 ± 2.0 | 3.1 ± 0.7 | 2.7 ± 0.3 |
| Muscle | 0.3 ± 0.1 | 0.5 ± 0.2 | 0.3 ± 0.1 |
| Bone | 0.9 ± 0.5 | 6.9 ± 0.8 | 11.5 ± 1.7 |

Table 6 shows organ uptake of mice injected with $^{89}$Zr-DFO-cRGDY-PEG-C' dots at varied post-injection time points.

TABLE 6

| Chelator-based (n = 3, % ID g ± SP) | | | |
|---|---|---|---|
| Organ | 5 h | 24 h | 72 h |
| Blood | 10.6 ± 1.4 | 5.7 ± 0.6 | 0.6 ± 0.2 |
| Heart | 2.1 ± 0.3 | 2.0 ± 0.1 | 1.0 ± 0.2 |
| Lungs | 2.5 ± 0.7 | 2.5 ± 1.8 | 0.9 ± 0.0 |
| Liver | 3.2 ± 0.4 | 4.7 ± 0.5 | 4.0 ± 0.9 |
| Spleen | 2.1 ± 0.1 | 1.3 ± 0.1 | 1.6 ± 0.2 |
| Stomach | 0.9 ± 0.1 | 0.8 ± 0.2 | 0.3 ± 0.1 |
| Sm. Int. | 0.8 ± 0.2 | 0.8 ± 0.1 | 0.3 ± 0.0 |
| Lg. Int. | 1.1 ± 0.3 | 0.6 ± 0.1 | 0.4 ± 0.1 |
| Kidneys | 2.9 ± 0.9 | 2.3 ± 0.3 | 1.4 ± 0.0 |
| Muscle | 0.4 ± 0.1 | 0.4 ± 0.1 | 0.3 ± 0.0 |
| Bone | 1.4 ± 0.3 | 2.8 ± 0.5 | 2.7 ± 1.1 |

Figure 10:
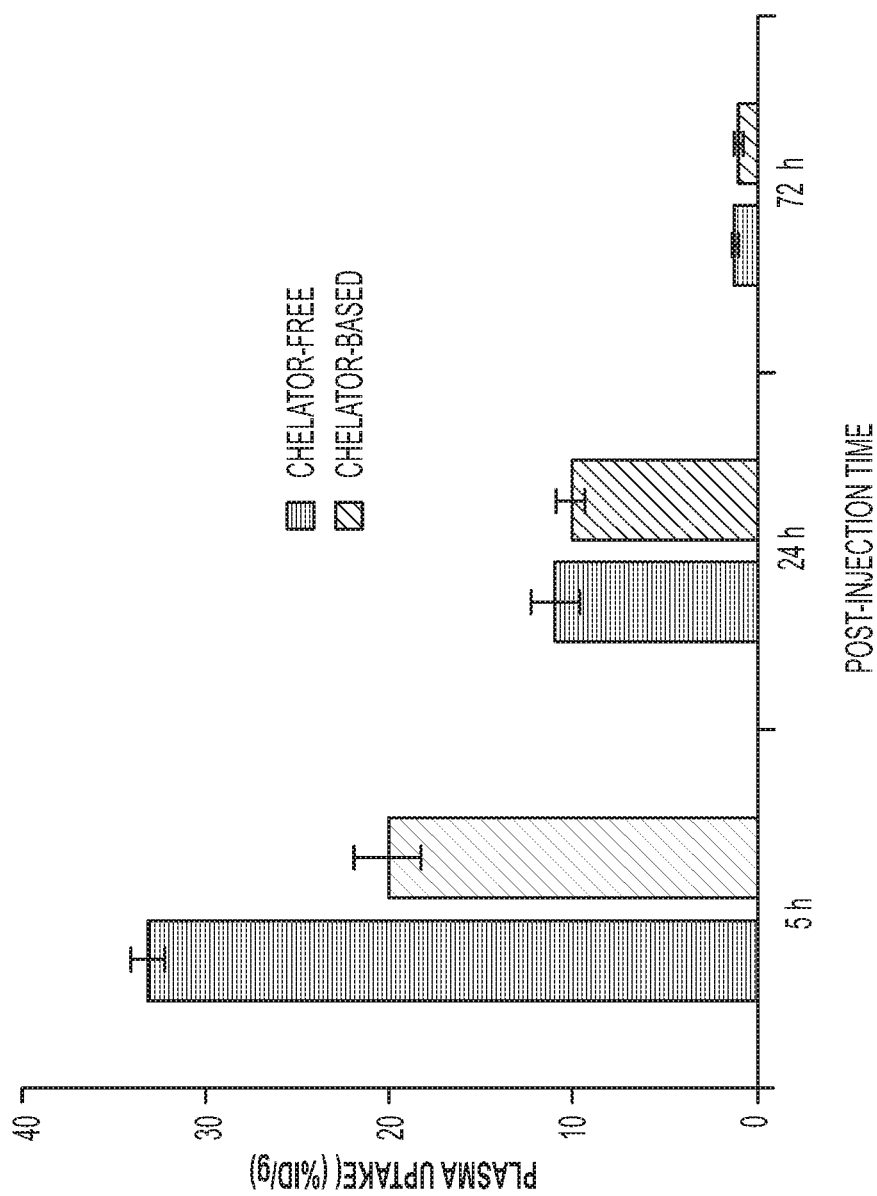
FIG. 10 is a graph depicting the uptake of $^{89}$Zr-labeled cRGDY-PEG-C' dots in mouse plasma at various post-injection time points (n=3).
Figure 11:
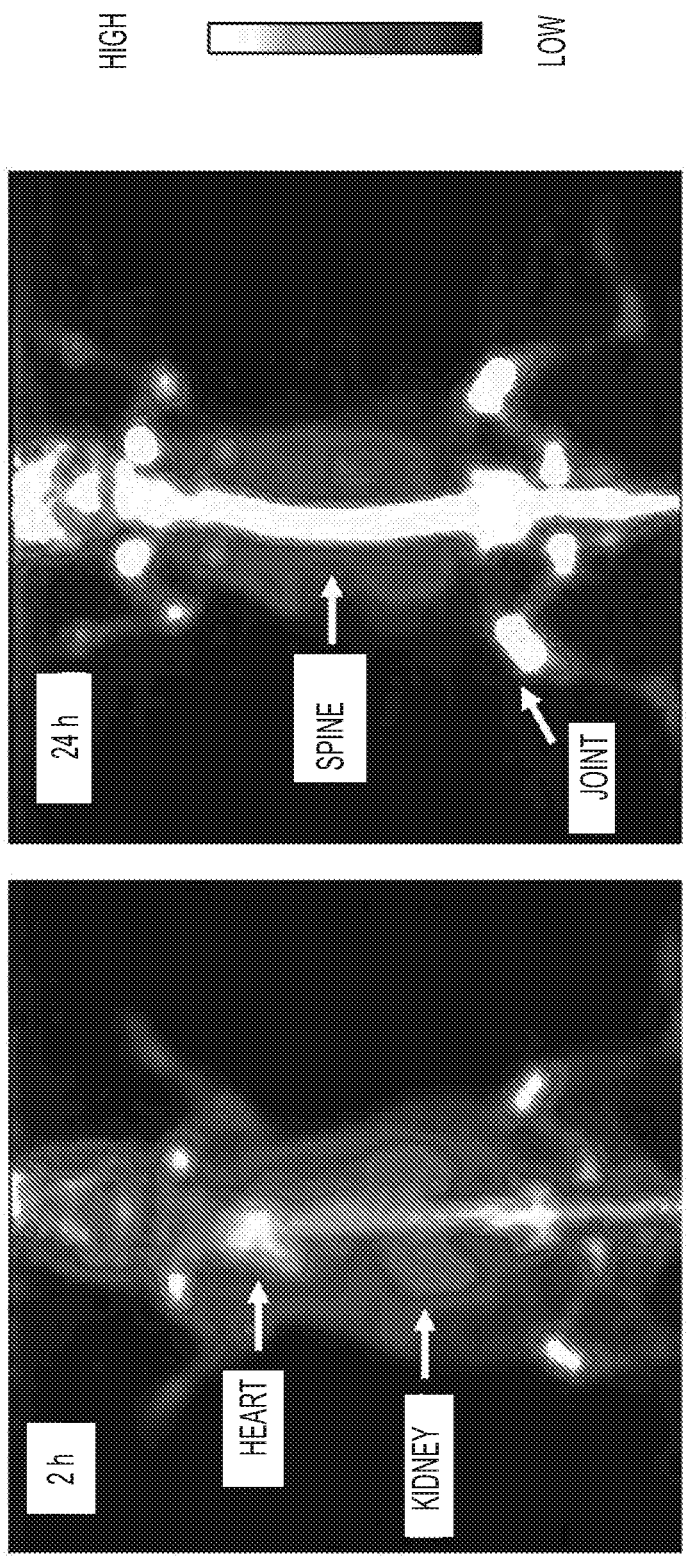
FIG. 11 are images depicting MIP images of free $^{89}$Zr-oxalate in a representative healthy mouse showing the fast and retained isotope uptake in mouse bone and joints.

As evidenced in the dynamic PET imaging studies (FIGS. 4A-4D), the biodistribution studies confirmed significant activity of both $^{89}$Zr-labeled cRGDY-PEG-C' dots probes in the blood compartment (FIGS. 5A and 5B). Plasma activity concentrations were twice as high as those for whole blood (FIG. 10). Urine uptake at the early post-injection time points varied from mouse to mouse, ranging from less than 10% ID/g to greater than 20% ID/g. A total of 60-70% ID of $^{89}$Zr-labeled cRGDY-PEG-C' dots probes were cleared within 72 h post-injection in the current study. As opposed to representative findings for greater than 10 nm sized nanoparticles, usually revealing marked hepatic uptake (e.g., 30-99% ID) uptake, both $^{89}$Zr-labeled cRGDY-PEG-C' dots probes exhibited significantly lower hepatic uptake (less than 5% ID/g or 2-5% ID). Interestingly, when compared with alternative renally clearable particles, such as ultrasmall quantum dots or Au nanoparticles $^{89}$Zr-labeled cRGDY-PEG-C' dots also showed significantly reduced (5-10 fold less) kidney uptake (e.g., 2-4% ID/g, as shown in FIG. 5A-5C) at the early post-injection time points.

Figure 12C:
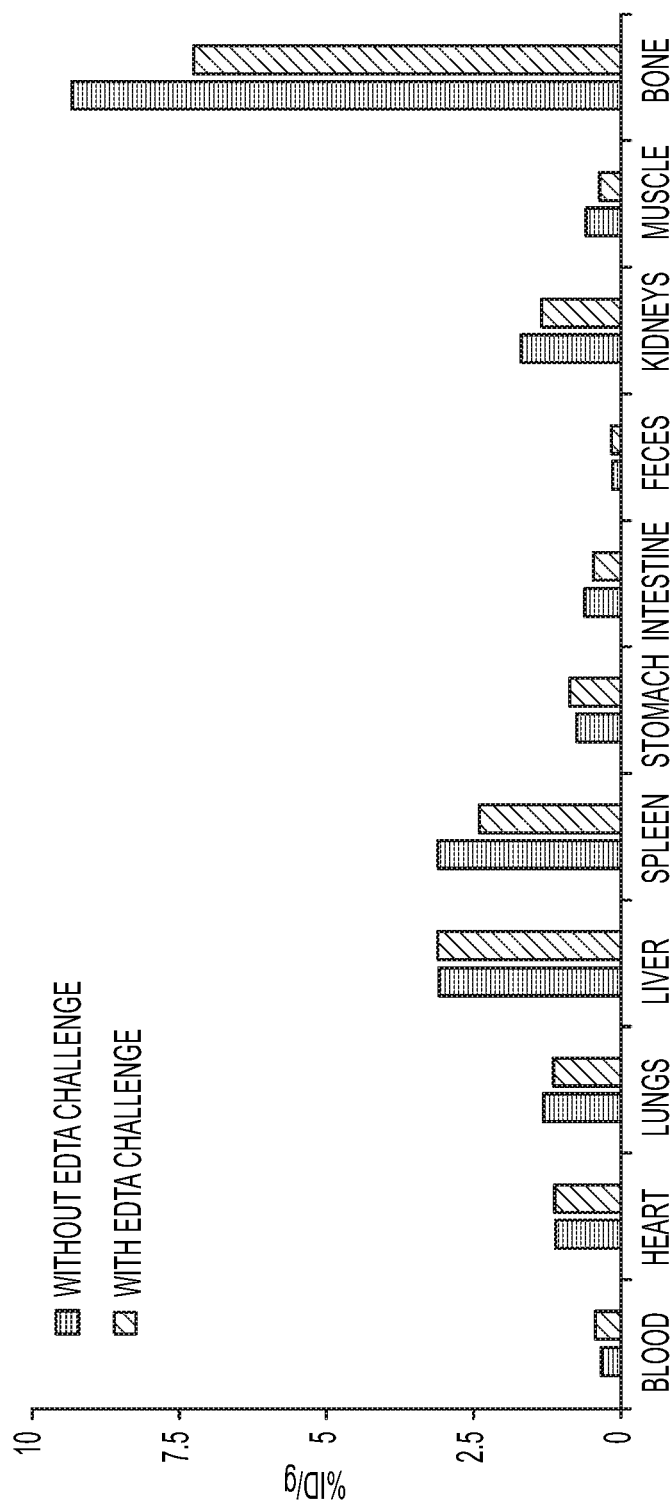
FIG. 12C shows a plot depicting biodistributions results for representative mice. Only ~20% bone uptake reduction was observed. EDTA challenge conditions were 10 mM EDTA, 37° C., and overnight shaking at 650 rpm.
Figure 13:
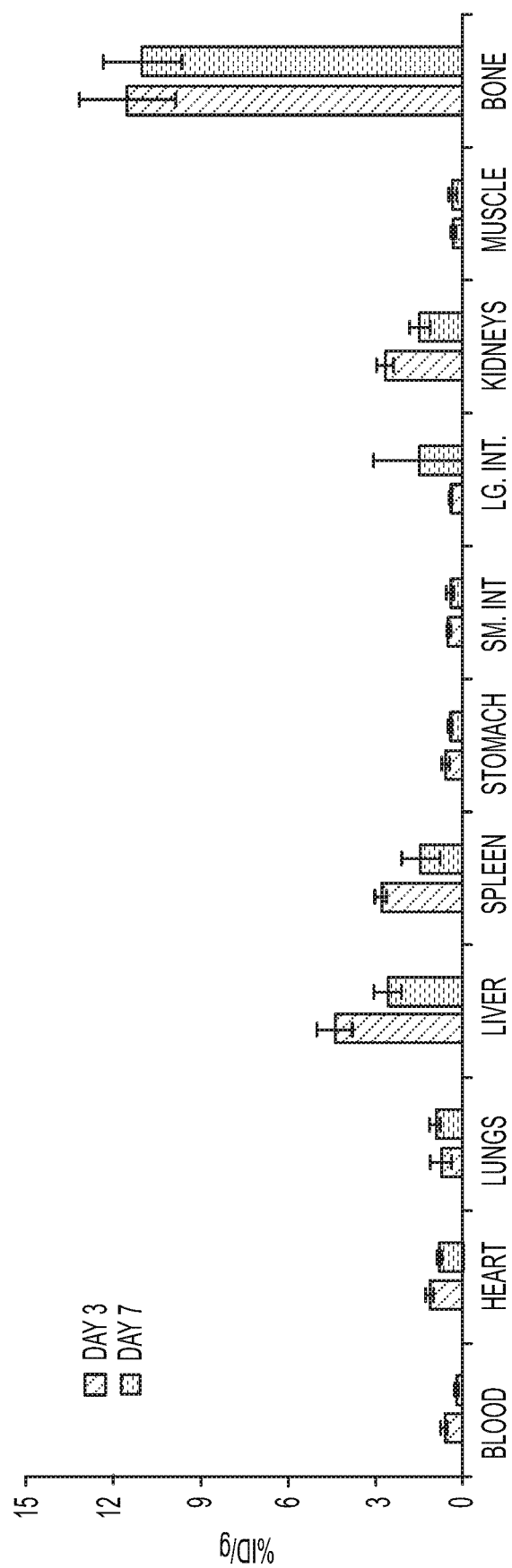
FIG. 13 shows a graph depicting a biodistribution results showing time-dependent changes in chelator-free $^{89}$Zr-labeled cRGDY-PEG-C' dots on days 3 and 7 post-injection, along with marked retained uptake in bone as well as reduced uptake in liver, spleen and kidney (n=3).

A noticeable difference in overall bone uptake was found between the two $^{89}$Zr-labeled cRGDY-PEG-C' dots probes. Values started to increase beyond 5 and 10% ID/g at the 24 h and 72 h post i.v. injection time points, respectfully, for cRGDY-PEG-[$^{89}$Zr]C' dots (as shown in FIG. 5C, p<0.005). Such high bone uptake likely does not reflect marrow accumulation of cRGDY-PEG-[$^{89}$Zr]C' dots probes, but rather indicates ongoing detachment of the free $^{89}$Zr$^{4+}$ from the cRGDY-PEG-[$^{89}$Zr]C' dots due to relatively low radio-stability in vivo (FIG. 3B). Free $^{89}$Zr$^{4+}$ is an osteophilic cation which could be readily accreted into bone mineral, as shown in FIG. 10. Monitoring the change in bone uptake over time has also been demonstrated as one of the best ways to study the in vivo stability of $^{89}$Zr-labeled nanoprobes. Attempts to reduce the bone uptake of cRGDY-PEG-[$^{89}$Zr] C' dots by removing the less well-chelated surface $^{89}$Zr from cRGDY-PEG-[$^{89}$Zr]C' dots using EDTA challenge prior to injection was demonstrated to be only marginally effective in minimizing bone uptake. Only ~20% bone uptake reduction was observed even after overnight EDTA challenge (conditions: 10 mM EDTA, 37° C., shaking at 650 rpm, FIG. 12C). PET imaging in FIG. 12B reveals apparent and persistent bone and joint uptake of cRGDY-PEG-[$^{89}$Zr]C' dots that were subjected to an additional EDTA challenge process. Moreover, the clearance of $^{89}$Zr from the bones of mice was found to be slow with no significant reduction after one week (FIG. 13). The excess and retained accumulation of radioactive $^{89}$Zr$^{4+}$ in the bone can increase the radiation dose to this compartment (an especially radiosensitive tissue), potentially hindering clinical translation.

To estimate mean organ absorbed doses and the effective dose in a 70-kg standard man, dosimetry calculations for both $^{89}$Zr-labeled cRGDY-PEG-C' dots probes were performed based on the biodistribution data shown in FIGS. 5A-5C and using the OLINDA computer program (yielding doses expressed in mSv/MBq). Table 7 compares the estimated tissue absorbed dose in humans for both $^{89}$Zr-labeled cRGDY-PEG-C' dots probes. Table 7 shows radiation dosimetry of $^{89}$Zr-labeled cRGDY-PEG-C' dots in a 70-kg standard man estimated by using OLINDA dosimetry program.

TABLE 7

| Tissue | Chelator-free Absorbed Dose (mSv/MBq) | Chelator-based Absorbed Dose (mSv/MBq) |
|---|---|---|
| Adrenals | 0.101 | 0.080 |
| Brain | 0.079 | 0.062 |
| Breasts | 0.068 | 0.055 |
| Gallbladder Wall | 0.102 | 0.081 |
| Lower Large Intestine Wall | 0.108 | 0.114 |
| Small Intestine | 0.108 | 0.103 |
| Stomach Wall | 0.112 | 0.116 |
| Upper Large Intestine | 0.099 | 0.100 |
| Heart Wall | 0.139 | 0.089 |
| Kidneys | 0.205 | 0.135 |
| Liver | 0.100 | 0.073 |
| Lungs | 0.088 | 0.081 |
| Muscle | 0.060 | 0.051 |
| Ovaries | 0.103 | 0.094 |
| Pancreas | 0.114 | 0.101 |
| Red Marrow | 0.084 | 0.062 |
| Bone | 0.084 | 0.087 |
| Skin | 0.052 | 0.042 |
| Spleen | 0.242 | 0.395 |
| Testes | 0.081 | 0.069 |
| Thymus | 0.082 | 0.063 |
| Thyroid | 0.072 | 0.058 |
| Urinary Bladder Wall | 0.441 | 0.446 |
| Uterus | 0.129 | 0.118 |
| Total Body | 0.076 | 0.062 |
| Effective Dose | 0.113 | 0.102 |

A slightly higher absorbed dose (0.084 mSv/MBq) in red marrow was found for the chelator-free $^{89}$Zr-labeled cRGDY-PEG-C' dot, when compared with that of chelator-based cRGDY-PEG-[$^{89}$Zr]C' dots (0.062 mSv/MBq). An absorbed dose ~0.1 mSv/MBq was estimated for both $^{89}$Zr-labeled cRGDY-PEG-C' dots probes in the human liver, only one-tenth of a previously reported value for $^{89}$Zr-DFO-trastuzumab (liver uptake was ~12% ID, average estimated absorbed dose in liver was 1.54 mSv/MBq). Although significantly higher bone uptake was observed in the small animal study, the estimated radiation dosimetry in a 70-kg standard man showed only a minor increase (less than 20%) in both the total-body and effective dose for the chelator-free $^{89}$Zr-labeled cRGDY-PEG-[$^{89}$Zr]C' dots product. Taken together, in vivo pharmacokinetic studies confirmed the renal clearance and extended blood circulation of $^{89}$Zr-labeled cRGDY-PEG-C' dots probes within the first 24 h post-injection. All major organs, especially liver, spleen and kidney, showed very minor (less than 5% ID/g) uptake throughout the study period. A major difference between the chelator-free and the chelator-based $^{89}$Zr-labeled cRGDY-PEG-C' dots probes is the lower in vivo radiostability and significantly higher (2-4 fold) bone uptake of the former at 24 h post-injection. However, the radiation dosimetry analysis showed favorable total-body and effective doses for both $^{89}$Zr-labeled cRGDY-PEG-C' dots probes, which encouraged exploration of the in vivo tumor-specific targeting of both radio-labeled nanoprobes in well-characterized integrin $\alpha_v\beta_3$ expressing human melanoma xenograft models.

In Vivo Tumor-Targeting by PET Imaging.

As described herein, designing a "target-or-clear" multi-functional nanoparticle platform which actively locates in the target-of-interest after systemic administration while maintaining a low non-specific accumulation in the reticuloendothelial system (RES) has long been one of the major challenges in the field of nanomedicine. Table 1 lists the current research status of ultrasmall nanoparticles exhibiting both renal clearance and in vivo active tumor-targeting capabilities.

As shown in FIGS. 6A-6J, significant bladder activity was observed in the 2 h maximum intensity projection (MIP) images for mice injected with [$^{89}$Zr]cRGDY-PEG-C' dots (FIG. 6A) and $^{89}$Zr-DFO-cRGDY-PEG-C' dots (FIG. 6B, 6C). The high cardiac uptake observed (~20% ID/g) clearly indicated the circulation of $^{89}$Zr-labeled cRGDY-PEG-C' dots in the blood compartment. The time-activity curves shown in FIGS. 6D-6F depict the clearance of $^{89}$Zr-labeled cRGDY-PEG-C' dots in the blood with uptake values estimated to be about 5-6% ID/g and 1-2% ID/g at 24 h and 72 h post-injection, respectively. The clearance of $^{89}$Zr-labeled cRGDY-PEG-C' dots by the RES organs (e.g., liver) was estimated to be only 5-6% ID/g at 2 h post-injection, with slight reductions down to 4-5% ID/g after 3 days; these values are marked lower than previously reported values for particles larger than 10 nm. Splenic uptake was found to be only half of that found for liver uptake over the course of 3 days. Muscle uptake was found to be as low as ~1% ID/g. Without wishing to be bound to any theory, such dominant renal clearance, significantly reduced RES uptake, very low background activity levels in muscle, and suitable blood circulation half-times of ~15 h, suggest that significantly enhanced tumor-to-background ratio may therefore be achievable.

Figures 14A, 14B:
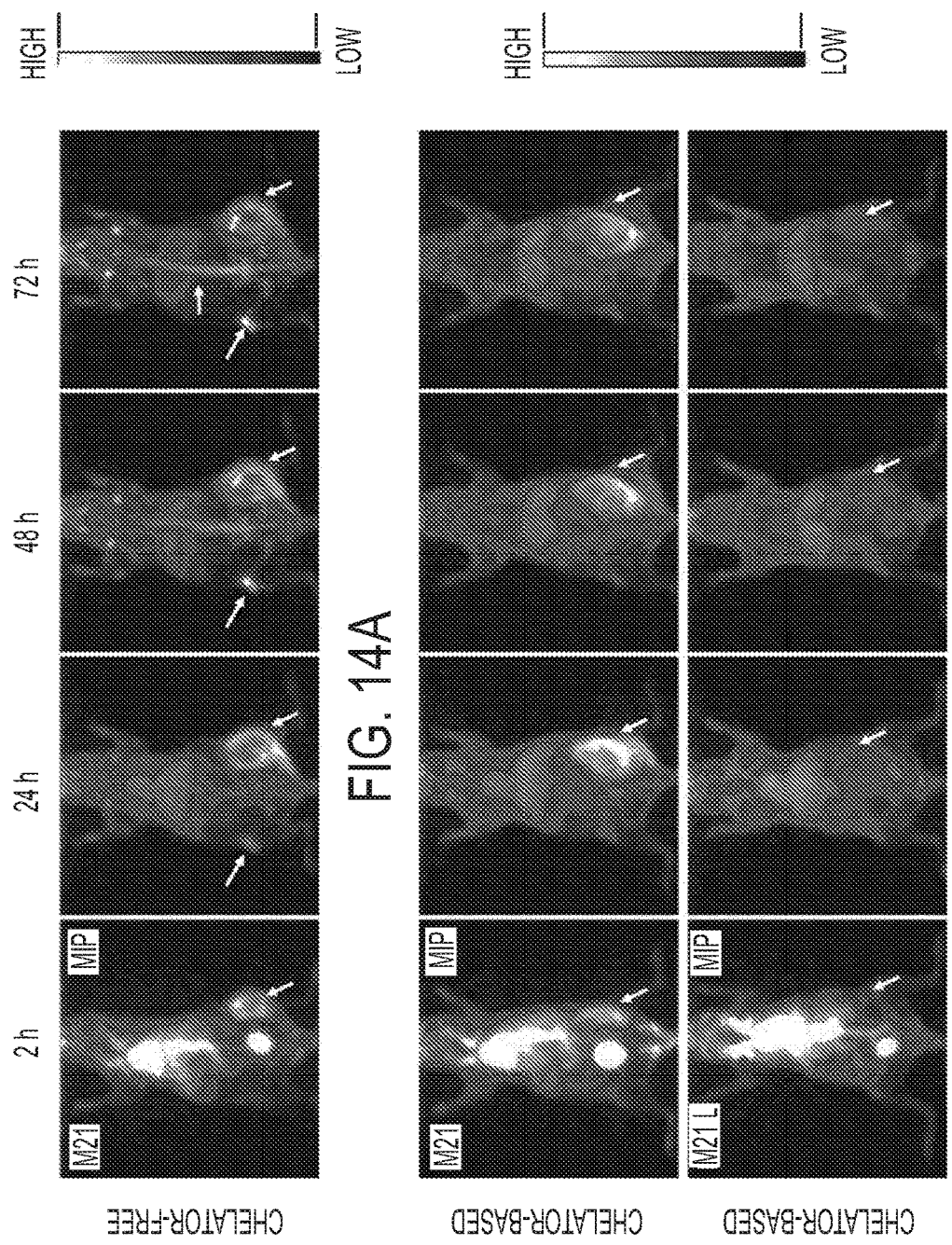
FIGS. 14A and 14B are images showing coronal MIP PET images of tumor-bearing mice injected with (FIG. 14A) chelator-free and (FIG. 14B) chelator-based $^{89}$Zr-labeled cRGDY-PEG-C' dots at various post-injection time points. Tumors are marked with yellow arrows. Bone and joint uptake are marked with white arrows.

As shown in FIGS. 6A-6B, high M21 ($\alpha_v\beta_3$ positive) tumor uptake was observed in mice injected with both cRGDY-PEG-[$^{89}$Zr]C' dots (FIG. 6A, 10.1±2.1% ID/g) and $^{89}$Zr-DFO-cRGDY-PEG-C' dots (FIG. 6B, 10.5±4.0% ID/g) at 2 h post-injection. The tumor uptake peaked at 24 h post-injection with an additional slight increase to about 10.7±1.3% ID/g and 12.0±1.4% ID/g, respectively (FIG. 6G). Over 5-fold enhancement of tumor uptake was estimated when compared with first-generation C dots (cRGDY ligand density: ~6) labeled with $^{124}$I (maximal M21 tumor uptake: ~2% ID/g at 4 h post-injection). Retention of particle activity (with only a low wash-out rate) over the 72 h time period tested was observed in M21 tumor-bearing mice injected with both types of $^{89}$Zr-labeled cRGDY-PEG-C' dots (FIGS. 6D and 6E). Mice injected with the chelator-free $^{89}$Zr-labeled cRGDY-PEG-C' dots showed detachment of free $^{89}$Zr and with its accumulation in bone, joint, and spine (FIGS. 6A, 14A-14B), while significantly reduced bone and joint uptake was found in mice injected with $^{89}$Zr-DFO-cRGDY-PEG-C' dots (FIGS. 6B, 14A-14B).

Figure 15:
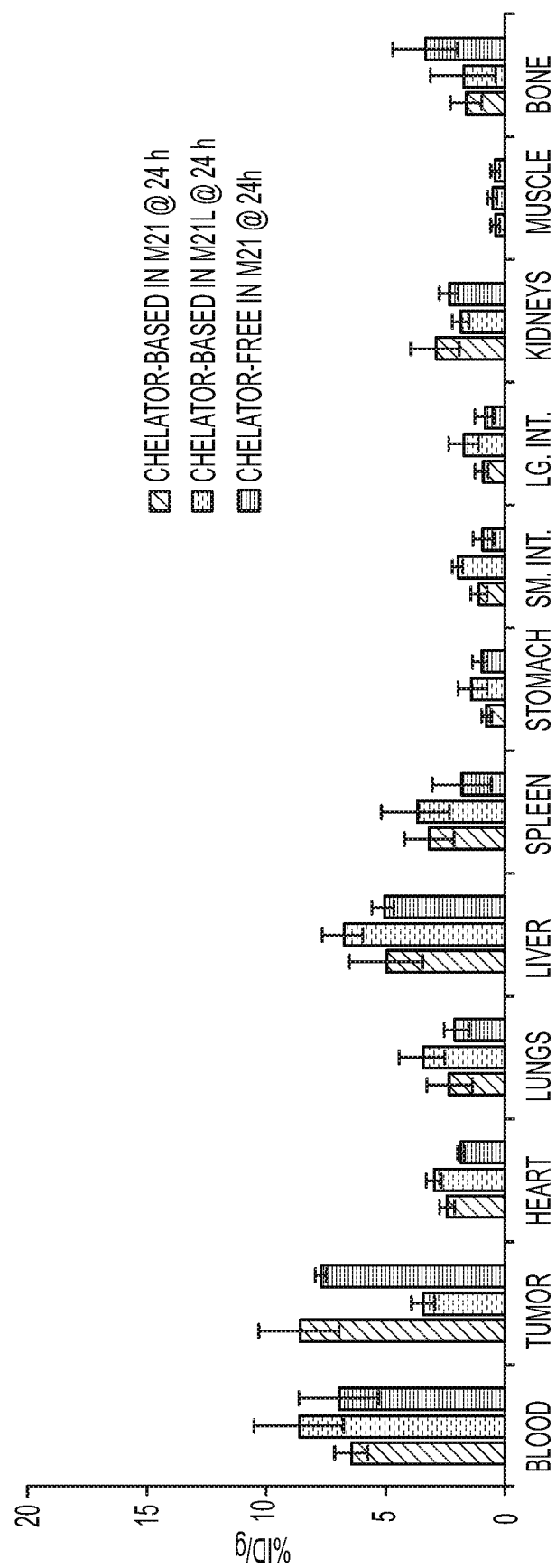
FIG. 15 is a plot showing ex vivo biodistribution studies of $^{89}$Zr-labeled cRGDY-PEG-C' dots in M21 and M21-L tumor-bearing mice at 24 h post-injection (n=3).

A control study was performed in M21-L tumor-bearing mice ($\alpha_v\beta_3$-negative) following injection of $^{89}$Zr-DFO-cRGDY-PEG-C' dots to further demonstrate target specificity of $^{89}$Zr-labeled cRGDY-PEG-C' dots. Findings showed similar particle distributions in major organs, such as bladder, heart, liver and muscle, with significantly lower uptake in the M21-L tumors (on average 2-3% ID/g), as shown in FIGS. 6C, 6F and 15. No significant differences were found in the absolute tumor uptake values or in the tumor-to-organ ratios for mice injected either with cRGDY-PEG-[$^{89}$Zr]C' dots or $^{89}$Zr-DFO-cRGDY-PEG-C' dots (FIGS. 6G-6J, 15). For mice injected with $^{89}$Zr-DFO-cRGDY-PEG-C' dots, the highest tumor-to-blood and tumor-to-muscle ratios were estimated to be 6.4±2.6 and 9.6±2.5 at 72 h post-injection, respectively, which are 3- to 4-fold higher than the corresponding ratios in the M21-L tumor-bearing mice (tumor-to-blood: 1.5±0.6; tumor-to-muscle: 2.8±0.7, FIGS. 6H and 6J). Finally, on the basis of high tumor uptake and low RES accumulation, about (or greater than) 2 or higher tumor-to-liver ratio was observed in M21 tumor-bearing mice injected with cRGDY-PEG-[$^{89}$Zr]C' dots or $^{89}$Zr-DFO-cRGDY-PEG-C' dots (FIG. 6I), which is one of the unique features distinguishing $^{89}$Zr-labeled cRGDY-PEG-C' dots probes from other tumor targeting nanoparticles. Taken together, renal clearance and in vivo specific active targeting of $^{89}$Zr-labeled cRGDY-PEG-C' dots in the $\alpha_v\beta_3$ integrin-expressing melanoma xenograft models were demonstrated.

To address the challenges in the radiolabeling of ultrasmall renally clearable cRGDY-PEG-C' dots, two $^{89}$Zr-radiolabeling strategies were developed and compared based on their biological and dosimetry properties. Although comparable in vitro radiostability was found for both nanoprobes, chelator-based radiolabeling showed a significantly higher in vivo radiostability than chelator-free preparations. Both PK studies and PET imaging evaluations confirmed renal clearance, low RES accumulation, enhanced tumor uptake and high target-to-background ratios for both products were observed non-invasively in $\alpha_v\beta^3$ integrin-expressing melanoma xenograft models. All these suggest a favorable translatability of these novel "target-or-clear" $^{89}$Zr-labeled cRGDY-PEG-C' dots tracers to human subjects for systemic targeted imaging (or treatment) of cancer.

Synthesis, Purification and Characterization of cRGDY-PEG-C' Dots and Amine-Functionalized NH$_2$-cRGDY-PEG-C' dots.

The synthesis of cRGDY-PEG-C' dots followed a known protocol (see, e.g., U.S. application Ser. No. 14/215,879, published as U.S. Publication No. US20140248210A1, the contents of which is hereby incorporated by reference in its entirety), while the synthesis of NH$_2$-cRGDY-PEG-C' dots used a post-PEGylation surface modification by insertion approach (Ma, K.; Wiesner, U., Modular and Orthogonal Post-PEGylation Surface Modifications by Insertion Enabling Penta-functional Ultrasmall Organic-Silica Hybrid Nanoparticles *J. Am. Chem. Soc.* 2017, Submitted, the contents of which is hereby incorporated by reference in its entirety). Remaining silanol groups on NH$_2$-cRGDY-PEG-C' dots after PEGylation were further terminated by adding diethoxydimethylsilane (DEDMS) to the synthesis at 7.3 mM concentration under vigorous stirring. The reaction solution was left at room temperature under vigorous stirring overnight, followed by particle purification. The rest of the synthesis of the aminated particles followed a similar protocol to that of the cRGDY-PEG-C' dots. Purification and characterization methods for different C' dots, including GPC purification, as well as TEM, FCS and UV-vis measurements, are described herein.

One-Pot Synthesis of DFO-cRGDY-PEG-Cy5-C' dots

Moreover, the synthesis of cRGDY-PEG-C' dots and/or NH$_2$-cRGDY-PEG-C' dots can be made using a one-pot synthesis technique, as shown, for example, in FIG. 17. In chemistry a one-pot synthesis technique can improve the efficiency of a chemical reaction. For instance, one or more reactants are subjected to successive chemical reactions in just one reactor, thereby improving efficiency of the chemical reaction. As depicted in the schematic in FIG. 17, cRGDY-C' dots are contacted with amine-silane to create amine-cRGDY-C' dots. amine-cRGDY-C' dots are then contacted, in the same "pot" with DFO-NCS to generate DFO-cRGDY-C' dots.

DFO-cRGDY-PEG-Cy5-C' dots were produced using a one-pot water-based synthesis protocol (e.g., as shown in FIG. 17). 17.2 µmol of NHS ester/maleimido functionalized heterofunctional polyethylene glycol (PEG), referred to as mal-PEG-NHS, was first dissolved in 74.5 µL of dimethyl sulfoxide (DMSO), and then mixed with 15.5 µmol of (3-aminopropyl)triethoxysilane (amine-silane) at room temperature under nitrogen. The reaction mixture was then left at room temperature under nitrogen for two days to conjugate mal-PEG-NHS with amine-silane via NHS ester-amine reaction, forming mal-PEG-silane conjugate. Afterwards, 18.9 µmol of cyclo(Arg-Gly-Asp-D-Tyr-Cys) peptide (cRGDY) was dissolved in 900 µL DMSO, and then added into the reaction solution of mal-PEG-silane at room temperature under nitrogen. The reaction mixture was then left at room temperature under nitrogen overnight to further conjugate mal-PEG-silane with the thiol group on the cysteine residue of cRGDY peptide through thiol-ene reaction, forming cRGDY-PEG-silane conjugate. At the same time, 1.3 µmol of maleimido functionalized Cy5 dye (Cy5-mal) was first dissolved in 100 µL DMSO, and then mixed with 28.4 µmol of (3-mercaptopropyl)trimethoxysilane (thiol-silane) to conjugate Cy5-mal with thiol-silane through thiol-ene reaction, forming Cy5-silane conjugate.

In the next step, 204 µL of tetramethyl orthosilicate (TMOS liquid) and all the Cy5-silane conjugate, which was prepared in the previous step, were added into 30 mL of aqueous solution of ammonium hydroxide, for which the ammonium hydroxide concentration was 0.006M, at room temperature under vigorous stirring. The reaction solution was left at room temperature under vigorous stirring overnight to generate silica nanoparticles via silane hydrolysis and condensation, in which Cy5 dyes were covalently encapsulated. Next, the cRGDY-PEG-silane conjugate, which was prepared in the previous step, was added into the reaction mixture at room temperature under vigorous stirring, followed by the addition of 300 µL of silane functionalized monofunctional PEGs (PEG-silane liquid). Afterwards, the reaction solution was left at room temperature overnight under vigorous stirring. The reaction solution was then left at 80'C statically overnight to further enhance the covalent attachment of PEG-silane and cRGDY-PEG-silane to the silica nanoparticle surface via silane condensation. After cooling the reaction solution to room temperature, the silica nanoparticles were well PEGylated, forming cRGDY-PEG-Cy5-C' dots.

Next, 8.6 µmol of (3-aminopropyl)trimethoxysilane (amine-silane) was further added into the reaction solution of cRGDY-PEG-Cy5-C' dots at room temperature under vigorous stirring. The reaction solution was then left at room temperature overnight under vigorous stirring to further covalently attach the amine-silane molecules to the remaining silanol groups on the silica surface of cRGDY-PEG-Cy5-C' dots under the PEG layer via silane hydrolysis and condensation. Afterwards, 17 µmol of N-chlorosuccinimide functionalized deferoxamine (DFO-NCS) was first dissolved in 750 µL DMSO and then added into the reaction solution at room temperature under vigorous stirring. The reaction solution was then left at room temperature overnight under vigorous stirring to covalently attach DFO-NCS to the amine groups under the PEG layer of C' dots via NCS-amine reaction, resulting in around 4 DFO molecules per particle. The DFO-cRGDY-PEG-Cy5-C' dots were purified by GPC, filtered by sterile syringe filters and stored at 4° C. The DFO-cRGDY-PEG-Cy5-C' dots were then radiolabeled with $^{89}$Zr, forming $^{89}$Zr-DFO-cRGDY-PEG-Cy5-C' dots.

Further description of methods of making functionalized aminated nanoparticles are described in Wiesner et al., U.S. Patent Application No. 62/508,703, filed on May 19, 2017, the contents of which is hereby incorporated by reference in its entirety. $^{89}$Zr-oxalate production.

$^{89}$Zr was produced at Memorial Sloan Kettering Cancer Center on a TR19/9 cyclotron (Ebco Industries Inc.) via the $^{89}$Y(p,n)$^{89}$Zr reaction and purified to yield $^{89}$Zr with a specific activity of 5.28-13.43 mCi/µg (470-1195 Ci/mmol) of zirconium. Activity measurements were performed using a CRC-15R Dose Calibrator (Capintec). For the quantification of activities, experimental samples were counted on an Automatic Wizard$^2$ γ-Counter (PerkinElmer). All in vivo experiments were performed according to protocols approved by the Memorial Sloan Kettering Institutional Animal Care and Use Committee (Protocol #86-02-020). A purity of greater than 95% was confirmed using radio-TLC for all of the $^{89}$Zr-labeled cRGDY-PEG-C' dots.

Chelator-Free $^{89}$Zr Radiolabeling of cRGDY-PEG-C' dots.

For a chelator-free $^{89}$Zr labeling of cRGDY-PEG-C' dots, 4 nmol of cRGDY-PEG-C' dots (surface functionalized with maleimide groups) were mixed with 1 mCi of $^{89}$Zr-oxalate in HEPES buffer (pH 8) at 75° C. The radiolabeling yield of cRGDY-PEG-C' dots were monitored using salicylic acid impregnated instant thin-layer chromatography paper (ITLCSA) (Agilent Technologies) and analyzed either on a Bioscan AR-2000 radio-TLC plate reader using Winscan Radio-TLC software (Bioscan Inc., Washington, D.C.), or an Automatic Wizard$^2$ γ-Counter (PerkinElmer). After incubation, 5 µL aliquots were withdrawn and mixed with 50 µL of EDTA (50 mM, pH 5-6) before analyzing by ITLC using EDTA (50 mM, pH 5-6) as a mobile phase solvent. Free $^{89}$Zr forms an instantaneous complex with EDTA and eluted with the solvent from, while $^{89}$Zr-labeled cRGDY-PEG-C' dots remained at the origin. For more accurate quantification, the strips were cut in half, and the γ-rays emissions at 909 keV were counted on a calibrated γ-counter (PerkinElmer) using a dynamic energy window of 800-1000 keV. Similar procedures were introduced when studying the pH-, concentration- and temperature-dependent chelator-free labeling of cRGDY-PEG-C' dots. The specific activity of chelator-free $^{89}$Zr-labeled cRGDY-PEG-C' dots were found in the range of 100-500 Ci/mmol.

Synthesis and Chelator-Based $^{89}$Zr Labeling of DFO-cRGDY-PEG-C' Dots.

A chelator-based $^{89}$Zr labeling technique was introduced by reacting amine-functionalized NH$_2$-cRGDY-PEG-C' dots with DFO-NCS (molar ratio was 1:20) for 1-2 hours at room temperature, pH 8-9, and shaking at 640 rpm. Synthesized DFO-cRGDY-PEG-C' dots were then purified by passing the particles through a PD-10 column using phosphate-buffered saline (PBS) as the mobile phase. For chelator-based $^{89}$Zr labeling, 0.2-0.75 nmol of DFO-cRGDY-PEG-C' dots were then mixed with 1 mCi of $^{89}$Zr-oxalate in HEPES buffer (pH 8) at 37° C. for 60 min; final labeling pH was kept as 7-7.5. The labeling yield was monitored as described herein. An EDTA challenge process was introduced to remove any non-specifically bound $^{89}$Zr. Synthesized $^{89}$Zr-DFO-cRGDY-PEG-C' dots were then purified by using a PD-10 column. The final radiochemical purity was measured by using ITLC. The specific activity was found to be in the range of 1300-4300 Ci/mmol.

MP-AES Quantification of the Number of $^{nat}$Zr Per DFO-cRGDY-PEG-C' Dots.

To quantify the number of $^{nat}$Zr per DFO-cRGDY-PEG-C' dot, 0.75 nmol of DFO-cRGDY-PEG-C' dots were mixed with excess $^{nat}$ZrCl$_4$ (15 nmol) at 37° C. for 60 min. The final labeling pH was kept at 7-7.5. After labeling, the mixture was combined with EDTA and incubated for more than 30 min to eliminate any non-specific $^{nat}$ZrCl$_4$. The sample was then purified with PD-10 column. The amount of total labeled $^{nat}$Zr was then measured using Microwave Plasma-Atomic Emission Spectroscopy (MP-AES). The number of $^{nat}$Zr per DFO-cRGDY-PEG-C' dots were calculated by the following equation:

$$\text{Number of } ^{nat}Zr \text{ per particle} = \frac{\text{number of } ^{nat}Zr}{\text{number of cRGDY-PEG-C' dot}}$$

Without wishing to be bound to any theory, since excess $^{nat}$ZrCl$_4$ was used for the labeling, the number of $^{nat}$Zr per $^{nat}$Zr-DFO-cRGDY-PEG-C' dots should roughly be equal to the number of accessible DFO per DFO-cRGDY-PEG-C' dots.

Blood Circulation Half-Time Evaluations.

To estimate the blood circulation half-time of both $^{89}$Zr-labeled cRGDY-PEG-C' dots probes, healthy mice (n=3) were injected with intravenously (i.v.) with radioactive particles. Blood sampling was performed at various post-injection time points, and these radioactive samples were counted by using an Automatic Wizard$^2$ γ-Counter (PerkinElmer). Blood uptake values were presented as a percentage of the injected dose per gram (% ID/g), and fit with a two-compartment model.

In Vitro and In Vivo Radio-Stability Studies.

To study the in vitro radio-stability, both chelator-free and chelator-based $^{89}$Zr-labeled cRGDY-PEG-C' dots were kept in PBS (1×) at room temperature. Radiochemical purity was measured over a 1 week period by ITLC at various time points from the end of synthesis (EOS). For in vivo radio-stability, healthy mice were injected with ~200 Ci (~7.4 MBq) of chelator-free (or chelator-based)$^{89}$Zr-labeled cRGDY-PEG-C' dots. Whole blood was collected at 2, 24 and 48 h post-injection, and the plasma fraction was isolated from red blood cells by centrifugation at 8000 rpm for 10 min. The percentage of the intact $^{89}$Zr-labeled cRGDY-PEG-C' dots were then measured by using ITLC with the plates analyzed on a Bioscan AR-2000 radio-TLC plate reader using Winscan Radio-TLC software (Bioscan Inc., Washington, D.C.).

Animal Models and Tumor Inoculation:

All animal experiments were done in accordance with protocols approved by the Institutional Animal Care and Use Committee of Memorial Sloan-Kettering Cancer Center and followed NIH guidelines for animal welfare. M21 and M21-L xenografts were generated by co-injecting equal volumes of cells (~5×10$^6$ cells/100 µL) and Matrigel subcutaneously into the hind legs of female athymic nu/nu mice (6-8 weeks old, Taconic Farms Inc.). Average tumor volumes of 200 mm$^3$ were used for all studies.

Dosimetry.

Time-activity curves derived for each tissue were analytically integrated, accounting for radioactive decay, to yield the corresponding cumulative activity. Organ absorbed doses were then calculated by multiplying the cumulative activity by the $^{89}$Zr equilibrium dose constant for non-penetrating radiations (positrons), assuming complete local absorption of such radiations and ignoring the contribution of penetrating radiations (i.e., γ-rays). Mouse normal organ cumulated activities were converted to human normal organ cumulated activities by taking into account differences in total-body and organ masses between mice and humans (assuming 70-kg standard human). Calculated human normal-organ cumulated activities were entered into the OLINDA dosimetry program to compute standard human organ absorbed doses using formalism of the Medical Internal Dosimetry Committee of the Society of Nuclear Medicine. This human dosimetry model is a "normal" (i.e., tumor-free) anatomic model.

In Vivo Static PET Dynamic PET Imaging and Ex Vivo Biodistribution Studies.

For static PET imaging, tumor-bearing mice (n=3) were i.v. injected with 200-300 µCi (7.4-11.1 MBq) PEG-cRGDY-[$^{89}$Zr]C' dots or $^{89}$Zr-DFO-cRGDY-PEG-C' dots. PET imaging was performed in a small-animal PET scanner (Focus 120 microPET; Concorde Microsystems) at 2, 24, 48, and 72 h post-injection. Image reconstruction and region-of-interest analysis of the PET data were performed by using IRW software with results presented as % ID/g.

For dynamic PET scanning, healthy mice were i.v. injected with ~400 Ci (~14.8 MBq) of C' dot-PEG-cRGDY-[$^{89}$Zr]C' dots or $^{89}$Zr-DFO-cRGDY-PEG-C' dots. A 60-min dynamic scan was performed in a small-animal PET scanner (Focus 120 microPET; Concorde Microsystems) and framed into 46 frames: 12×5 s, 6×10 s, 6×30 s, 10×60 s, 6×150 s, 5×300 s. Image reconstruction, and region of interest (ROI) analysis were performed by using IRW software and presented as % ID/g.

For biodistribution studies, tumor-bearing (n=3) mice were injected with ~100 µCi (~3.7 MBq) C' dot-PEG-cRGDY-[$^{89}$Zr]C' dots or $^{89}$Zr-DFO-cRGDY-PEG-C' dots. Accumulated activity in major intraparenchymal organs were assayed at 24 h using an Automatic Wizard$^2$ γ-Counter (PerkinElmer), and presented as % ID/g (mean±SD).

Statistics.

All comparisons were performed using a two-sample t-test based on three replicates. Concentration and time profiles were compared based on calculated areas under the profiles.

Synthesis of $^{89}$Zr-DFO-VEGF$_{121}$-PEG-Cy5-C' Dot for Targeting VEGFR Overexpressing Cancers As a first step, aminated C' dots, referred to as PEG-NH$_2$—Cy5-C' dots, are synthesized using the methods described herein. Tetramethyl orthosilicate (TMOS) and silane-functionalized Cy5 fluorescent dye are added to an ammonium hydroxide solution (pH~8.5, room temperature (RT)) under vigorous stirring (600 rpm). One day later, (3-aminopropyl)trimethoxysilane (APTMS) and monofunctional PEG-silane with molar mass around 500 (6 to 9 ethylene glycol units) are added to the reaction in sequence at RT under vigorous stirring conditions (600 rpm), and then maintained at 80° C. without stirring. Synthesized PEG-NH$_2$—Cy5-C' dots are collected (after cooling to RT), purified by gel permeation chromatography (GPC), and transferred to deionized (DI) water via spin filtration; particle size and concentration is subsequently determined by fluorescence correlation spectroscopy (FCS) analysis.

Next, PEG-NH$_2$—Cy5-C' dots are diluted into phosphate-buffered saline (PBS) (pH 7.4) buffer solution. DBCO-PEG$_4$-NHS ester (in DMSO) is added to the reaction mixture, and reacted under shaking (640 rpm) for 1 hour at RT. DBCO surface density can be controlled by altering the reaction ratio between PEG-NH$_2$—Cy5-C' dots and DBCO-PEG4-NHS ester. DFO-NCS (in DMSO) is then added, and the reaction pH is adjusted to 8-9 in order to promote surface conjugation of DFO to C' dots (reaction time ~2 h). A reaction ratio of PEG-NH$_2$—Cy5-C' dots to DFO-NCS of 1:20 results in conjugation of at least 3-4 DFO per C' dot. As-synthesized DFO-DBCO-PEG-Cy5-C' dots are then purified by passing particles through a PD-10 column, with PBS as the mobile phase to remove unreacted DBCO and DFO molecules.

To attach VEGF$_{121}$ targeting ligands, 2.5 nmols of azide-containing VEGF$_{121}$ is added into 100 µL PBS solution of DFO-DBCO-PEG-Cy5-C' dots (5 µM). VEGF$_{121}$ is about 12 kDa. The number of VEGF$_{121}$ per particle can be precisely tuned by changing the reaction ratio or the concentration of DFO-DBCO-PEG-Cy5-C' dots used. The mixture is continuously shaken at room temperature (RT) for 24 hours. Free VEGF$_{121}$ ligands are removed by GPC purification. Purified DFO-VEGF$_{121}$-PEG-Cy5-C' dot immunoconjugates are then suspended in PBS for flow cytometry and $^{89}$Zr radiolabeling studies.

Alternatively, DFO-VEGF$_{121}$-PEG-Cy5-C' dot can also be synthesized by functionalizing a pre-synthesized aminated DBCO-PEG-Cy5-C' dots with DFO and VEGF$_{121}$.

For $^{89}$Zr labeling, 0.75 nmol of DFO-VEGF$_{121}$-PEG-Cy5-C' dots can be mixed with 1 mCi of $^{89}$Zr-oxalate in HEPES buffer (pH 8) at 37° C. for 60 min; final labeling pH was kept at 7-7.5. An EDTA challenge process is introduced to remove any non-specifically bound $^{89}$Zr by incubating the mixture at 37° C. for 30-60 min. The final $^{89}$Zr labeling yield ranges from 70 to 80%. As synthesized $^{89}$Zr-DFO-VEGF$_{121}$-PEG-Cy5-C' dots can be purified using a PD-10 column. Radiochemical purity is estimated to be greater than 99% (by using Radio-TLC) with a specific activity of ~1000 Ci/mmol.

What is claimed is:

1. A nanoprobe created from an aminated nanoparticle, the nanoprobe comprising:
   a silica nanoparticle that comprises a polyethylene glycol (PEG) layer;
   a targeting agent conjugated to the silica nanoparticle via an amine group underneath the PEG layer; and
   a radiolabel conjugated to the silica nanoparticle via another amine group underneath the PEG layer,
   wherein the silica nanoparticle has a diameter no greater than 20 nanometers.

2. The nanoprobe of claim 1, wherein the radiolabel comprises 89Zr.

3. The nanoprobe of claim 1, wherein the targeting agent comprises a targeting peptide.

4. The nanoprobe of claim 3, wherein the targeting peptide comprises a member selected from the group consisting of arginylglycylaspartic acid (RGD), cyclic arginylglycylaspartic acid (cRGD), an analog of RGD, alpha-Melanocyte-stimulating hormone (alphaMSH), and any peptide known to be immunomodulatory and anti-inflammatory in nature.

5. The nanoprobe of claim 1, wherein the targeting agent comprises an antibody fragment, and wherein the antibody fragment is in a range from about 5 kDa to about 25 kDa.

6. The nanoprobe of claim 1, wherein the targeting agent comprises an antibody fragment, and wherein the antibody fragment is from about 20 kDa to about 45 kDa.

7. The nanoprobe of claim 1, wherein the targeting agent comprises an antibody fragment, and wherein the antibody fragment is from about 40 kDa to about 80 kDa.

8. The nanoprobe of claim 1, wherein the silica nanoparticle comprises a silica-based core and a silica shell surrounding at least a portion of the silica-based core.

9. The nanoprobe of claim 1, wherein the silica nanoparticle comprises a silica-based core and a fluorescent compound within the silica-based core.

10. The nanoprobe of claim 1, wherein the targeting agent comprises $VEGF_{121}$.

11. The nanoprobe of claim 1, wherein the targeting agent comprises an antibody fragment selected from the set consisting of a Fab fragment, a single chain variable fragment (scFv), and a single domain antibody (sdAb) fragment.

12. The nanoprobe of claim 11, wherein the antibody fragment is a single chain variable fragment (scFv).

13. The nanoprobe of claim 11, wherein the antibody fragment is a single domain antibody (sdAb) fragment.

14. The nanoprobe of claim 1, wherein from one to ten targeting agents are conjugated to the silica nanoparticle via amine groups.

15. The nanoprobe of claim 1, wherein the silica nanoparticle has a diameter no greater than 15 nanometers.

16. The nanoprobe of claim 1, wherein the silica nanoparticle has a diameter in a range from 1 nm to 20 nm.

17. The nanoprobe of claim 1, wherein the targeting agent comprises a member selected from the set consisting of anti-CEA scFv, anti-GPIIb/IIIa, anti-VEGF-A, anti-VEGF-R, and anti-TNF-α.

18. The nanoprobe of claim 1, wherein the nanoprobe further comprises one or more imaging agents.

19. The nanoprobe of claim 18, wherein the one or more imaging agents comprise a PET or SPECT tracer.

20. The nanoprobe of claim 19, wherein the PET or SPECT tracer comprises a member selected from the group consisting of $^{89}Zr$, $^{64}Cu$, $^{18}F$ fluorodeoxyglucose, $^{177}Lu$, $^{225}At$, and $^{90}Y$.

21. The nanoprobe of claim 1, further comprising a therapeutic agent.

22. The nanoprobe of claim 1, wherein the targeting agent comprises a recombinant antibody fragment.

* * * * *

UNITED STATES PATENT AND TRADEMARK OFFICE
CERTIFICATE OF CORRECTION

PATENT NO. : 11,559,591 B2
APPLICATION NO. : 16/616368
DATED : January 24, 2023
INVENTOR(S) : Michelle S. Bradbury et al.

It is certified that error appears in the above-identified patent and that said Letters Patent is hereby corrected as shown below:

In the Claims

At Column 1, Claim number 2, Line number 16, "comprises 89Zr." should read "comprises $^{89}$Zr."

Signed and Sealed this
Fourteenth Day of March, 2023

Katherine Kelly Vidal
*Director of the United States Patent and Trademark Office*